US009775525B2

(12) United States Patent
Yoshioka et al.

(10) Patent No.: US 9,775,525 B2
(45) Date of Patent: Oct. 3, 2017

(54) CONCENTRATION PRESENCE/ABSENCE DETERMINING DEVICE AND CONTENT EVALUATION APPARATUS

(71) Applicant: PANASONIC CORPORATION, Osaka (JP)

(72) Inventors: Mototaka Yoshioka, Osaka (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 963 days.

(21) Appl. No.: 13/716,964

(22) Filed: Dec. 17, 2012

(65) Prior Publication Data

US 2013/0131521 A1 May 23, 2013

Related U.S. Application Data

(63) Continuation of application No. PCT/JP2012/002842, filed on Apr. 25, 2012.

(30) Foreign Application Priority Data

May 2, 2011 (JP) .................................. 2011-103229

(51) Int. Cl.
*A61B 5/1455* (2006.01)
*A61B 5/0205* (2006.01)
(Continued)

(52) U.S. Cl.
CPC ............ *A61B 5/0205* (2013.01); *A61B 5/026* (2013.01); *A61B 5/14551* (2013.01); *A61B 5/4064* (2013.01); *A61B 5/165* (2013.01)

(58) Field of Classification Search
None
See application file for complete search history.

(56) References Cited

U.S. PATENT DOCUMENTS 6,640,133 B2  10/2003  Yamashita et al.
7,142,906 B2  11/2006  Yamashita et al.
(Continued)

FOREIGN PATENT DOCUMENTS

JP      9-149894     6/1997
JP      2002-172106  6/2002
(Continued)

OTHER PUBLICATIONS

International Search Report (in English language) issued in International Application No. PCT/JP2012/002842 on May 22, 2012.

*Primary Examiner* — Eric Winakur
*Assistant Examiner* — Marjan Fardanesh
(74) *Attorney, Agent, or Firm* — Wenderoth, Lind & Ponack, L.L.P.

(57) ABSTRACT

A concentration presence/absence determining device includes: a brain blood flow volume obtaining unit configured to obtain a brain blood flow volume of the user; a varying threshold obtaining unit configured to obtain a varying threshold that is a value smaller than the brain blood flow volume of the user at a base time; and an determining unit configured to determine that the user concentrates, when the brain blood flow volume obtained by the brain blood flow volume obtaining unit falls below the varying threshold obtained by the varying threshold obtaining unit.

23 Claims, 50 Drawing Sheets

(51) Int. Cl.
*A61B 5/026* (2006.01)
*A61B 5/00* (2006.01)
*A61B 5/16* (2006.01)

(56) References Cited

U.S. PATENT DOCUMENTS

| | | | |
|---|---|---|---|
| 7,774,047 | B2 | 8/2010 | Yamashita et al. |
| 7,853,122 | B2 | 12/2010 | Miura et al. |
| 7,974,671 | B2 | 7/2011 | Fujiwara et al. |
| 2001/0018554 | A1 | 8/2001 | Yamashita et al. |
| 2002/0095089 | A1 | 7/2002 | Yamamoto et al. |
| 2004/0013398 | A1 | 1/2004 | Miura et al. |
| 2004/0127784 | A1 | 7/2004 | Yamashita et al. |
| 2004/0152060 | A1 | 8/2004 | Ando et al. |
| 2006/0184045 | A1 | 8/2006 | Yamashita et al. |
| 2006/0184046 | A1 | 8/2006 | Yamashita et al. |
| 2006/0184047 | A1 | 8/2006 | Yamashita et al. |
| 2007/0083097 | A1 | 4/2007 | Fujiwara et al. |
| 2008/0188729 | A1* | 8/2008 | Sato .................. A61B 5/4017 600/340 |
| 2008/0255949 | A1* | 10/2008 | Genco .................. A61B 5/0205 705/14.4 |
| 2008/0295126 | A1 | 11/2008 | Lee et al. |
| 2009/0270754 | A1 | 10/2009 | Moridaira |
| 2011/0082677 | A1 | 4/2011 | Kawasaki et al. |

FOREIGN PATENT DOCUMENTS

| | | |
|---|---|---|
| JP | 2003-93390 | 4/2003 |
| JP | 2004-21870 | 1/2004 |
| JP | 2004-65902 | 3/2004 |
| JP | 2004-229948 | 8/2004 |
| JP | 2008-136210 | 6/2008 |
| JP | 2009-265876 | 11/2009 |
| JP | 2010-94493 | 4/2010 |
| JP | 2010-104457 | 5/2010 |
| JP | 2010-520554 | 6/2010 |
| WO | 2005/034761 | 4/2005 |
| WO | 2008/108806 | 9/2008 |
| WO | 2009/148069 | 12/2009 |

* cited by examiner

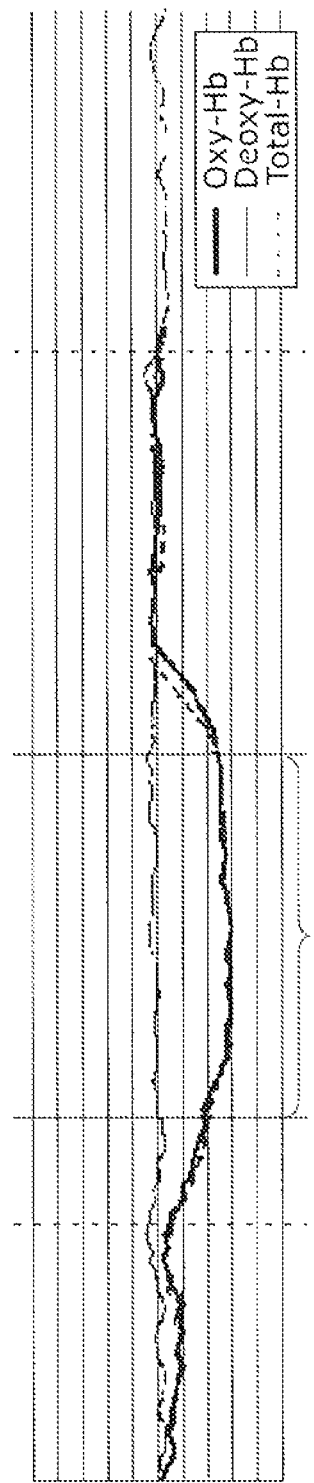

FIG. 22

Multiple-degree of concentration information

| Ratio of persons who concentrate | The number of subjects whose degree of concentration is higher than or equal to threshold (60%) / total number of subjects |
|---|---|
| Average concentration start time | Σ decrease start times of subjects / total number of subjects |
| Average concentration end time | Σ increase start times of subjects / total number of subjects |

FIG. 35B

```
Content item 1
<Name> Commercial of digital camera of Company A
<Scene tag>
..
<1> Period (1-2 seconds), Area (200, 300, 500, 100), Actress
<2> Period (3-4 seconds), Area (200, 300, 500, 300), Camera
<3> Period (5-7 seconds), Area (200, 300, 600, 100), Description of function
.. ..
<4> Period (28-30 seconds), Area (300, 400, 300, 100), Logo of Company A
```

1105a

CONCENTRATION PRESENCE/ABSENCE DETERMINING DEVICE AND CONTENT EVALUATION APPARATUS

CROSS REFERENCE TO RELATED APPLICATION

This is a continuation application of PCT International Application No. PCT/JP2012/002842 filed on Apr. 25, 2012, designating the United States of America, which is based on and claims the benefit of priority to Japanese Patent Application No. 2011-103229 filed on May 2, 2011. The entire disclosures of the above-identified applications, including the specifications, drawings and claims are incorporated herein by reference in their entirety.

FIELD

One or more exemplary embodiments disclosed herein relate generally to a concentration presence/absence determining device and a content evaluation apparatus that determine whether or not a user concentrates on a task, based on a change tendency of a brain blood flow volume when the user executes a task (hereinafter referred to as "task time").

BACKGROUND

Conventionally, there exists an apparatus that determines a psychological state of a user based on change in a brain blood flow volume (for example, see Patent Literature (PTL) 1). Furthermore, there exists a method for determining a degree of concentration based on change in a brain blood flow volume (for example, see PTL 2).

CITATION LIST

Patent Literature

[PTL 1] Japanese Unexamined Patent Application Publication No. 2003-93390
[PTL 2] Japanese Unexamined Patent Application Publication No. 2004-229948
[PTL 3] Japanese Unexamined Patent Application Publication No 2004-65902
[PTL 4] Japanese Unexamined Patent Application Publication No 2004-21870

SUMMARY

Technical Problem

However, with the current near-infrared spectroscopy (NIRS), the validity and the reproducibility of the hypotheses are low.

One non-limiting and exemplary embodiment provides a concentration presence/absence determining device and a content evaluation apparatus that can determine whether or not the user concentrates with accuracy.

Solution to Problem

The inventors conducted an experiment aimed at measuring a brain blood flow volume of the user who was concentrating on a task, and obtained a significant outcome that the brain blood flow volume decreased during the concentration. The concentration presence/absence determining device and the content evaluation apparatus according to one non-limiting and exemplary embodiment have been conceived based on such knowledge, and determine whether or not the user concentrates based on a decreasing tendency in a brain blood flow volume.

The concentration presence/absence determining device according to one non-limiting and exemplary embodiment is a concentration presence/absence determining device that determines whether or not a user concentrates, and includes: a brain blood flow volume obtaining unit configured to obtain a brain blood flow volume of the user; a varying threshold obtaining unit configured to obtain a varying threshold that is a value smaller than the brain blood flow volume of the user at a base time; and an determining unit configured to determine that the user concentrates, when the brain blood flow volume obtained by the brain blood flow volume obtaining unit falls below the varying threshold obtained by the varying threshold obtaining unit.

The present disclosure can be implemented as not only a concentration presence/absence determining device including such characteristic processing units but also a concentration presence/absence determining method including the characteristic processing units included in the concentration presence/absence determining device as steps, and a program causing a computer to execute the characteristic steps included in the concentration presence/absence determining method. Furthermore, such a program can be distributed via recording media such as a Compact Disc-Read Only Memory (CD-ROM), and via communication networks, such as the Internet.

Advantageous Effects

The concentration presence/absence determining device and the content evaluation apparatus according to one non-limiting and exemplary embodiment can determine whether or not the user concentrates with accuracy.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 15B is a graph indicating an example of a concentration pattern.

FIG. 22 is a table for describing a multiple-degree of concentration.

FIG. 35B is an example of provided information stored in the provided information storage unit.

Figure 1:
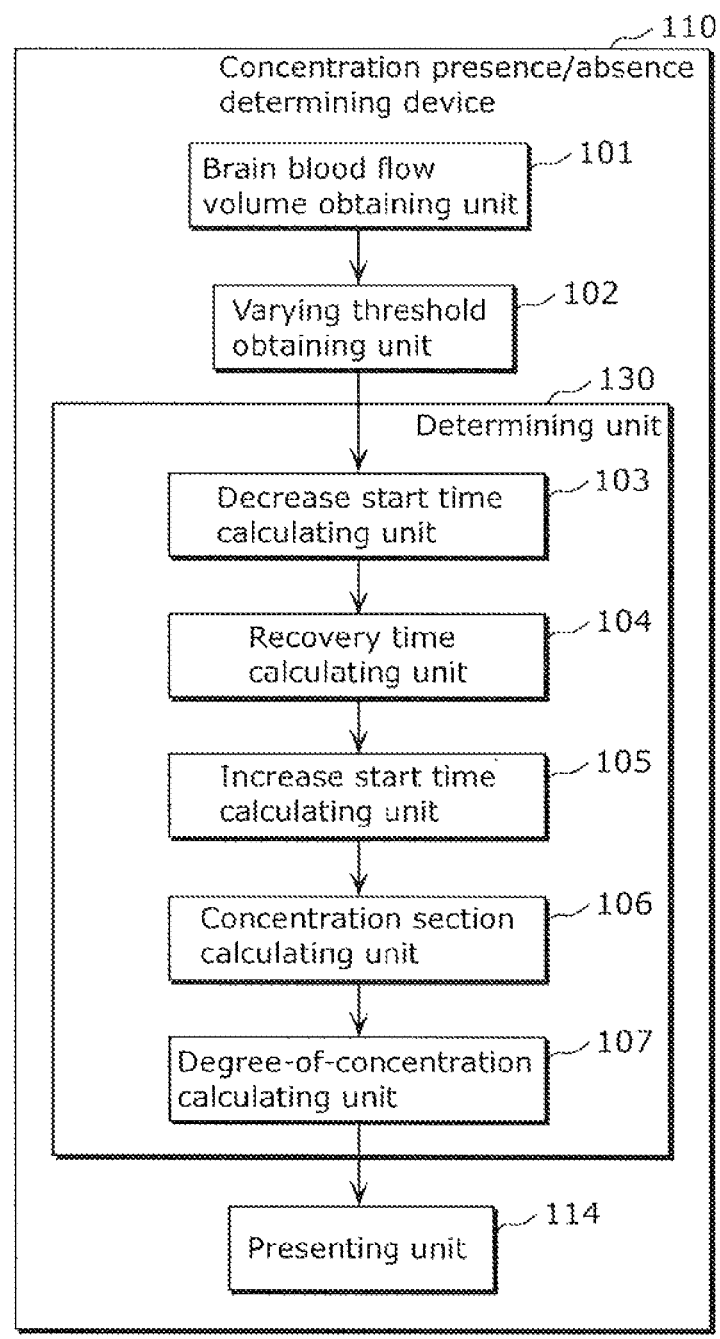
FIG. 1 is a block diagram illustrating a configuration of a concentration presence/absence determining device according to Embodiment 1.

DESCRIPTION OF EMBODIMENTS (Underlying Knowledge Forming Basis of the Present Disclosure)

Generally, it is said that the brain works in response to visual and audible stimuli, consumes oxygen, and to make up the loss, supplies an amount of oxygen larger than the amount consumed (Blood Oxygenation Level Dependent (BOLD) phenomenon). Oxygen is supplied according to increase in a blood flow and in an amount of oxygenated hemoglobin. Here, in PTL 1, a near-infrared spectroscopy (NIRS) sensor detects change in the amount of oxygenated hemoglobin. Based on the assumption that the brain actively works when the amount of oxygenated hemoglobin increases, a psychological state of the user is determined.

Similarly, in PTL 2, based on the assumption that the brain works and a blood flow and an amount of oxygenated hemoglobin increase when the user is concentrating on a task, a degree of concentration is determined by detecting the increase in a blood flow and in an amount of oxygenated hemoglobin.

Furthermore, PTL 3 also discloses that when a person is concentrating on a task, a brain blood flow concentrates on the frontal lobe. PTL 3 also discloses that when a subject sees pessimistic words, such as "sad", "worry", and "depressive", the frontal lobe has anemia and the brain blood flow decreases. Furthermore, PTL 3 discloses a method for assessing a psychological state of a subject, using the characteristics that the brain blood flow increases when the subject is concentrating on a task and the brain blood flow decreases when the subject sees a pessimistic word.

However, with the current NIRS, the validity and the reproducibility of the hypotheses are low. Specifically, even when change in a brain blood flow volume when the user is performing a task on which the user can be concentrating is measured, the brain blood flow volume and an amount of oxygenated hemoglobin do not always increase. Furthermore, when the same person performs the same task again, the reproducibility is frequently low. It is said that such a result is caused by artifacts, such as personal differences and body movement. The current NIRS sensors are extremely subject to increase or decrease in a brain blood flow volume in a measurement optical path, such as the brain blood flow volume inside the brain and even in the skin surface of the brain. Furthermore, increase in the brain blood flow volume measured by the current NIRS sensors is not always associated with the brain activity.

In relation to the method for determining whether or not the user concentrates on a task by detecting increase in a brain blood flow volume as disclosed by PTLs 1 to 3 in the Background section, the inventors have found the difficulty in determining whether or not the user concentrates on the task with accuracy.

Furthermore, PTL 3 discloses that the brain blood flow concentrates on the frontal lobe, that is, increases, when a subject is generally concentrating on a task, whereas the frontal lobe has anemia and the brain blood flow decreases when the subject sees a negative word. However, even when the method in which the brain blood flow increases when a subject is concentrating on a task and the brain blood flow decreases when the subject sees a negative word as disclosed in PTL 3 is used, the brain blood flow does not always increase during the concentration on the task. Thus, it is difficult to determine whether or not the user concentrates on the task with accuracy, Specifically, the method disclosed in PTL 3 may indicate that the person concentrates on a task when the brain blood flow increases whereas the person sees a negative word when the brain blood flow decreases.

Furthermore, PTL 3 merely discloses that the brain blood flow decreases when the person sees a negative word, and fails to disclose any specific decreasing tendency of the brain blood flow and any method for determining a psychological state. The inventors have found the difficulty in determining a psychological state of the user based on only the phenomenon in which the brain blood flow decreases, because the current NIRS is subject to the artifacts, such as personal differences and body movement.

The concentration presence/absence determining device according to one non-limiting and exemplary embodiment is a concentration presence/absence determining device that determines whether or not a user concentrates, and includes: a brain blood flow volume obtaining unit configured to obtain a brain blood flow volume of the user; a varying threshold obtaining unit configured to obtain a varying threshold that is a value smaller than the brain blood flow volume of the user at a base time; and an determining unit configured to determine that the user concentrates, when the brain blood flow volume obtained by the brain blood flow volume obtaining unit falls below the varying threshold obtained by the varying threshold obtaining unit.

With the configuration, the concentration presence/absence determining device determines that the user concentrates when the brain blood flow volume falls below the varying threshold. Thus, whether or not the user concentrates can be determined with accuracy.

For example, the determining unit includes: a decrease start time calculating unit configured to calculate, as a decrease start time, a time at which the brain blood flow volume falls below the varying threshold; a recovery time calculating unit configured to calculate, as a recovery time, a time at which the brain blood flow volume exceeds the varying threshold after the decrease start time calculated by the decrease start time calculating unit; an increase start time calculating unit configured to calculate, as an increase start time, a time at which the brain blood flow volume starts to increase between the decrease start time calculated by the decrease start time calculating unit and the recovery time calculated by the recovery time calculating unit; and a concentration section calculating unit configured to calculate, as a concentration section, a period in which the user concentrates, the period ranging from the decrease start time calculated by the decrease start time calculating unit to the increase start time calculated by the increase start time calculating unit.

The brain blood flow volume increases when the user is lacking in concentration. Thus, a concentration section that is a period in which the user concentrates can be calculated with accuracy by calculating a period from the time when the brain blood flow volume falls below the varying threshold to the time when the brain blood flow volume starts to increase.

Furthermore, the determining unit may further include a degree-of-concentration calculating unit configured to calculate, as a degree of concentration of the user, a ratio of the concentration section to a target section that is a period during which the user executes a task, the concentration section being calculated by the concentration section calculating unit.

With the configuration, the concentration presence/absence determining device can calculate a degree of concentration of the user with accuracy.

Furthermore, the degree-of-concentration calculating unit may be further configured to calculate a weighted degree of concentration of the user by multiplying the calculated degree of concentration by a weight that increases with a larger amount of decrease in the brain blood flow volume in the concentration section.

As the concentration continues longer, the brain blood flow volume continues to decrease with the passage of time. As the amount of decrease in the brain blood flow volume is larger, the degree of concentration is probably higher. Thus, the concentration presence/absence determining device can calculate a degree of concentration with accuracy by multiplying the degree by the weight.

Furthermore, the degree-of-concentration calculating unit may be further configured to calculate a weighted degree of concentration of the user by multiplying the calculated degree of concentration by a weight that increases with a higher ratio of an amount of decrease in the brain blood flow volume in the concentration section to an amount of decrease in the brain blood flow volume when the user is at rest.

The amount of decrease in the brain blood flow volume at a rest time differs for each user. Thus, the concentration presence/absence determining device can calculate a degree of concentration with accuracy by multiplying the degree by the weight based on the ratio without being influenced by the characteristics of the user.

Furthermore, the amount of decrease in the brain blood flow volume in the concentration section may be a difference between the brain blood flow volume when the user is at rest and a smallest value of the brain blood flow volume in the concentration section.

Furthermore, the amount of decrease in the brain blood flow volume in the concentration section may be an absolute value of an integrated value of brain blood flow volumes ranging from the decrease start time to a time at which the brain blood flow volume has a smallest value in the concentration section.

Furthermore, the degree-of-concentration calculating unit may be further configured to classify a pattern of change in the brain blood flow volume in the target section into one of patterns, and calculate a weighted degree of concentration of the user by multiplying the calculated degree of concentration by a weight assigned to the classified pattern.

The concentration presence/absence determining device can calculate a degree of concentration by defining patterns of change in the brain blood flow volume and assigning an appropriate weight to each of the patterns.

Specifically, the degree-of-concentration calculating unit is configured to classify the pattern of change in the brain blood flow volume in the target section into one of the patterns, based on one of (i) the ratio of the concentration section to the target section, (ii) the number of concentration sections within the target section, and (iii) a ratio of a smallest value of the brain blood flow volume in a first concentration section to a smallest value of the brain blood flow volume in a second concentration section, the first concentration section and the second concentration section being included in the target section, and the concentration sections including the concentration section.

Furthermore, the degree-of-concentration calculating unit may be further configured to calculate a weighted degree of concentration of the user by multiplying the calculated degree of concentration by a weight that increases with the less number of concentration sections within the target section, the concentration sections including the concentration section.

When the number of concentration sections within the target section is many, a degree of concentration is probably lower because the user intermittently concentrates in the target section. In contrast, when the number of concentration sections is less, a degree of concentration is probably higher because the user continuously concentrates. Thus, the concentration presence/absence determining device can calculate a degree of concentration with accuracy by multiplying the degree by the weight.

Furthermore, the brain blood flow volume obtaining unit may be configured to obtain brain blood flow volumes measured at a plurality of measurement parts of the brain of the user, the brain blood flow volumes including the brain blood flow volume, and the degree-of-concentration calculating unit may be configured to calculate, for each of the measurement parts, a ratio of an amount of decrease in the brain blood flow volume in the concentration section to an amount of decrease in the brain blood flow volume when the user is at rest, and calculate a degree of concentration of the user, using one of the brain blood flow volumes measured at a measurement part having a highest ratio that is calculated.

The sensitivity for measuring the brain blood flow volume is probably higher as the measurement part has the higher ratio.

Furthermore, the measurement parts may be grouped into groups, and the degree-of-concentration calculating unit may be configured to calculate, for each of the groups, an average of ratios of (I) amounts of decrease in brain blood flow volumes measured at measurement parts included in the group, in the concentration section (ii) to amounts of decrease in brain blood flow volumes measured at the measurement parts included in the group when the user is at rest, and calculate a degree of concentration of the user, using an average of the brain blood flow volumes measured at the measurement parts included in one of the groups having a highest average of the ratios that is calculated.

The degree of concentration can be calculated without any influence of noise by grouping the measurement parts and calculating the degree of concentration of the user using the average of the brain blood flow volumes.

Furthermore, the concentration presence/absence determining device may include a presenting unit configured to present the degree of concentration of the user or the weighted degree of concentration of the user both of which are calculated by the degree-of-concentration calculating unit.

Furthermore, the brain blood flow volume obtaining unit may be configured to obtain a brain blood flow volume of each of users including the user, the degree-of-concentration calculating unit may be configured to calculate a degree of concentration of each of the users, and the concentration presence/absence determining device may further include a multiple-degree of concentration calculating unit configured to calculate, as a multiple-degree of concentration, one of (i) a ratio of the number of users each having the degree of concentration that exceeds a predetermined threshold to the total number of users, (ii) an average of decrease start times of the users, and (iii) an average of increase start times of the users.

The calculation of a multiple-degree of concentration makes it possible to understand an overall concentration state of users in a class, such as determining whether or not the English listening test is a material on which the users concentrate or all the students concentrate on the material.

The concentration presence/absence determining device may further include: a line of sight obtaining unit configured to obtain a line-of-sight position of the user; and a target section calculating unit configured to calculate, as a target section, a period during which the line-of-sight position of the user obtained by the line of sight obtaining unit is within a predetermined area.

Detection of a line-of-sight position makes it possible to determine a state of how the user tackles a task and calculate a target section with higher accuracy. Thus, a degree of concentration according to each target section can be calculated.

The content evaluation apparatus according to one non-limiting and exemplary embodiment is a content evaluation apparatus including: the concentration presence/absence determining device that determines a concentration state; a line of sight obtaining unit configured to obtain a line-of-sight position of the user; a gaze degree calculating unit configured to calculate a gaze degree that is a degree at which the user gazes at a provided image that is an image included in an image content item viewed by the user, with reference to provided information based on a position relationship, during a display period, between the line-of-sight position and a display area of the provided image, the provided information being information including the display area and the display period, the display period being a period during which the provided image is displayed in the display area; and an evaluation information determining unit configured to determine, as an evaluation of the user to the image content item, evaluation information corresponding to the gaze degree calculated by the gaze degree calculating unit and to the concentration state determined by the concentration presence/absence determining device, with reference to an evaluation information template including evaluation information of the image content item associated with a pair of a gaze degree and a concentration state.

The content evaluation apparatus with the configuration can evaluate an image content item using, as evaluation axes, a concentration state of the user who viewed the content and a gaze degree at which the user gazed at a specific image included in the image content. As a result, the content creator can easily rank a desired content item in view of the purposes of the creation of the content item, on evaluation axes of a concentration state and a gaze degree. Thus, the content creator can assess a difference between the evaluation determined by the content evaluation apparatus and the desired content item. Thus, the content creator can easily use the evaluation determined by the content evaluation apparatus for improving the content item.

For example, the evaluation information template includes the evaluation information indicating an evaluation that increases with a higher gaze degree of the user and a higher degree of concentration of the user, the gaze degree calculated by the gaze degree calculating unit.

Accordingly, a content item can be more appropriately evaluated. This is because when the content item is intended for advertisement through a commercial video, states where the user is concentrating and gazes at a provided image that the content creator wants to appeal are assumed to be favorable.

Furthermore, the gaze degree calculating unit may be configured to calculate a higher gaze degree as a period during which the line-of-sight position is retained in the display area is longer.

Accordingly, the length of a retention period can be reflected on the magnitude of a gaze degree. As a result, the gaze degree can be calculated with higher accuracy.

Furthermore, when the provided age represents text information, the gaze degree calculating unit may be configured to calculate a higher gaze degree as a movement direction of the line-of-sight position matches a direction in which the text information is written at a higher degree.

Accordingly, it is possible to more accurately identify the user gazing at the text information. As a result, the accuracy for calculating a gaze degree can be increased.

Furthermore, the gaze degree calculating unit may be configured to determine whether or not a distance between (i) a line-of-sight position during each of display periods included in the provided information and (ii) a display area corresponding to the display period is smaller than a predetermined threshold, for each of the display periods, determine that the user gazes during at least one of the display periods when the distance is smaller than the predetermined threshold, and calculate a gaze degree as a ratio of a sum of the at least one of the display periods during which it is determined that the user gazes, to the display periods included in the provided information.

Accordingly, the gaze degree can be specifically calculated per image content item.

Furthermore, the image content item may be a content item of a commercial video.

Accordingly, a television commercial that is repeatedly broadcasted and others can be appropriately evaluated.

The general or specific aspects may be implemented by a system, a method, an integrated circuit, a computer program, or a computer-readable recording medium, such as a CD-ROM, or by an arbitrary combination of the system, the method, the integrated circuit, the computer program, and the recording medium.

Embodiments will be described with reference to the drawings.

Each of Embodiments to be described below is a specific example of the present disclosure. The values, shapes, materials, constituent elements, positions and connections of the constituent elements, steps, and orders of the steps indicated in Embodiments are examples, and do not limit the present disclosure. The constituent elements in Embodiments that are not described in independent Claims that describe the most generic concept of the present disclosure are described as arbitrary constituent elements.

Embodiment 1

A concentration presence/absence determining device according to Embodiment 1 will be described hereinafter.

FIG. 1 is a block diagram illustrating a configuration of a concentration presence/absence determining device 110 according to Embodiment 1.

In FIG. 1, the concentration presence/absence determining device 110 is a device that determines whether or not the user concentrates on a task based on a brain blood flow volume of the user at a task time, and includes a brain blood flow volume obtaining unit 101, a varying threshold obtaining unit 102, an determining unit 130, and a presenting unit 114. The presenting unit 114 does not always have to be included in the concentration presence/absence determining device 110.

Figure 2:
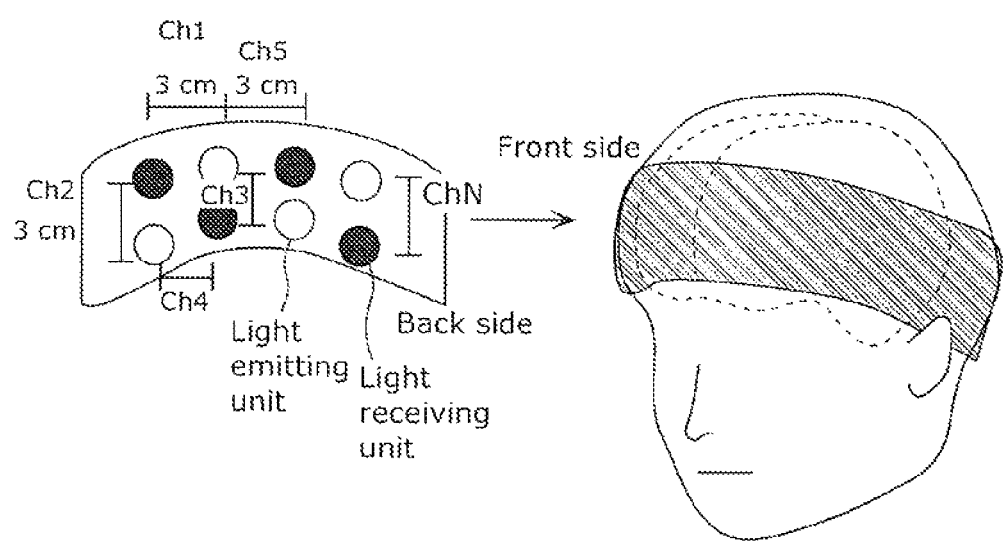
FIG. 2 illustrates an example of a brain blood flow volume obtaining unit.

The brain blood flow volume obtaining unit 101 obtains a brain blood flow volume of the user. FIG. 2 illustrates an example of the brain blood flow volume obtaining unit 101. The brain blood flow volume obtaining unit 101 is, for example, a near-infrared sensor (NIRS sensor). In recent years, it is known that change in a brain blood flow volume can be detected using the NIRS sensor. The outline will be described hereinafter. Here, the brain blood flow volume obtaining unit 101 is not limited to such, and may simply obtain data of a brain blood flow volume from outside.

Hemoglobin in the blood is combined with oxygen to transfer the oxygen to the body. The NIRS sensor includes a light emitting unit that emits near-infrared light having a wavelength ranging between 700 nm and 1000 nm inclusive, and a light receiving unit that receives the near-infrared light. By irradiating the body tissue with the near-infrared light and receiving the light through the body tissue, change in a hemoglobin oxygenation state in the blood of the brain can be detected based on an amount of decrease in the light. For example, change in a blood flow in the frontal lobe can be detected by wearing the NIRS sensor on the forehead. Furthermore, generally, intervals of the NIRS sensors are 3 cm based on the relationship with the length of a light path with which the brain blood flow volume is measured.

Figure 3:
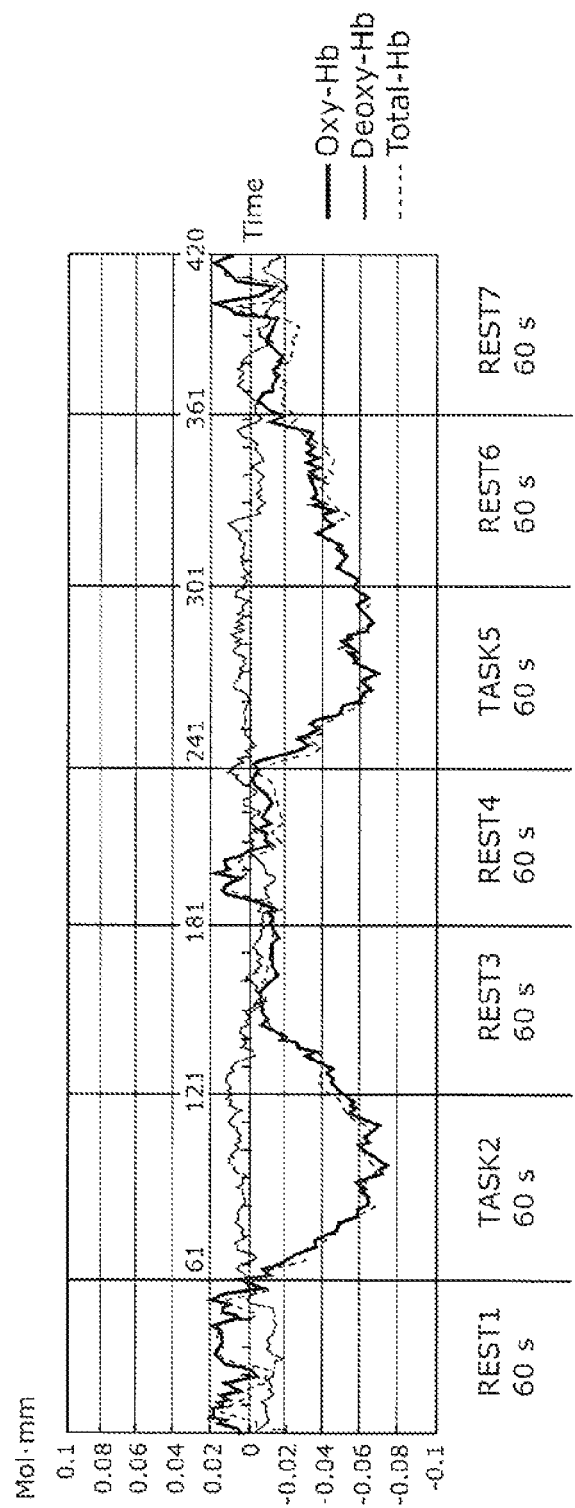
FIG. 3 is a graph indicating temporal change in a brain blood flow volume when the user concentrates on a task.

FIG. 3 is a graph indicating temporal change in a brain blood flow volume. FIG. 3 is real data indicating temporal change in a brain blood flow volume in the frontal lobe obtained when a Japanese man was listening to the English news. The thick line indicates an amount of oxygenated hemoglobin (oxy-Hb) that is hemoglobin combined with oxygen, the thin line indicates an amount of deoxygenated hemoglobin (deoxy-Hb) that is hemoglobin not combined with oxygen, and the thin dotted line indicates an amount of total hemoglobin (total-Hb). The horizontal axis indicates a time (seconds). The vertical axis indicates, assuming the brain blood flow volume at a time 0 as 0, each amount of hemoglobin (each brain blood flow volume) that is a difference with the brain blood flow volume at the time 0. The unit of the vertical axis is Mol×mm. The NIRS sensor that is the brain blood flow volume obtaining unit 101 cannot measure an absolute amount of hemoglobin, and generally measures an amount of hemoglobin using Mol×mm that is a unit including a length of a light path.

The NIRS sensor measures a brain blood flow using a block design in which rest times are provided before and after task times. Here, the task is listening to the English news, and the rest time is an open-eye rest time at which the subject remains at rest while the eyes are kept open to comparatively measure change in the brain blood flow at that time. In FIG. 3, TASK2 is a task, and REST1 and REST3 are open-eye rests before and after TASK2, Furthermore, TASK5 is a task, and REST4 and REST6 are open-eye rests before and after TASK5. Two sets of a task and open-eye rests before and after the task are successively performed, and REST7 that is an open-eye rest is lastly provided.

FIG. 3 indicates that amounts of change in the oxygenated hemoglobin, total hemoglobin, and deoxygenated hemoglobin are constant in the first rest (REST1). Furthermore, the oxygenated hemoglobin and the total hemoglobin gradually decrease upon start of TASK2. Then, the oxygenated hemoglobin and the total hemoglobin gradually increase upon end of TASK2 (start of REST3). Approximately 30 seconds later, the oxygenated hemoglobin and the total hemoglobin are back to the state when the measurement started. Then, the amounts of change are almost constant. On the other hand, the deoxygenated hemoglobin has no significant change during the times. Furthermore, the oxygenated hemoglobin and the total hemoglobin gradually decrease upon start of the second task (TASK5) as seen in the first task. Then, the oxygenated hemoglobin and the total hemoglobin gradually increase upon end of TASK5 (start of REST6). Approximately 60 seconds later (REST7), the oxygenated hemoglobin and the total hemoglobin are back to the state when the measurement started.

These results indicate that the blood flow (the oxygenated hemoglobin and the total hemoglobin) in the frontal lobe at the task times decreases.

The phenomenon in which the brain blood flow volume decreases during the time when the subject was concentrating on a task (hereinafter referred to as "a task concentration time") has been verified by the experiments on the other subjects (12 persons) although the decrease amount varied. Furthermore, the reproducibility has also been verified. Furthermore, the phenomenon has been verified by the tasks other than listening to the English news, such as a puzzle and a chess problem.

Figure 4:
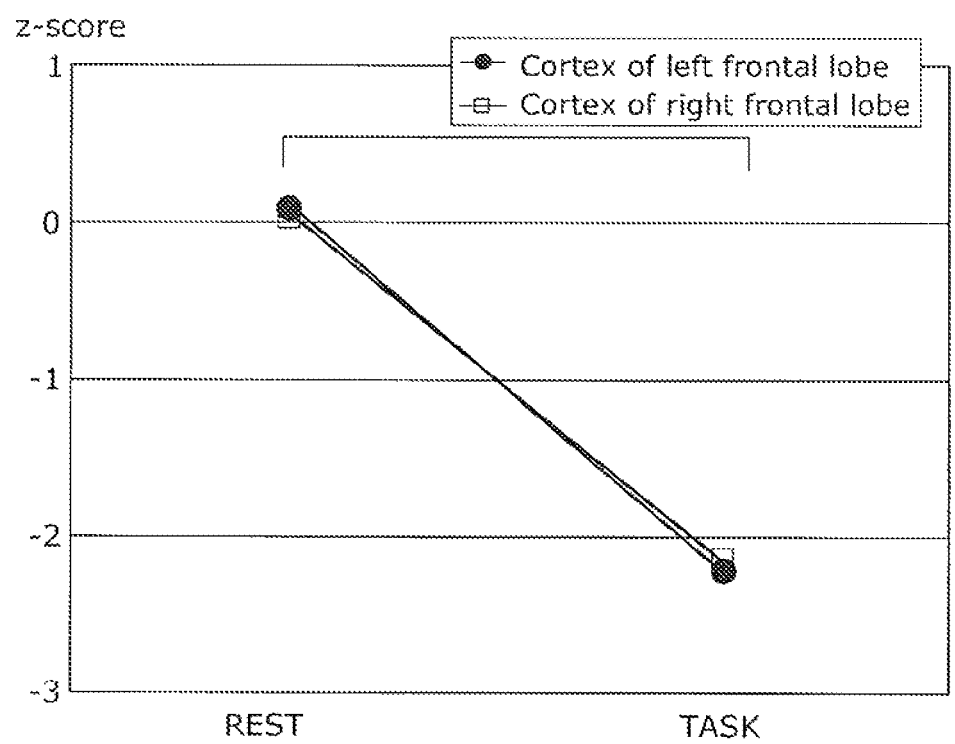
FIG. 4 is a graph indicating, when a task is a chess problem, comparison in amount of decrease in oxygenated hemoglobin (corresponding to a brain blood flow volume) in the frontal lobe between a rest time before solving the chess problem and a task time.

FIG. 4 is a graph indicating a result of comparison in amount of decrease in oxygenated hemoglobin (corresponding to the brain blood flow) in the frontal lobe between a rest time (REST) before solving a chess problem and a task time (TASK). An experiment (REST) in which five subjects remained at rest while their eyes were kept open and a task experiment (TASK) in which the five subjects solved a chess problem displayed on a PC screen for 60 seconds were conducted. During the task concentration time, the brain blood flows decreased as observed in listening to the English news. The amount of decrease in the brain blood flow for 30 seconds (TASK) after starting solving the chess problem with respect to the brain blood flow volume at the rest time (REST) was calculated for each of the subjects. A significant result in which the brain blood flow decreased during execution of the task (TASK) more than the rest time (REST) was obtained by a t-test. The brain blood flow in the left frontal lobe was measured by measuring the oxygenated hemoglobin approximately in an FP1 region in the international 10-20 system, and the brain blood flow in the right frontal lobe was measured by measuring the oxygenated hemoglobin approximately in an FP2 region in the international 10-20 system.

Figure 5:
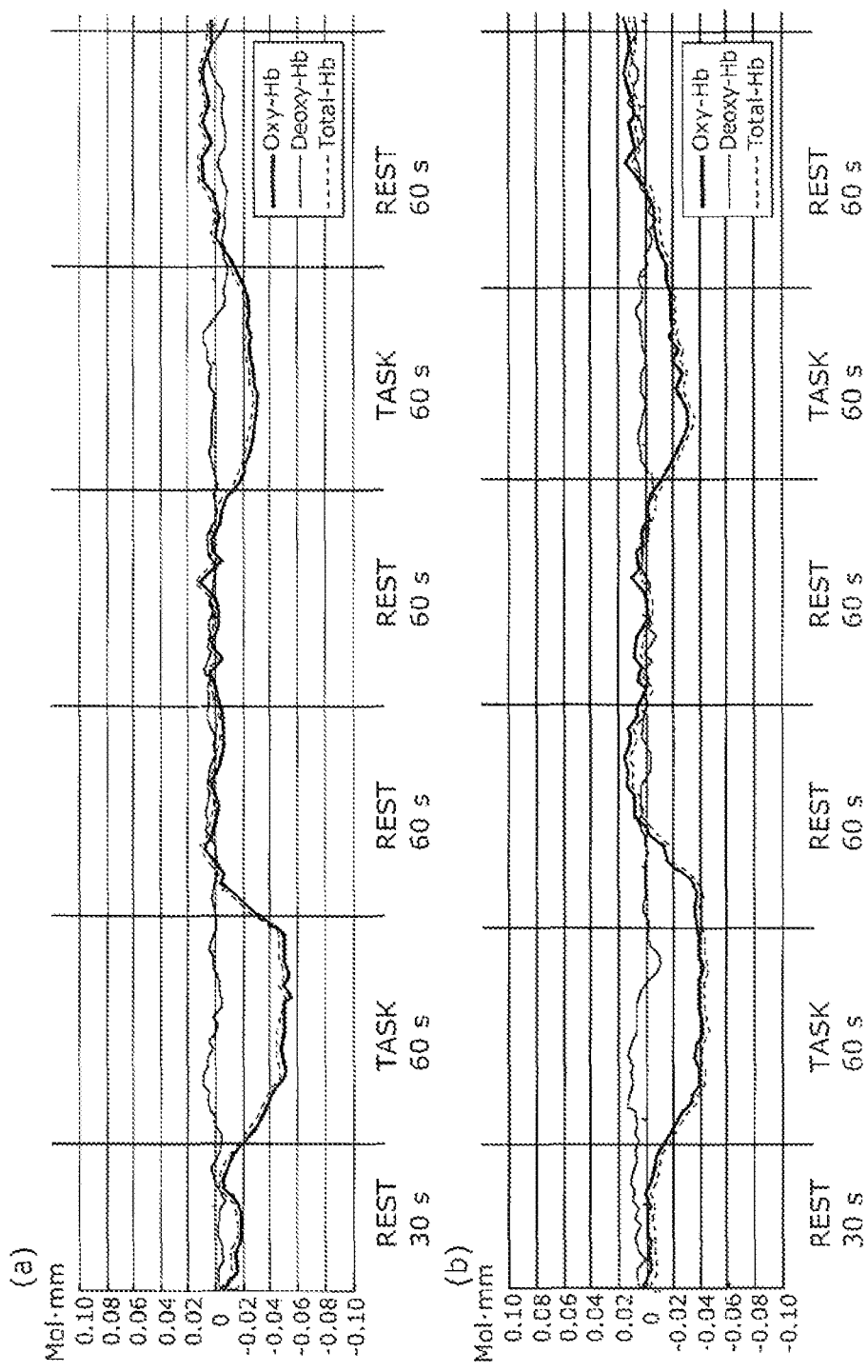
FIG. 5 indicates graphs of part of a result of experiment in the brain blood flow volume.

FIG. 5 indicates graphs of part of a result of an experiment in a brain blood flow volume. In FIG. 5, (a) indicates change in the brain blood flow volume during the time when a subject was listening to the English news. The graph indicates that the amounts of the oxygenated hemoglobin, total hemoglobin, and deoxygenated hemoglobin remain constant during the rest times, and the amounts of oxygenated hemoglobin and total hemoglobin decrease during the task times. Furthermore (b) indicates change in a brain blood flow volume during the time when another subject was solving a chess problem. The graph indicates that the amounts of oxygenated hemoglobin, total hemoglobin, and deoxygenated hemoglobin remain constant during the rest times, and the amounts of oxygenated hemoglobin and total hemoglobin decrease during the task times.

As described above, although it is generally said that the blood flow increases during the brain activity, that is, the oxygenated hemoglobin and the total hemoglobin increase even in the measurement by the NIRS sensor, actually, the reproducibility is low and the experiment has not yet reached the valid level. This indicates that the current NIRS measurement technique has various problems and factors causing the problems, such as influence of not only the brain but also the skin surface.

On the other hand, the inventors obtained, from the experiment using the brain blood flow volume obtaining unit 101 according to Embodiment 1 (NIRS measurement technique), an outcome in that the brain blood flow volume decreases during the task concentration time, which is different from the general phenomenon in which the brain blood flow volume increases during the time.

There seems several reasons for this phenomenon. One aspect is that the frontal lobe has no BOLD response that is generally called, or the phenomenon is not large enough to be detected as a significant phenomenon even when the BOLD response occurs. Furthermore, during the task concentration time, since other portions in the brain are activated, the blood flow in the frontal lobe is probably lost (referred to as a steal phenomenon). Alternatively, various other factors can be considered, for example, breathing and cardiac beat are stabilized during concentration, and the blood flow in the skin surface of the frontal lobe decreases by more than change in the blood flow of the brain itself. As a result, the decrease is measured as decrease in the blood flow as a whole.

In the current NIRS, it is difficult to measure and analyze each of these phenomena. The phenomena are detected only as a combined result. The inventors obtained at least an outcome in that the brain blood flow volume decreases during the task concentration time based on the result of experiment. Thus, Embodiment 1 describes a method for measuring a degree of concentration based on decrease in a brain blood flow volume.

Furthermore, Embodiment 1 describes a method for determining a degree of concentration based on decrease in the oxygenated hemoglobin. Generally, it is known that increase or decrease in the total hemoglobin is strongly correlated with increase or decrease in the oxygenated hemoglobin, and the similar result was obtained in the experiment. Since a method for determining a degree of concentration based on increase or decrease in the total hemoglobin is identical to the method for determining a degree of concentration based on decrease in the oxygenated hemoglobin, the description thereof is omitted. Furthermore, the characteristic tendency of increase or decrease in the deoxygenated hemoglobin during the concentrated task time was not able to be obtained in the experiment.

The varying threshold obtaining unit 102 obtains a varying threshold that is a value smaller than a brain blood flow volume of the user at a base time. Specifically, the varying threshold obtaining unit 102 calculates a varying threshold of each user based on increase or decrease in a brain blood flow volume at a rest time. FIG. 3 indicates that the amount of change in the brain blood flow volume at the rest times is constant compared to that during the concentration, but slightly increases or decreases. Furthermore, the fluctuation range of the brain blood flow volume at the rest times sometimes differs for each user and situation. Thus, the varying threshold obtaining unit 102 calculates a varying threshold based on increase or decrease in a brain blood flow volume at a rest time. The varying threshold obtaining unit 102 calculates the maximum value of an absolute value of the amount of change in a brain blood flow at the rest time, and determines a value obtained by adding a minus sign to the maximum value, as a varying threshold. This calculation is for determining a case where the blood flow decreases by more than the maximum width of increase or decrease in a brain blood flow volume at a rest time, as a response of the user. Here, the varying threshold may be the minimum value of the amount of change in the brain blood flow, instead of the value obtained by adding the minus sign to the maximum value of the absolute value of the amount of change in the brain blood flow.

Figure 6:
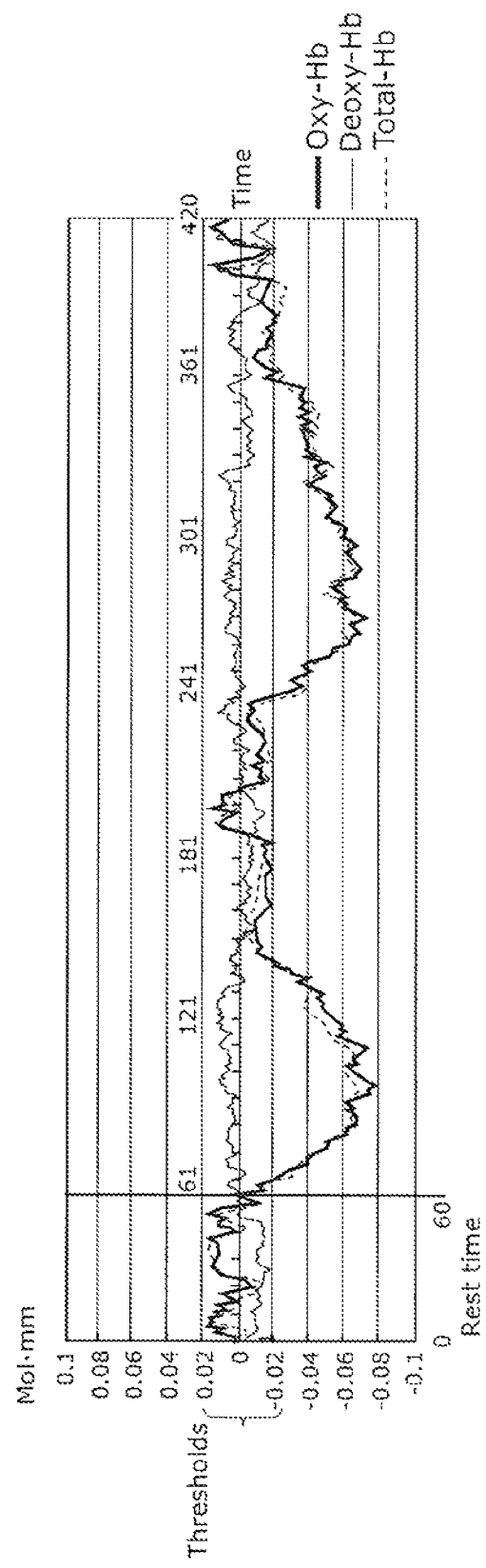
FIG. 6 is a graph for describing a method for calculating a varying threshold.

FIG. 6 is a graph for describing a method for calculating a varying threshold. The data in FIG. 6 is identical to that in FIG. 3. According to Embodiment 1, a rest time continues for 60 seconds from start of the measurement. During the period, a subject remained at rest while the eyes were kept open. The varying threshold obtaining unit 102 receives measured values from the start of 0 second to 60 seconds during the rest time, and calculates the maximum value of an absolute value of the oxygenated hemoglobin. According to Embodiment 1, the maximum value of the absolute value is 0.02 Mol×mm after 40 seconds from start of the measurement, and the varying threshold obtaining unit 102 calculates −0.02 Mol×mm as a varying threshold based on the maximum value. The varying threshold obtaining unit 102 may obtain a varying threshold outside of the concentration presence/absence determining device 110.

The determining unit 130 determines that the user concentrates when the brain blood flow volume obtained by the brain blood flow volume obtaining unit 101 falls below the varying threshold obtained by the varying threshold obtaining unit 102. The determining unit 130 may calculate a concentration section indicating a section in which the user concentrates and a degree of concentration indicating a degree at which the user concentrates, instead of presence or absence of the concentration. The specific example will be described below.

The determining unit 130 includes a decrease start time calculating unit 103, a recovery time calculating unit 104, an increase start time calculating unit 105, a concentration section calculating unit 106, and a degree-of-concentration calculating unit 107 as illustrated in FIG. 1.

The decrease start time calculating unit 103 calculates a time at which a brain blood flow volume falls below a varying threshold, as a decrease start time. In other words, the decrease start time calculating unit 103 calculates a time at which the amount of oxygenated hemoglobin starts to fall below the varying threshold calculated by the varying threshold obtaining unit 102, as a decrease start time.

The recovery time calculating unit 104 calculates a time at which the brain blood flow volume exceeds the varying threshold as a recovery time, after the decrease start time calculated by the decrease start time calculating unit 103. In other words, the recovery time calculating unit 104 calculates, as a recovery time, a time at which the amount of oxygenated hemoglobin starts to exceed the varying threshold calculated by the varying threshold obtaining unit 102 after the decrease start time.

Figure 7:
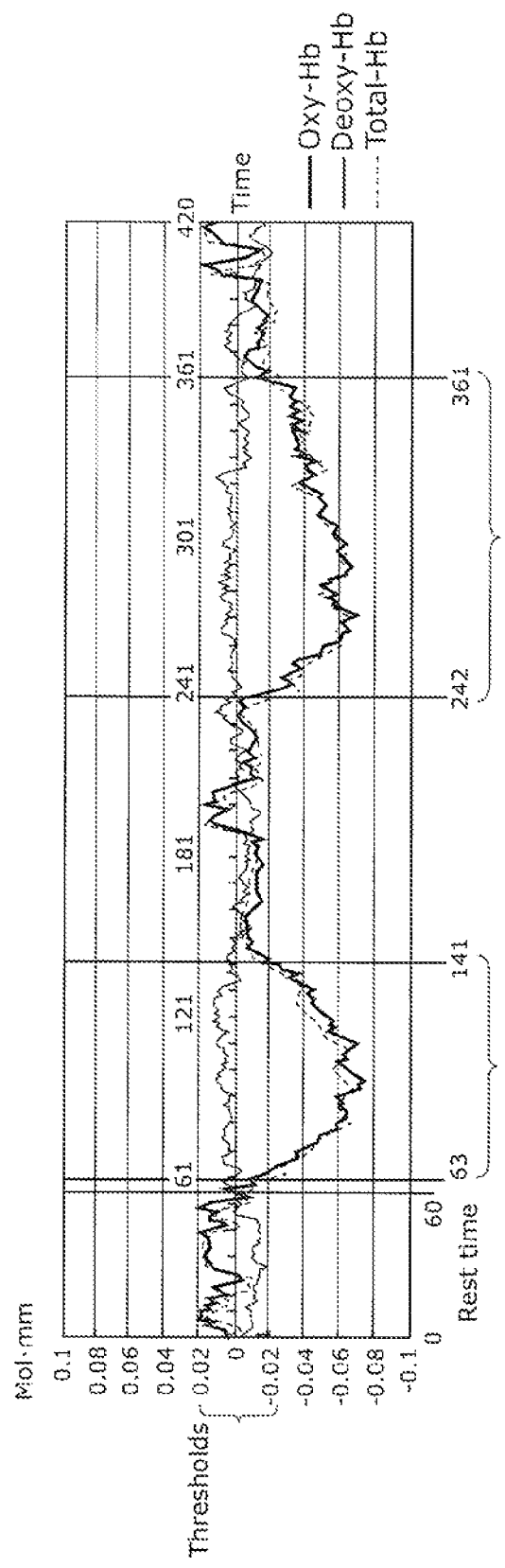
FIG. 7 is a graph for describing a method for calculating a decrease start time and a recovery time.

FIG. 7 is a graph for describing a method for calculating a decrease start time and a recovery time. The varying threshold obtaining unit 102 calculates a varying threshold as −0.02 Mol×mm. The decrease start time calculating unit 103 calculates a time at which the blood flow falls below −0.02 Mol×mm. In FIG. 7, the amount of oxygenated hemoglobin falls below 0.02 Mol×mm at 63 seconds. Thus, the decrease start time calculating unit 103 calculates 63 seconds as a decrease start time.

Next, the recovery time calculating unit 104 calculates, as a recovery time, a time at which the amount of oxygenated hemoglobin exceeds the varying threshold of −0.02 Mol 3×mm after the decrease start time. In FIG. 7, the amount of oxygenated hemoglobin exceeds −0.02 Mol×mm at 141 seconds, Thus, the recovery time calculating unit 104 calculates 141 seconds as a recovery time.

The increase start time calculating unit 105 calculates, as an increase start time at which the brain blood flow volume starts to increase, between the decrease start time calculated by the decrease start time calculating unit 103 and the recovery time calculated by the recovery time calculating unit 104, In other words, the increase start time calculating unit 105 calculates the increase start time at which the brain blood flow volume starts to increase again after the amount of oxygenated hemoglobin decreases. For example, the increase start time calculating unit 105 calculates a slope of temporal change in the brain blood flow volume by extending back from the recovery time, and calculates a time at which the slope falls below a predetermined threshold, as an increase start time. The slope is positive when the brain blood flow volume increases, the slope is negative when the brain blood flow volume decreases, and the slope is equal to 0 when the brain blood flow volume is constant. Thus, the increase start time calculating unit 105 calculates the slope by extending back from the recovery time. Since the slope larger than or equal to a predetermined threshold (for example, 0) indicates that the brain blood flow volume increases, the increase start time calculating unit 105 continues to calculate the slope by further extending back from the time to identify a time at which the slope is smaller than or equal to the predetermined threshold for the first time. Since the brain blood flow volume decreases or becomes constant at the identified time, the increase start time calculating unit 105 calculates the identified time as the first increase start time, that is, as an increase start time.

Figure 8:
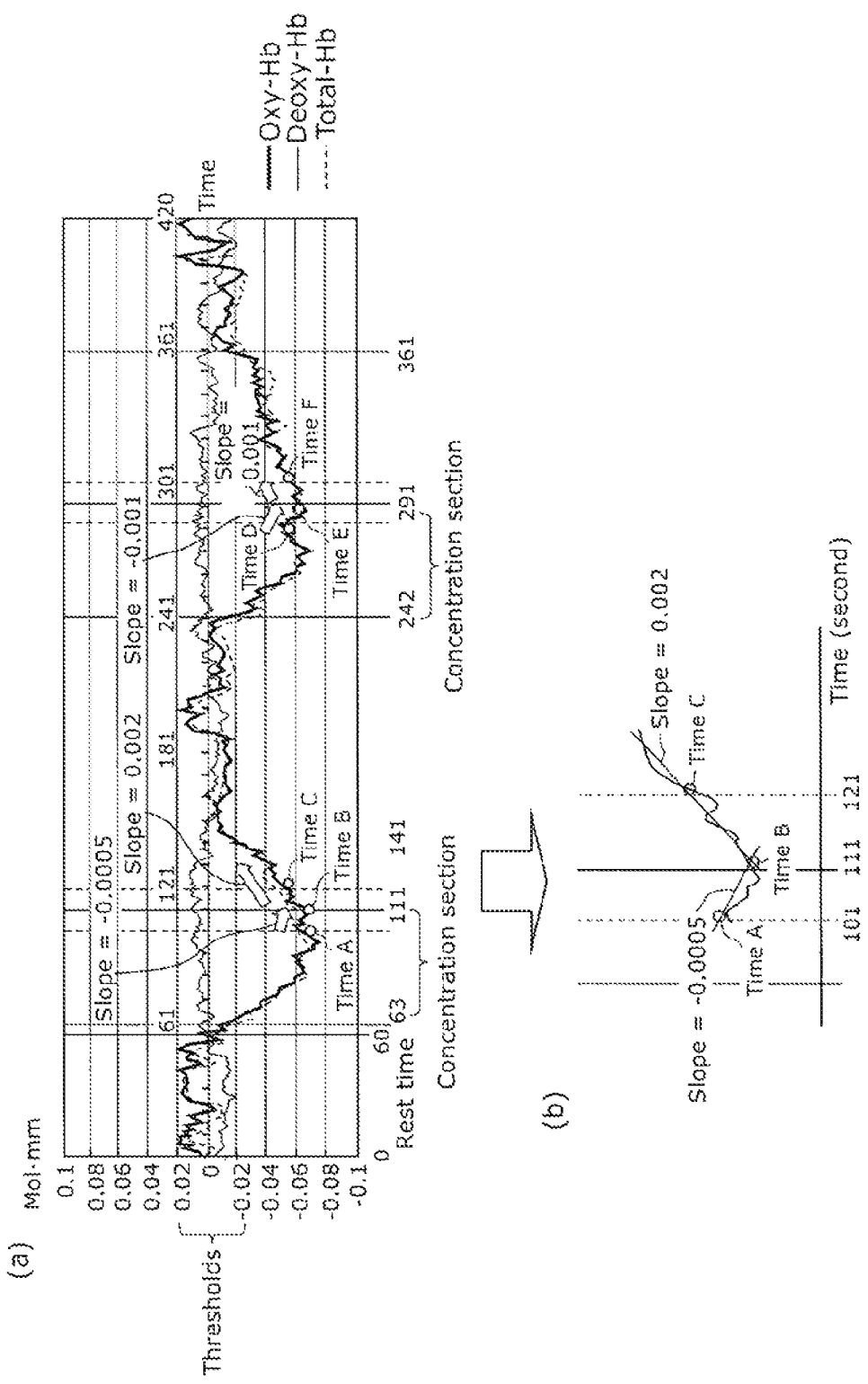
FIG. 8 is a graph for describing a method for calculating an increase start time.

The specific example will be described below. FIG. 8 is a graph for describing a method for calculating an increase start time. In FIG. 8, (a) is a graph indicating change in the brain blood flow volume, and (b) is a part of the graph. First, the recovery time calculating unit 104 calculates the recovery time as 141 seconds. The increase start time calculating unit 105 calculates a slope of change in the brain blood flow volume, with reference to the brain blood flow volume at a time earlier than the recovery time by a predetermined time (for example, 131 seconds that is 10 seconds earlier than 141 seconds). The slope at 131 seconds is positive. Then, the increase start time calculating unit 105 calculates a slope, using the brain blood flow volume at 131 seconds referred to next, and the brain blood flow volume at 121 seconds that is 10 seconds earlier than 131 seconds, Since the brain blood flow volume increases at 121 seconds and further at 111 seconds according to Embodiment 1, the slope is still positive. Thus, the increase start time calculating unit 105 calculates the increase start time by further extending back from the time. The method for calculating an increase start time will be described with reference to (b) of FIG. 8. The brain blood flow volume increases from 111 seconds to 121 seconds, and the increase start time calculating unit 105 calculates the slope as 0.002. Next, the increase start time calculating unit 105 calculates, as −0.0005, a slope of the brain blood flow volume between 101 seconds that is 10 seconds earlier than 111 seconds and 111 seconds because of decrease in the brain blood flow volume, which indicates that the slope falls below the threshold (assumed to be 0). Specifically, the brain blood flow volume decreases or is constant up to 101 seconds, and starts to increase at 111 seconds. Thus, the increase start time calculating unit 105 calculates the increase start time as 111 seconds.

The brain blood flow volume is extended back from the recovery time in order to detect a time at which the user finally starts to lack the concentration. Furthermore, although the blood flow is smaller than or equal to a varying threshold before the recovery time, there is a time-lag between the concentration and the recovery in the blood flow. Thus, the brain blood flow volume is extended back from the recovery time. Furthermore, as seen from FIG. 8, the brain blood flow volume has slight increase or decrease and fluctuations due to noise, a physiological phenomenon, and others. Thus, even when the user concentrates, the brain blood flow volume does not always decrease or is constant. There are cases where the brain blood flow volume sometimes temporarily tends to increase. Thus, calculation of a time at which the brain blood flow volume finally starts to increase by extending back from the recovery time at which the blood flow recovers over the varying threshold results in calculation of the time at which the user finally has no concentration with accuracy.

Furthermore, a period during which the brain blood flow volume is referred to have predetermined intervals, such as 10 seconds, to calculate a slope according to Embodiment 1. This is because increase or decrease and fluctuations in the brain blood flow volume caused by noise, a physiological phenomenon, and others are considered. In other words, increase or decrease in a slope for a short period of time, such as 1 second, is more frequently switched, and it is difficult to calculate an increase start time with accuracy. On the other hand, it is possible to calculate an increase start time with accuracy by calculating a slope at predetermined intervals.

Embodiment 1 assumes that a predetermined threshold is 0 and that a time at which a slope of temporal change in the brain blood flow volume is larger than or equal to the predetermined threshold by extending back from the recovery time, that is, a time at which the slope starts to be positive, is an increase start time. However, the predetermined threshold is not limited to these. For example, a threshold of a slope may be set based on a varying threshold indicating fluctuations at a rest time. The fluctuations at a rest time differs for each individual. During the same rest time, there are two types of subjects: subjects having larger fluctuations and having smaller fluctuations in the brain blood flow. The subjects having larger fluctuations at a rest time have possibilities of having larger fluctuations in the brain blood flow volume, such as decrease during the concentration, a constant state, and increase in recovery. Thus, the threshold of the slope may be calculated in consideration of a varying threshold at a rest time. For example, assume 0.02 as a varying threshold at a rest time. Furthermore, assume that the reference times are at intervals of 10 seconds as described above. In this case, the threshold of a slope is calculated by 0.02÷10=0.002. The slope larger than this threshold indicates that the subject is during the recovery, and the increase start time is searched by extending back from the recovery time.

Furthermore, the threshold of the slope may be calculated using fluctuations not at a rest time but during concentration. There is a possibility of a subject whose fluctuations at a rest time are not always identical to those during concentration. For example, there is a possibility of a subject whose fluctuations at a rest time are larger but fluctuations during concentration are smaller, or conversely, whose fluctuations at a rest time are smaller but fluctuations during concentration are larger. In such a case, a concentration section cannot be always calculated with accuracy using a varying threshold only at a rest time. Thus, a concentration task may be assigned to each subject in advance, and a threshold of a slope may be calculated based on fluctuations when the subject was concentrating during the task time.

Calculation of an increase start time according to Embodiment 1 is an example, and the calculation is not limited to this. For example, noise that increases for a short period of time may be removed by applying a low-pass filter to a blood flow volume or smoothing the blood flow volume. Furthermore, a differential coefficient of a blood flow volume may be calculated, and an extreme value at which the differential coefficient is equal to 0 may be calculated as an increase start time.

The concentration section calculating unit 106 identifies a concentration section based on change in an amount of oxygenated hemoglobin. Specifically, the concentration section calculating unit 106 calculates, as a concentration section that is a period in which the user concentrates, a period from the decrease start time calculated by the decrease start time calculating unit 103 to the increase start time calculated by the increase start time calculating unit 105. In the data indicated by (a) of FIG. 8, a section from 63 seconds that is a decrease start time to 111 seconds that is an increase start time is calculated as one concentration section.

The concentration section calculating unit 106 may calculate a plurality of concentration sections from target data (time), in accordance with the procedure described above. The calculation will be described with reference to FIGS. 7 and 8 again. In FIG. 7, the amount of oxygenated hemoglobin at 242 seconds other than 63 seconds is indicated by a value smaller than or equal to the varying threshold, and 242 seconds is also calculated as a decrease start time. The value decreases for a short period of time, and the concentration section calculating unit 106 calculates 361 seconds as a recovery time at which the blood flow recovers over the varying threshold again. Furthermore, as indicated by (a) of FIG. 8, the increase start time calculating unit 105 calculates 291 seconds at which the slope is changed from −0.001 to 0.001, as an increase start time. Then, the concentration section calculating unit 106 calculates a period between 242 seconds and 291 seconds as a concentration section.

The degree-of-concentration calculating unit 107 determines a degree of concentration, based on a time length of a concentration section within a target section and a frequency of a concentration section. For example, the degree-of-concentration calculating unit 107 calculates a degree of concentration at a ratio of a time length of a concentration section to a time length of a target section. The target section indicates a period during which the user performs a task. In other words, the degree-of-concentration calculating unit 107 calculates a ratio of a concentration section calculated by the concentration section calculating unit 106 to a target section, as a degree of concentration of the user.

In FIGS. 7 and 8, it is understood that the period during which the task of listening to the English news was actually performed was 120 seconds that is a total of (i) 60 seconds from 60 seconds to 120 seconds and (ii) 60 seconds from 240 seconds to 300 seconds. Furthermore, the calculated concentration section was 97 seconds that is a total of (i) 48 seconds from 63 seconds to 111 seconds and (ii) 49 seconds from 242 seconds to 291 seconds. Thus, the degree of concentration is calculated as 81% (=97 120×100).

Figure 9:
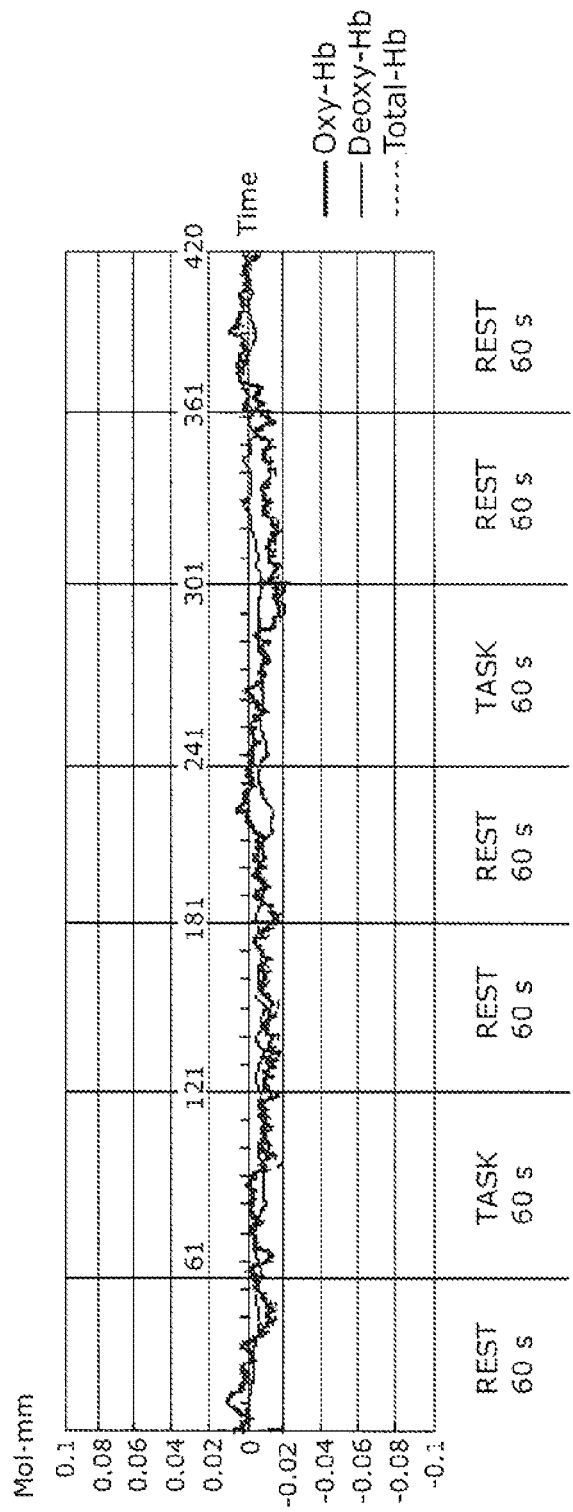
FIG. 9 is a graph indicating determination of a degree of concentration.

FIG. 9 is a graph for describing determination of a degree of concentration. FIG. 9 illustrates a result of an experiment in which the same task indicated in FIG. 3 was performed on the same subject. In FIG. 9, the subject was instructed not to concentrate on listening to the English news, and was set to a pseudo-concentration-lacking state. Compared to FIG. 3, FIG. 9 indicates no decreasing tendency in a brain blood flow volume even during the task times. When the concentration section is calculated using the aforementioned method, any section in which the amount of oxygenated hemoglobin decreases to be smaller than or equal to the varying threshold is not calculated, and thus, the concentration section is 0 second in the data of FIG. 9. Since the concentration section is 0 second against the task times of 120 seconds that is the total of (i) 60 seconds from 60 seconds to 120 seconds and (ii) 60 seconds from 240 seconds to 300 seconds, the degree of concentration is 0% (=0/120×100).

Using the method according to Embodiment 1, a degree of concentration of the user can be determined based on the decreasing tendency of the brain blood flow volume.

Figure 10:
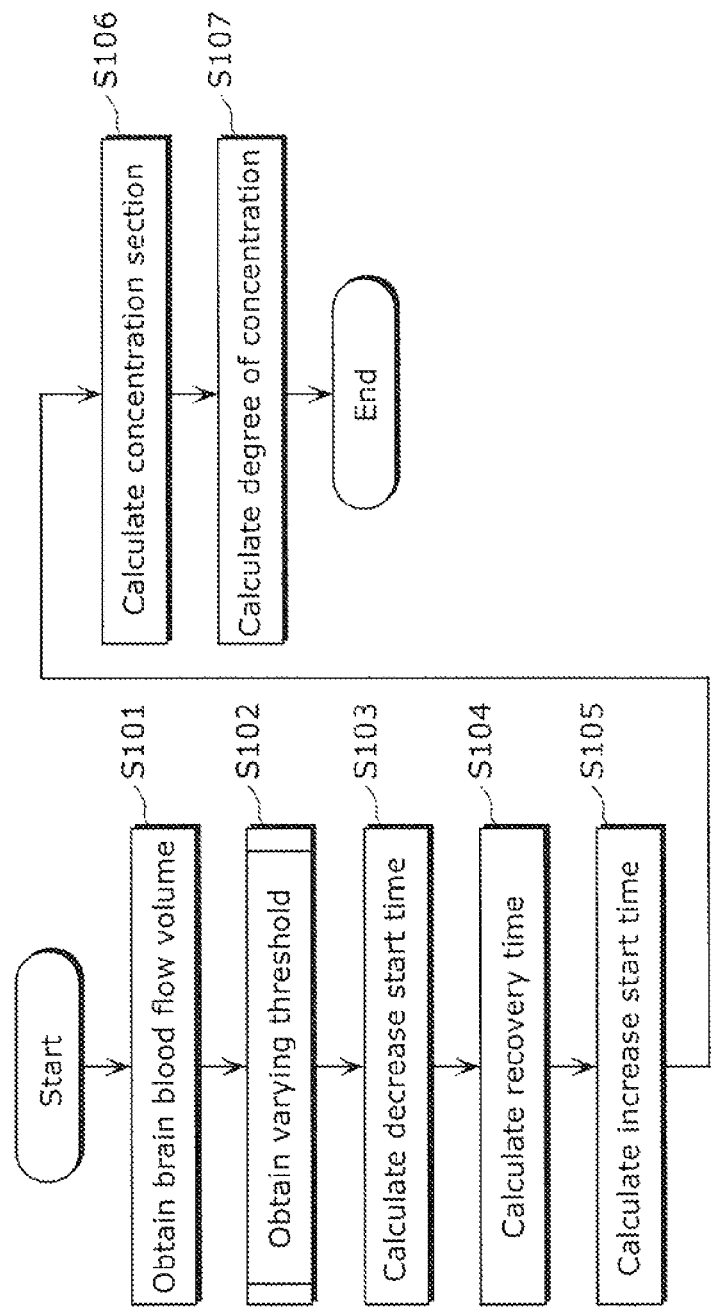
FIG. 10 is a flowchart indicating processes performed by the concentration presence/absence determining device according to Embodiment 1.

The procedure according to Embodiment 1 will be described with reference to flowcharts of FIGS. 10 to 12.

The brain blood flow volume obtaining unit 101 obtains a brain blood flow volume of the user (Step S101). The varying threshold obtaining unit 102 calculates a varying threshold based on the obtained brain blood flow volume (Step S102).

Figure 11:
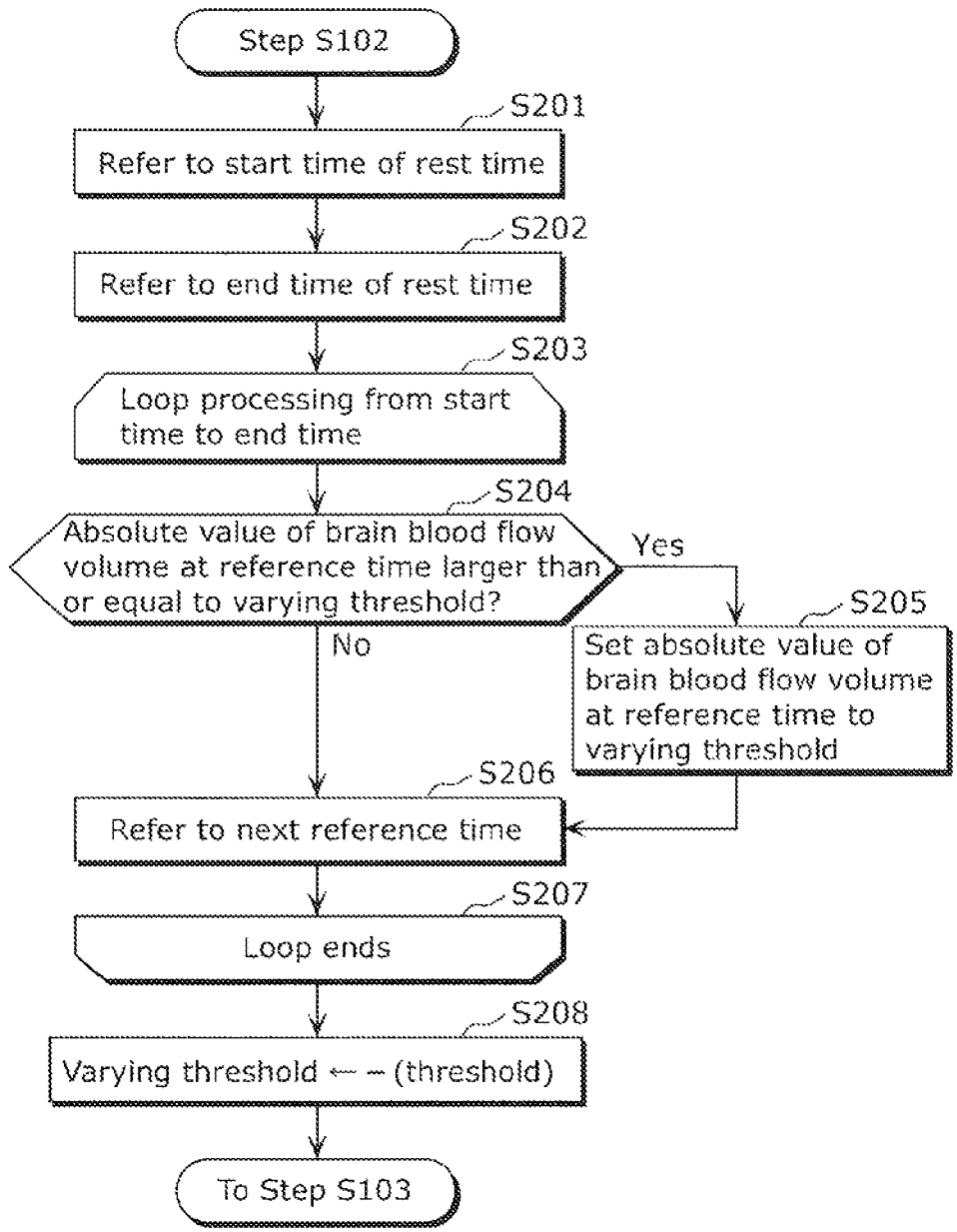
FIG. 11 is a detailed flowchart of the process of obtaining a varying threshold (Step S102 in FIG. 10).

FIG. 11 is a flowchart indicating the details of Step S102. In order to calculate the varying threshold, assume, for example, using a brain blood flow volume at a rest time. The varying threshold obtaining unit 102 refers to a start time of the rest time (Step S201), and an end time of the rest time (Step S202). When the brain blood flow volume obtaining unit 101 obtains the brain blood flow volume, the user or a measurement observer may input the start time and the end time of the rest time. The loop processing is performed by increasing a reference time between a start time and an end time that have been referred to (Steps S203 to S207). The varying threshold obtaining unit 102 determines whether or not an absolute value of a brain blood flow volume at the reference time is larger than or equal to a varying threshold (initial value is 0) (Step S204). When the absolute value of the brain blood flow volume is larger than or equal to the varying threshold (Yes at Step S204), the varying threshold obtaining unit 102 sets the absolute value of the brain blood flow volume at the reference time to the varying threshold (Step S205), and refers to the next reference time (Step S206). When the absolute value of the brain blood flow volume at the reference time is smaller than the varying threshold (No at Step S204), the varying threshold obtaining unit 102 refers to the next reference time (Step S206), With repetition of the loop processing from the start time to the end time, the maximum value of the absolute value in the section is set to the varying threshold. The varying threshold obtaining unit 102 calculates a value obtained by adding a minus sign to the set varying threshold, as a varying threshold (Step S208).

Again with reference to FIG. 10, the decrease start time calculating unit 103 calculates a decrease start time (Step S103). Next, the recovery time calculating unit 104 calculates a recovery time (Step S104), Then, the increase start time calculating unit 105 calculates an increase start time at which the brain blood flow volume finally starts to increase by extending back from the recovery time (Step S105).

Figure 12:
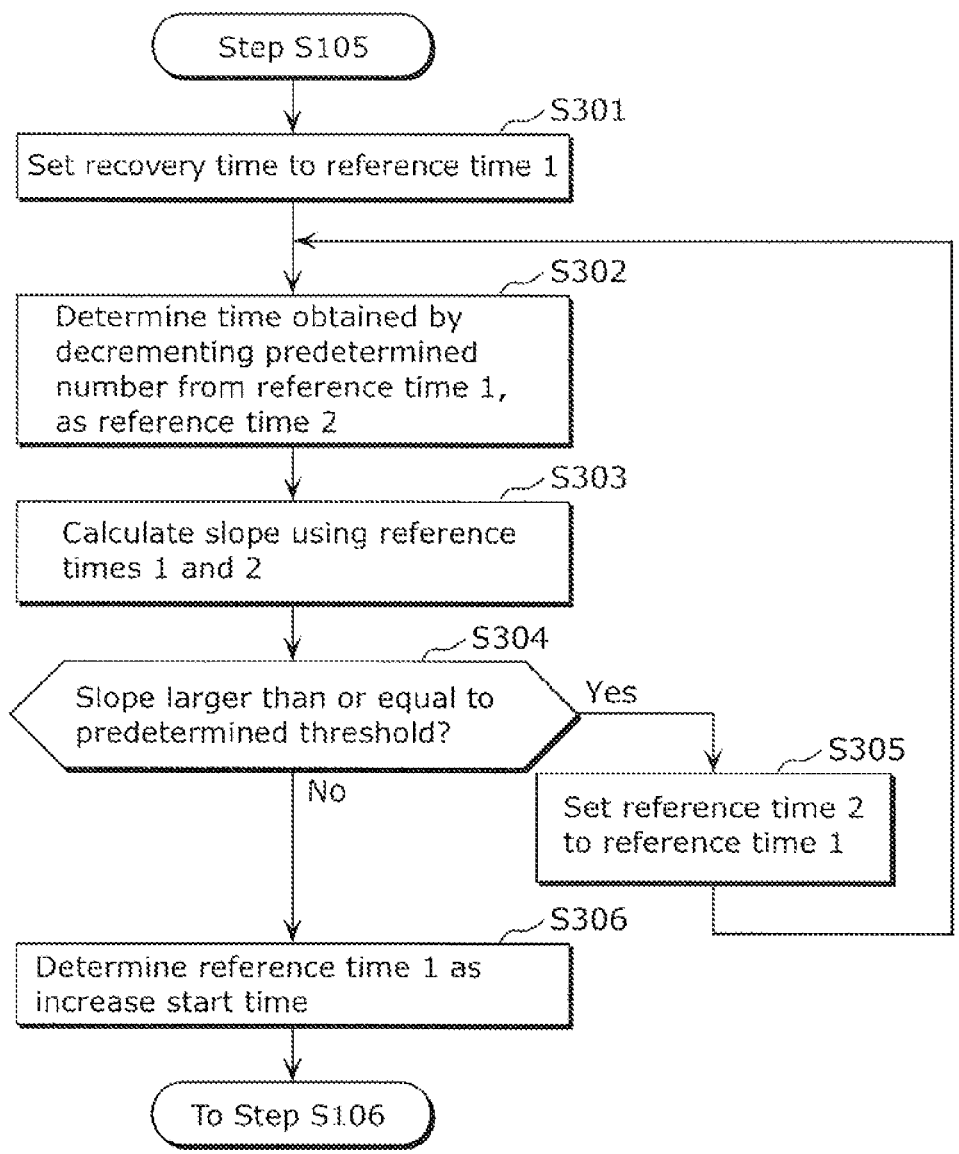
FIG. 12 is a detailed flowchart of the process of calculating an increase start time (Step S105 in FIG. 10).

FIG. 12 is a flowchart indicating the details of Step S105. The increase start time calculating unit 105 sets the recovery time to a reference time 1 (Step S301). The increase start time calculating unit 105 determines a time obtained by decrementing a predetermined number (for example, 10 seconds) from the reference time 1, as a reference time 2 (Step S302), The increase start time calculating unit 105 calculates a slope using the reference times 1 and 2 (Step S303). The increase start time calculating unit 105 determines whether or not the calculated slope is larger than or equal to a predetermined threshold (for example, 0) (Step S304), When the slope is larger than or equal to the predetermined threshold (Yes at Step S304), the increase start time calculating unit 105 sets the current reference time 2 to the reference time 1 (Step S305), and the processes return to Step S302. When the slope is smaller than the predetermined threshold (No at Step S304), the increase start time calculating unit 105 determines the reference time 1 as an increase start time (Step S306).

Since the slope larger than or equal to the predetermined threshold indicates increase in the brain blood flow volume, the processes from Step S302 to Step S305 are repeated. During increase in the brain blood flow volume, the reference times are extended back. When the slope is smaller than the threshold, the brain blood flow volume reaches a time at which the reference time 1 starts to increase, and consequently, the increase start time is calculated.

Again with reference to FIG. 10, the concentration section calculating unit 106 calculates a concentration section (Step S106), The concentration section calculating unit 106 calculates, as a concentration section, a period from the decrease start time calculated at Step S103 to the increase start time calculated at Step S105.

The degree-of-concentration calculating unit 107 calculates a degree of concentration (Step S107). For example, the degree-of-concentration calculating unit 107 calculates a degree of concentration by calculating a ratio of a concentration section to a target section input in advance by the user or the measurement observer as described above.

Although a degree of concentration is determined based on a ratio of a concentration section to a target section for a task according to Embodiment 1, the calculation is not limited to such. For example, the degree of concentration may be calculated in consideration of the decreasing amplitude in a brain blood flow volume. The specific example will be described below.

Figure 13:
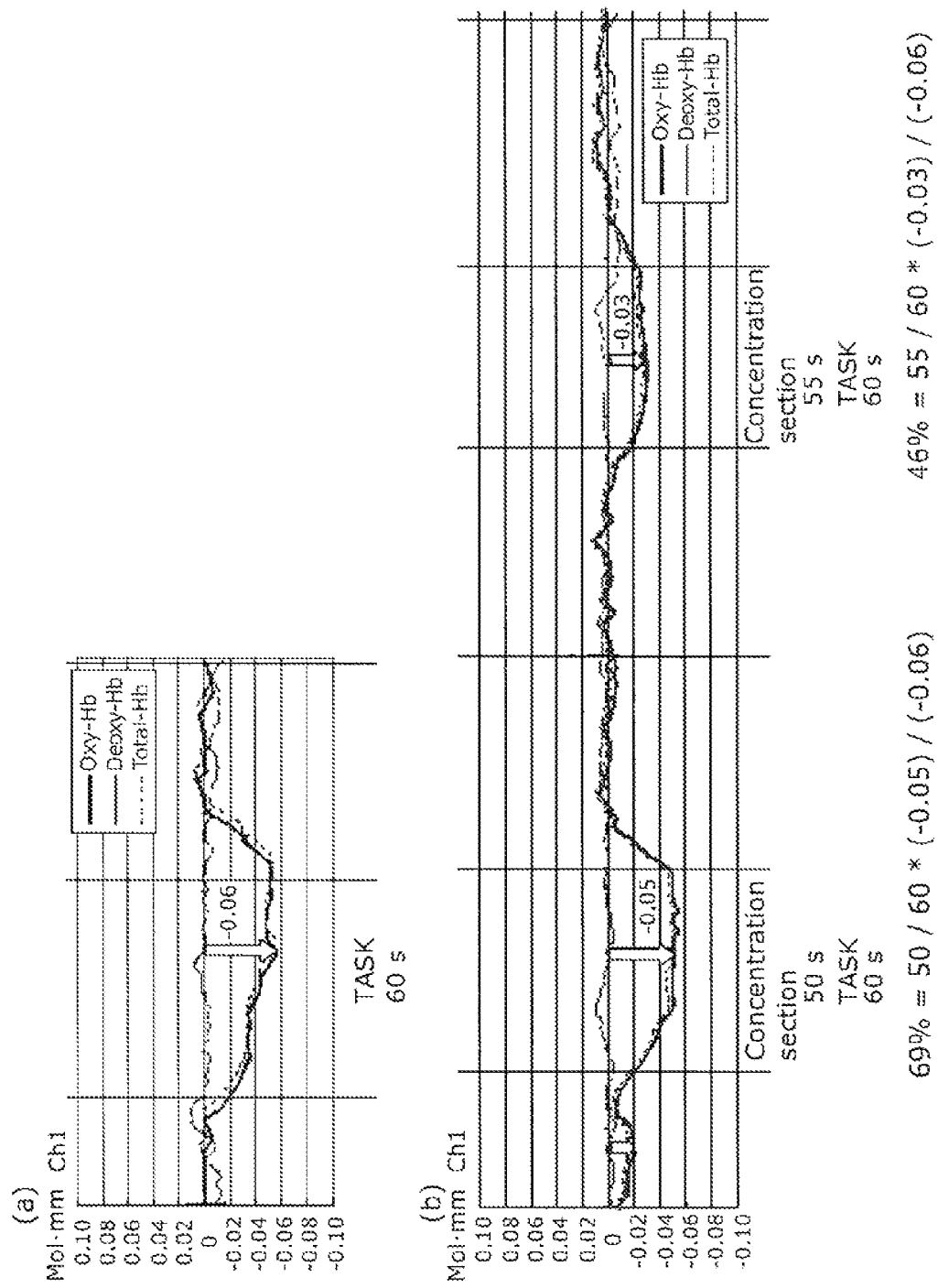
FIG. 13 indicates graphs for describing a method for determining a degree of concentration.

FIG. 13 indicates graphs for describing a method for determining a degree of concentration. FIG. 13 indicates data of change in a brain blood flow volume of a subject whose task was listening to English news as similar to the experiment data in FIG. 7. The thick line indicates an amount of oxygenated hemoglobin (oxy-Hb) the thin line indicates an amount of deoxygenated hemoglobin (deoxy-Hb), and the thin dotted line indicates an amount of total hemoglobin (total-Hb). How to see the graph is the same as that in FIG. 3. (a) in FIG. 13 is actual data when the task was performed once, and (b) in FIG. 13 is actual data when the task was performed twice.

(a) in FIG. 13 clarifies decrease in the brain blood flow volume during the task time, Assume that the task is given for 60 seconds, and the concentration section calculating unit 106 calculates a concentration section as 60 seconds. The minimum value of the brain blood flow volume in the concentration section is −0.06. The degree-of-concentration calculating unit 107 calculates a degree of concentration in consideration of a ratio of an amplitude expressed by the minimum value in performing the current task to an amplitude in performing another task.

(b) in FIG. 13 indicates data when a subject was listening to English news for the second time. The task was performed consecutively twice with a rest between the tasks. In (b) in FIG. 13, the concentration section is calculated as 50 seconds during the initial task for 60 seconds. Furthermore, the minimum value of the brain blood flow volume in the concentration section is −0.05, and a amplitude ratio is 5/6 (=−0.05/−0.06). Thus, the degree of concentration for the first time is calculated in consideration of the concentration section and the amplitude ratio as follows. Specifically, the degree-of-concentration calculating unit 107 calculates a corrected degree of concentration as 69% (=50/60×100×5/6) by multiplying the degree of concentration by the amplitude ratio.

Furthermore, during the second task in (b) of FIG. 13, the concentration section is 55 seconds, and the minimum value of the brain blood flow volume in the concentration section is −0.03. Furthermore, an amplitude ratio to the minimum value of the base brain blood flow volume is 1/2(=−0.03/−0.06). Thus, the degree-of-concentration calculating unit 107 calculates a degree of concentration during the second task as 46% (=55/60×100×1/2).

Since the brain blood flow volume measured by the NIRS sensor such as the brain blood flow volume obtaining unit 101 according to Embodiment 1 is not an absolute value but a relative change amount from the brain blood flow volume at a base time, comparison between values as they are does not strictly mean anything. However, degrees of concentration for each task time can be compared by calculating a brain blood flow volume while performing a base task, and correcting a degree of concentration using a ratio of a brain blood flow volume to the base brain blood flow volume, that is, normalizing the degree of concentration.

For example, the user has boredom and fatigue and is lacking in concentration by repeatedly performing the same task. During decrease in the concentration, the decreasing tendency of the brain blood flow volume sometimes does not occur, or the reduction width of the brain blood flow volume is sometimes narrowed down. Thus, as indicated by the method according to Embodiment 1, a decreasing amplitude of a base concentration section, such as the first concentration section, is set to a base amplitude, and a degree of concentration can be compared with a base degree of concentration using an amplitude ratio with respect to the base amplitude.

Furthermore, the tendency of degrees of concentration for each subject may be determined in consideration of increase or decrease in degree of concentration for each task time. For example, the tendency of degrees of concentration for each subject can be clarified, such as a subject who cannot increase a degree of concentration even when a task is performed many times, a subject whose degree of concentration decreases as the number of task times, and a subject whose concentration is spread for each task time.

Although the amplitude is used in the aforementioned examples, the degree of concentration may be calculated using an area corresponding to a decrease amount of the brain blood flow volume. In other words, an absolute value of an integrated value of brain blood flow volumes from the decrease start time of a concentration section to a time at which the brain blood flow volume is minimized may be used instead of the amplitude.

Figure 14:
FIG. 14 indicates graphs for describing a method for determining a degree of concentration.

Furthermore, a time length of a concentration section and a frequency of a concentration section may be considered. FIG. 14 indicates graphs for describing a method for determining a degree of concentration.

In FIG. 14, each of (a) and (b) indicates data of change in a brain blood flow volume when a subject was given a task of reading English. The thick line indicates an amount of oxygenated hemoglobin (oxy-Hb), the thin line indicates an amount of deoxygenated hemoglobin (deoxy-Hb), and the thin dotted line indicates an amount of total hemoglobin (total-Hb). How to see the graphs is the same as that in FIG. 3. REST in which the user was at rest continued for 120 seconds, and then, the user was given a task of reading English for 300 seconds.

In FIG. 14, (a) indicates that the brain blood flow volume decreases after starting the task, and 220 seconds are calculated as a concentration section within 300 seconds that is a target section of the task. In contrast, (b) indicates that the brain blood flow volume decreases after starting the task but increases later, and 50 seconds are calculated as the first concentration section. Then, the brain blood flow volume again decreases, and the next concentration section for 65 seconds and the concentration section after the next for 60 seconds are calculated as the total three concentration sections if combined with the first concentration section.

Thus, even during the target section in which the same task is performed (300 seconds), the decreasing tendency in the brain blood flow volume differs for each individual or depending on a way to concentrate by the same person. This reflects on various cases where the user concentrates for a long period of time and where concentration and rest are repeated for a relatively short period of time. Thus, the degree-of-concentration calculating unit 107 may determine a degree of concentration in consideration of a time length of a concentration section and a frequency of the concentration section. For example, a degree of concentration is not merely expressed by a percent, but an average of frequencies or time lengths of concentration sections may be indicated to the user or the measurement observer as an item of a degree of concentration.

For example, in (a) of FIG. 14, the degree of concentration is calculated as 73% (=220/300×100), where an average of the time length is 220 seconds with one concentration section. In (b) of FIG. 14, the degree of concentration is calculated as 58% (=(50+65+60)/300×100), where an average of the time lengths is 58 seconds (=(50+65+60)/3) with three concentration sections.

When a task given to a subject is desirably concentrated on one concentration section rather than spreading the task into several concentration sections, the degree-of-concentration calculating unit 107 may calculate a degree of concentration using a weight assigned to a frequency of the concentration section. For example, a degree of concentration may be calculated by multiplying a degree of concentration by a predetermined weight that decreases with a higher frequency of a concentration section as indicated in (c) of FIG. 14 during an evaluation time. For example, the weight is set to 1 when the frequency of a concentration section is once, is set to 0.9 when the frequency is twice, and is set to 0.8 when the frequency is three times. In (a) of FIG. 14, the degree of concentration is 73% (=220/300×100×1.0). In (b) of FIG. 14, the degree of concentration is 47% (=(50+65+60)/300×100×0.8).

According to Embodiment 1, when each student reads an English learning material provided, a degree of concentration of the student can be quantitatively measured using the concentration presence/absence determining device 110. Accordingly, the teacher can determine which student lacks a degree of concentration. Although a degree of concentration at which each student was concentrating on study cannot be measured from the viewpoint of the student, quality of the study can be qualitatively measured. When a student has enough time to study but the student performance, etc. is not improved and a degree of concentration of study is low, it is possible to alert the student to increase the degree of concentration. Even so, when the degree of concentration is not improved, the degree of concentration of the student in study is measured by changing the level of the material, which enables provision of efficient advice.

Furthermore, application of the concentration presence/absence determining device according to Embodiment 1 during a test in which the achievement or performance of the study is measured enables qualitative measurement of a degree of concentration to find out whether the student cannot solve a problem after sufficient consideration or due to lacking in the concentration. Thus, not only whether a mark on a test is low or high but also the understanding of a student can be measured, and thus, the data can be later used for providing advice on learning.

As described above, according to Embodiment 1, it is determined that the user concentrates when the brain blood flow volume falls below the varying threshold. Thus, whether or not the user concentrates can be determined with accuracy.

Furthermore, the brain blood flow volume increases when the user is lacking in concentration. Thus, a concentration section that is a period in which the user concentrates can be calculated with accuracy by calculating, as a concentration section, a period from the time when the brain blood flow volume falls below the varying threshold to the time when the brain blood flow volume starts to increase.

(Modification 1)

When the concentration presence/absence determining device is used for the first time, a concentration pattern of a subject may be determined in consideration of an amplitude ratio to a base amplitude, and the length and the frequency of a concentration section. For example, even for the same task, a change tendency in a brain blood flow volume affected by concentration differs for each individual or depending on a day and time in which the individual performs the same task. Thus, the concentration pattern may be determined.

The configuration of the concentration presence/absence determining device 110 according to Modification 1 is the same as that in FIG. 1. However, the processes performed by the degree-of-concentration calculating unit 107 are different. The degree-of-concentration calculating unit 107 determines a concentration pattern of the user by determining which one of concentration patterns is the closest to the change in a brain blood flow volume of the user. The specific example will be described below.

FIGS. 15A to 15D are graphs indicating examples of concentration patterns. The degree-of-concentration calculating unit 107 classifies a pattern of change in a brain blood flow volume into a concentration pattern, based on one of a ratio of a concentration section to a target section, the number of concentration sections within the target section, and a ratio of the minimum value of the first concentration section to the minimum value of the second concentration section within the target section.

Figure 15A:
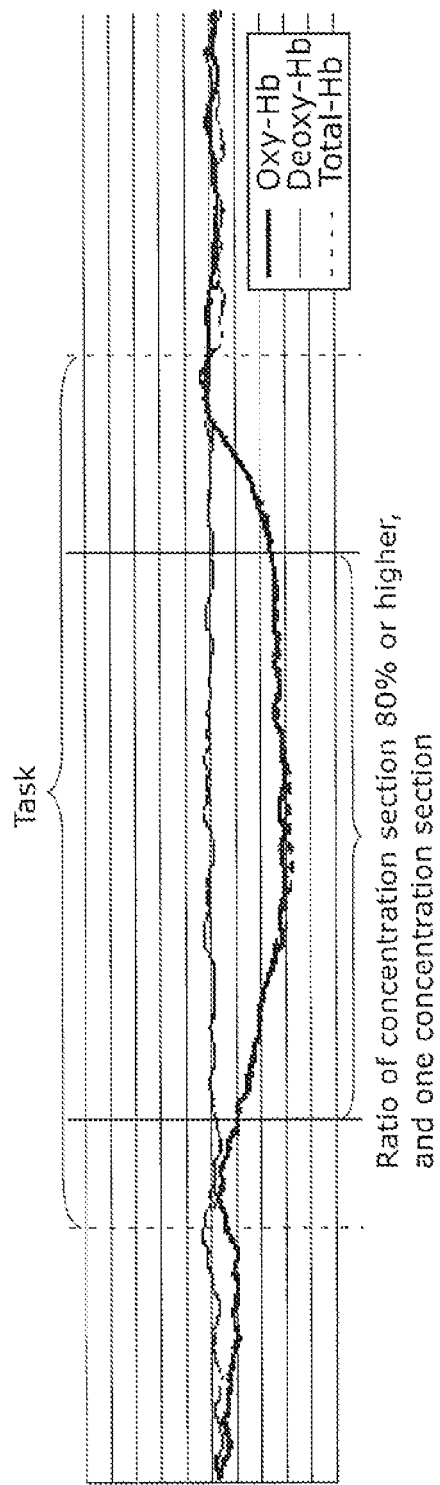
FIG. 15A is a graph indicating an example of concentration pattern.

FIG. 15A is a graph indicating a pattern A in which the ratio of a concentration section is 80% or higher for one task and which is a pattern of change in a brain blood flow volume of the concentration section for the one task. The transition of the brain blood flow volume of the pattern A indicates that the user almost continued to concentrate during the task.

FIG. 15B is a graph indicating a pattern B in which the ratio of a concentration section is lower than 80% for one task and which is a pattern of change in a brain blood flow volume of the concentration section for the one task. The pattern B is a pattern in which the brain blood flow volume decreases during the one task and the concentration section is relatively shorter for the task.

Figure 15C:
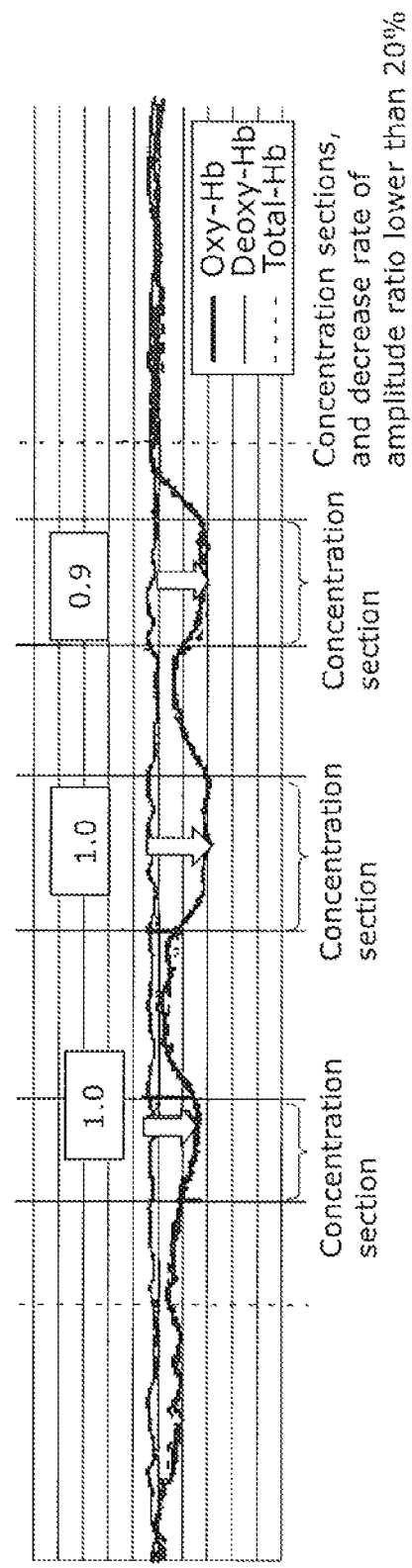
FIG. 15C is a graph indicating an example of a concentration pattern.
Figure 15D:
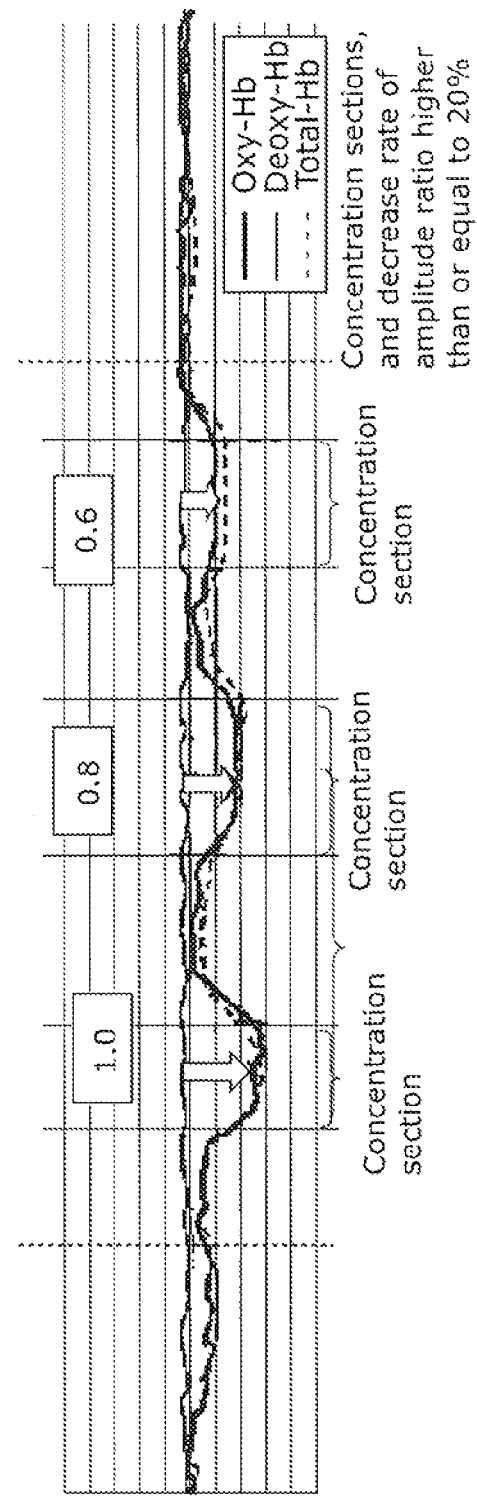
FIG. 15D is a graph indicating an example of a concentration pattern.

The pattern C and the pattern D indicated in FIG. 15C and FIG. 15D, respectively are patterns in which a pair of concentration and rest is repeated for several times for one task and there are concentration sections. Furthermore, when the decreasing amplitude for the first concentration section is represented by 1.0 (value is negative, and thus is represented by an absolute value), the absolute value of amplitude is not relatively reduced. Thus, the decreasing amplitude for the second concentration section is represented by 1.0, and the decreasing amplitude for the third concentration section is represented by 0.9. For example, the absolute value of the first amplitude to that of the third amplitude is decreased by 10% (=(1.0−0.9)/1.0×100). This patter is a pattern in which a concentration section for a short period of time is repeated for one task but a concentration tendency of maintaining a high degree of concentration (reduction width) is reflected.

In contrast, in the pattern D, when the decreasing amplitude for the first concentration section is represented by 1.0, the absolute value of amplitude is reduced. Thus, the decreasing amplitude for the second concentration section is represented by 0.8, and the decreasing amplitude for the third concentration section is represented by 116, For example, the absolute value of the first amplitude to that of the third amplitude is decreased by 40% (=(1.0−0.6)/1.0× 100). This patter is a pattern in which a concentration section for a short period of time is repeated for one task but a concentration tendency of gradual decrease in degree of concentration (decreasing reduction width) is reflected. The degree-of-concentration calculating unit 107 determines a concentration tendency of a subject by matching a pattern of change in a brain blood flow volume of the subject actually measured, with one of these patterns.

In this manner, a concentration tendency of a subject may be determined by calculating a degree of concentration based on concentration sections and amplitudes of the brain blood flow volume and determining a pattern of the concentration sections and the amplitudes. Here, the degree of concentration is determined based on the concentration tendency.

Figure 16:
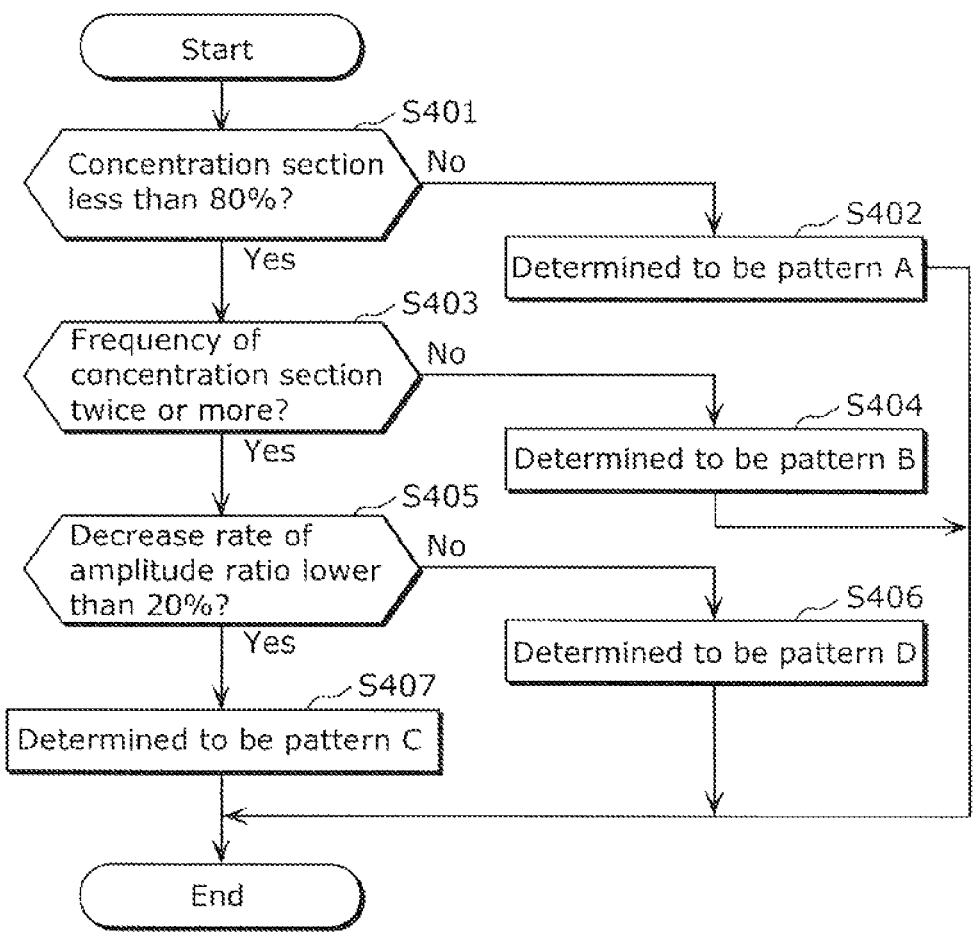
FIG. 16 is a flowchart indicating processes of determining a pattern.

The procedure for determining a pattern will be described with reference to FIG. 16. The processes until calculation of a concentration section are the same as those in FIGS. 10 and 12, and thus, the description thereof is omitted. Here, the pattern matching will be described.

First, the degree-of-concentration calculating unit 107 determines whether or not a concentration section of one task is less than a predetermined threshold (for example, 80%) (Step S401). When the concentration section is greater than or equal to the predetermined threshold (No at Step S401), the degree-of-concentration calculating unit 107 determines the concentration pattern to be the pattern A (Step S402). This is a pattern in which a concentration section is longer and the user concentrated on the task for a relatively longer period. When the concentration section is less than the predetermined threshold (Yes at Step S401), the degree-of-concentration calculating unit 107 determines whether or not the frequency of a concentration section is twice or more (for example, twice) (Step S403). When the frequency of a concentration section is smaller than predetermined times (No at Step S403), the degree-of-concentration calculating unit 107 determines the concentration pattern to be the pattern B in which the concentration section is relatively shorter (Step S404). When the frequency of a concentration section is larger than or equal to the predetermined times (Yes at Step S403), the degree-of-concentration calculating unit 107 determines whether or not a decrease rate of an amplitude ratio is lower than a predetermined threshold (20%) (Step S405). When the decrease rate of an amplitude ratio is higher than or equal to the predetermined threshold (No at Step S405), the degree-of-concentration calculating unit 107 determines the concentration pattern to be the pattern D (Step S406). The pattern D is a pattern in which the user intermittently concentrates and the degree of concentration is decreasing. When the decrease rate of an amplitude ratio is lower than the predetermined threshold (Yes at Step S405), the degree-of-concentration calculating unit 107 determines the concentration pattern to be the pattern C (Step S407). The pattern C is a pattern in which the user intermittently concentrates but the degree of concentration is maintained. In this manner, a concentration tendency of a subject can be determined by determining a pattern of the concentration section and the amplitude of a decreasing brain blood flow volume. For example, during the time when the user is playing a game and the concentration sections are separated, there is no problem of continuing the game for a long time. However, when the user who has a single concentration section is playing the game, the concentration presence/absence determining device may suggest, as an application, having an intermission during the game to the user.

Although the brain blood flow volume obtained by the brain blood flow volume obtaining unit 101 is a brain blood flow volume measured in a predetermined channel according to Modification 1, the brain blood flow volume is not limited to such. As illustrated in FIG. 2, the brain blood flow volume obtaining unit 101 includes a plurality of light receiving units and a plurality of light emitting units, so that a brain blood flow volume can be measured at a plurality of measurement parts. Thus, a channel in which a degree of concentration is determined may be selected with respect to respective brain blood flow volumes at a rest time and when a task is given. The specific example will be described below.

Figure 17:
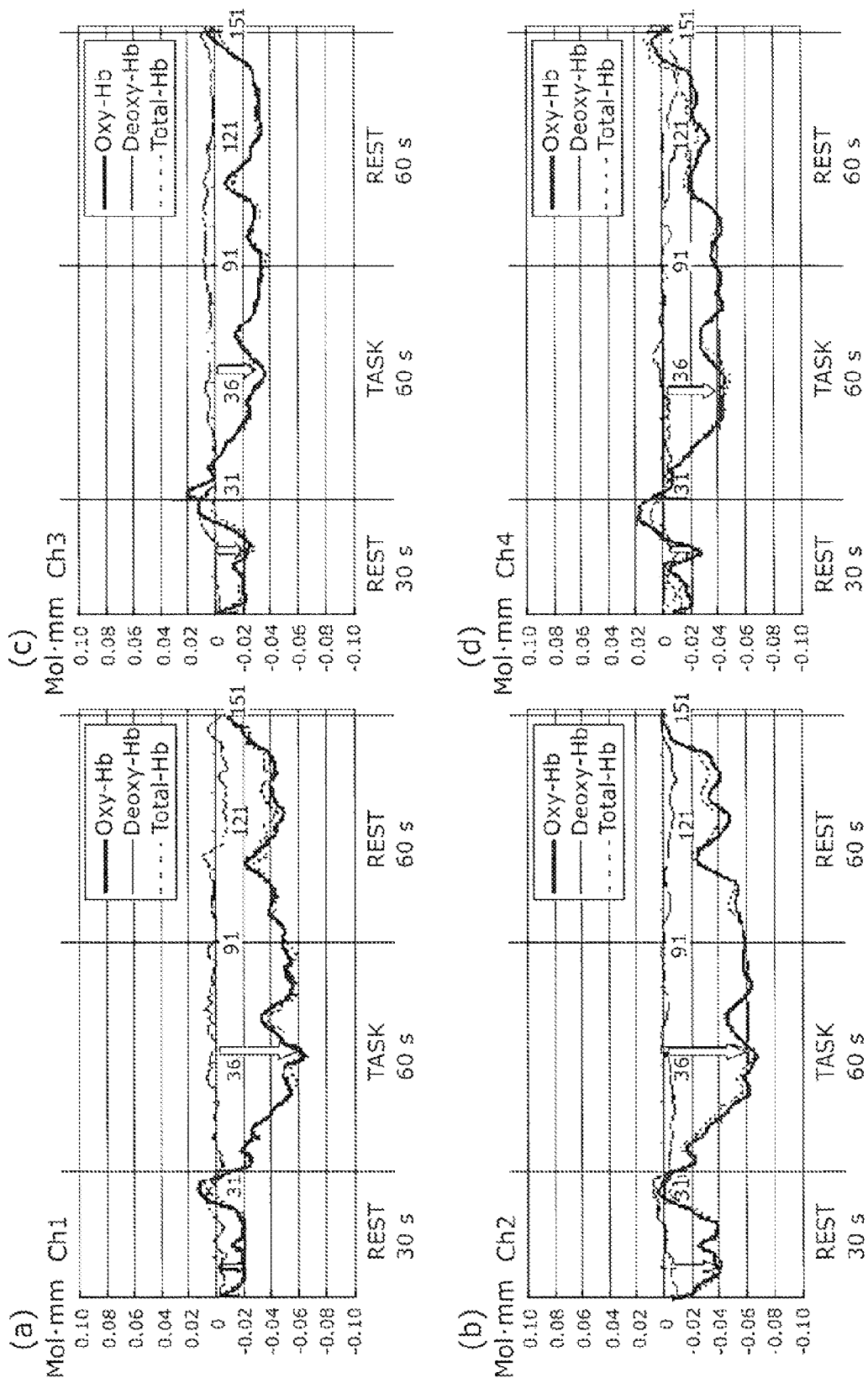
FIG. 17 indicates graphs for describing a process of selecting a channel.

FIG. 17 indicates graphs indicating increase or decrease in brain blood flow volumes measured in a plurality of channels during an experiment in which after 30 seconds of REST, a task of listening to the English news for 60 seconds was performed. In FIG. 17, (a) to (d) indicate increase or decrease in the brain blood flow volumes measured in channels 1 to 4, respectively. The graph in each of the channels clarifies decrease in the brain blood flow volume during the task time. However, it is clear that the amplitudes have differences.

Generally, when channels are different from each other, even in the case where distances between the light receiving units and the light emitting units are the same (for example, 3 cm), the NIRS sensor has different sensitivities, depending on a distance to the inner skin, the skull, and the brain. Furthermore, the NIRS sensor has different path lengths because of different optical coefficients, such as absorption coefficients. Thus, the NIRS sensor has difficulty in accurately comparing brain blood flow volumes. However, when the same channel is used, change in optical coefficient caused by increase or decrease in brain blood flow volume is smaller, and the path lengths are probably almost identical to each other. Here, for example, a ratio of the fluctuation range (reduction width) of the brain blood flow volume at a rest time that is calculated by the varying threshold obtaining unit 102 to the fluctuation range (reduction width) of the brain blood flow volume at a task time is calculated for each channel, and one of the channels having a higher ratio that is calculated is determined to be a channel for determining a degree of concentration. The channel having the higher ratio probably indicates a channel that significantly represents change from the rest time to the task time.

For example, in the channel 1, the minimum value of the brain blood flow volume at a rest time is −0.02, and the minimum value of the brain blood flow volume at a task time is −0.06. Thus, the ratio is 3 (=−0.06/−0.02). Furthermore, in the channel 2, the minimum value of the brain blood flow volume at a rest time is −0.04, and the minimum value of the brain blood flow volume at a task time is −0.06. Thus, the ratio is 3/2 (=−0.06/−0.04). Furthermore, in the channel 3, the minimum value of the brain blood flow volume at a rest time is −0.02, and the minimum value of the brain blood flow volume at a task time is −0.05. Thus, the ratio is 5/2 (=−0.051-0.02). Furthermore, in the channel 4, the minimum value of the brain blood flow volume at a rest time is −0.02, and the minimum value of the brain blood flow volume at a task time is −0.04. Thus, the ratio is 2 (=−0.047−0.02). The ratio in the channel 1 is the highest, and thus, the channel 1 is a channel indicating the most significant decrease in the brain blood flow volume due to the concentration. Thus, a degree of concentration of the subject is determined using the channel 1. The degree of concentration of the subject can be determined with accuracy by selecting one of the channels using this method.

The degree of concentration may be corrected using the ratio of the channel. For example, the degree-of-concentration calculating unit 107 may correct a weighted degree of concentration by multiplying the degree of concentration calculated by the degree-of-concentration calculating unit 107 by the ratio and a predetermined correction coefficient α.

Furthermore, when channels are closer, differences between path lengths are probably smaller. Thus, one of the channels may be selected in consideration of the channels.

Figure 18:
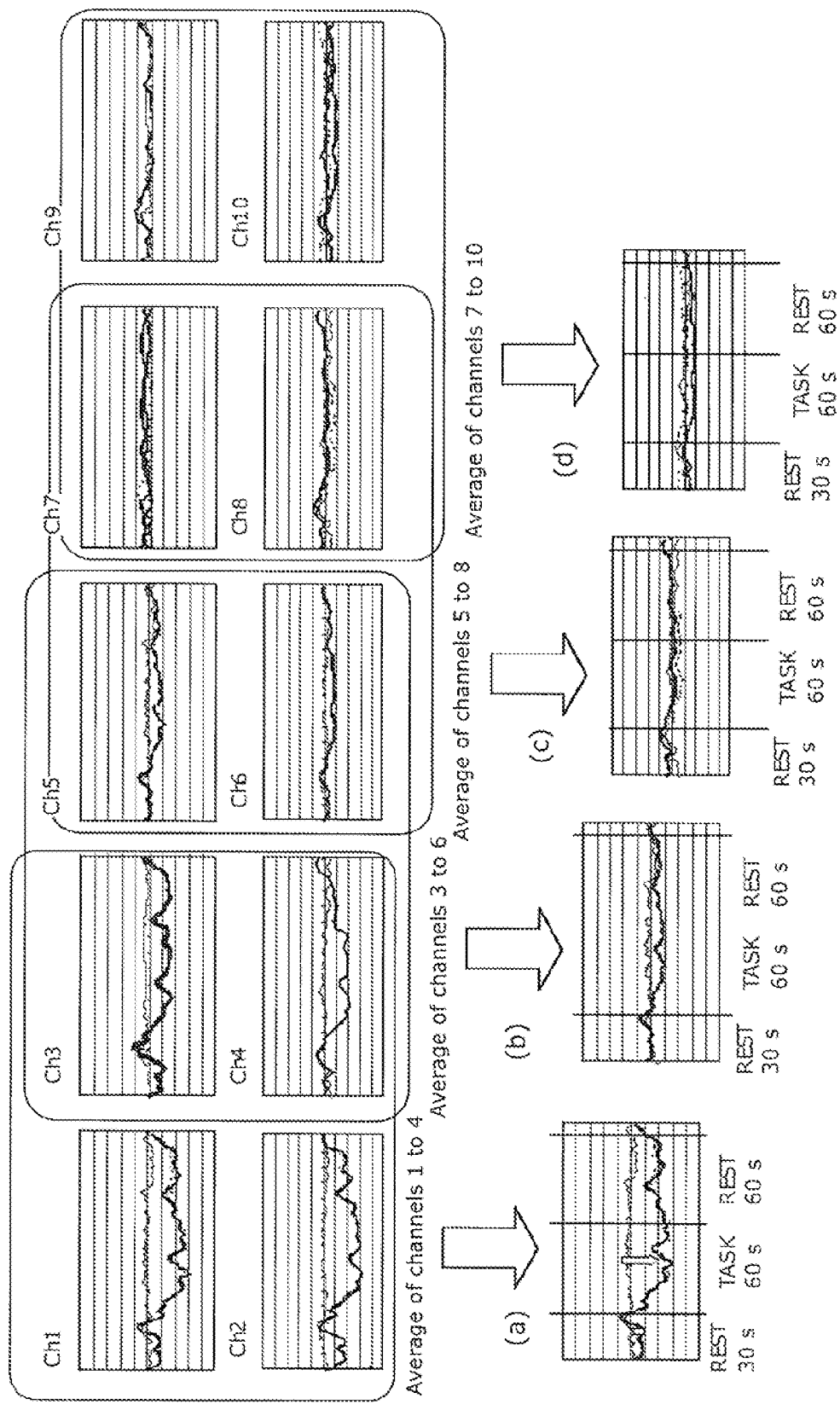
FIG. 18 indicates graphs for describing a process of selecting a channel.

FIG. 18 indicates graphs for describing a process of selecting a channel. Specifically, FIG. 18 indicates increase or decrease in brain blood flow volumes measured in a plurality of channels, when after 30 seconds of REST, a task of listening to the English news for 60 seconds was performed as in FIG. 17. The inventors have found, from the experiment, that the brain blood flow volume obtained by measuring the frontal lobe decreases when a concentration task such as an English problem or a puzzle is given and that the similar decreasing tendency occurs when closer channels are used. For example, FIG. 18 clarifies, in any of the channels 1 to 6, decrease in a brain blood flow volume at task times, and the decreasing tendency that is convex downward representing the recovery in the brain blood flow volume at rest times. As described above, since the brain blood flow volume includes fluctuations and artifacts due to a physiological phenomenon, it is generally represented as data having noise. Here, brain blood flow volumes measured at closer measurement parts may be averaged, and a channel in which the increasing or decreasing tendency of the brain blood flow volume can be the best measured may be selected. FIG. 18 includes a graph (a) of an average brain blood flow volume of the channels 1 to 4, a graph (b) of an average brain blood flow volume of the channels 3 to 6, a graph (c) of an average brain blood flow volume of the channels 5 to 8, and a graph (d) of an average brain blood flow volume of the channels 7 to 10, for example. As a result of comparison of a ratio at a rest time to that at a task time in each of the graphs using the similar method described above, the graph (a) of the average brain blood flow volume from the channels 1 to 4 has the highest ratio and the most significant decreasing tendency. Accordingly, a degree of concentration can be determined with accuracy and robustness against noise using the average brain blood flow volume of the channels 1 to 4.

Embodiment 2

Embodiment 1 describes a method for determining a degree of concentration based on change in the brain blood flow volume of an individual. Embodiment 2 will further describe a method for determining a degree of concentration of each individual based on change in the brain blood flow volumes of a plurality of individuals, and a method for determining a multiple-degree of concentration of the individuals for one task.

Figure 19:
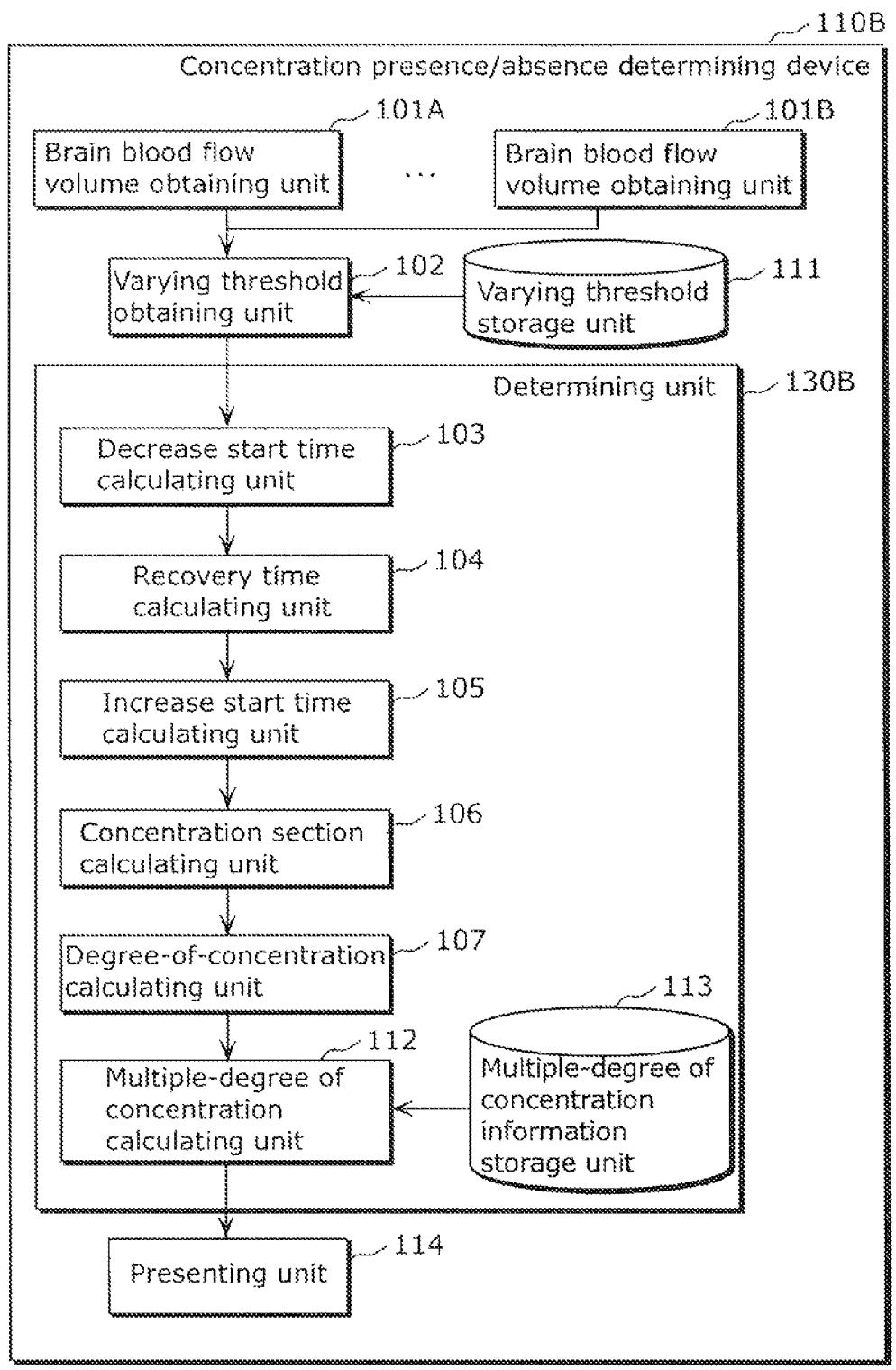
FIG. 19 is a block diagram illustrating a configuration of a concentration presence/absence determining device according to Embodiment 2.

FIG. 19 is a block diagram illustrating a configuration of a concentration presence/absence determining device 110B according to Embodiment 2. The same reference numerals are assigned to the same constituent elements as those in Embodiment 1, and the description thereof is omitted. The concentration presence/absence determining device 110B includes a plurality of brain blood flow volume obtaining units 101A and 1018, a varying threshold obtaining unit 102, a varying threshold storage unit 111, an determining unit 130B and a presenting unit 114.

The determining unit 130B includes a decrease start time calculating unit 103, a recovery time calculating unit 104, an increase start time calculating unit 105, a concentration section calculating unit 105, a degree-of-concentration calculating unit 107, and a multiple-degree of concentration calculating unit 112, and a multiple-degree of concentration information storage unit 113.

Each of the brain blood flow volume obtaining units 101A and 1018 detects a brain blood flow volume of a subject.

Figure 20:
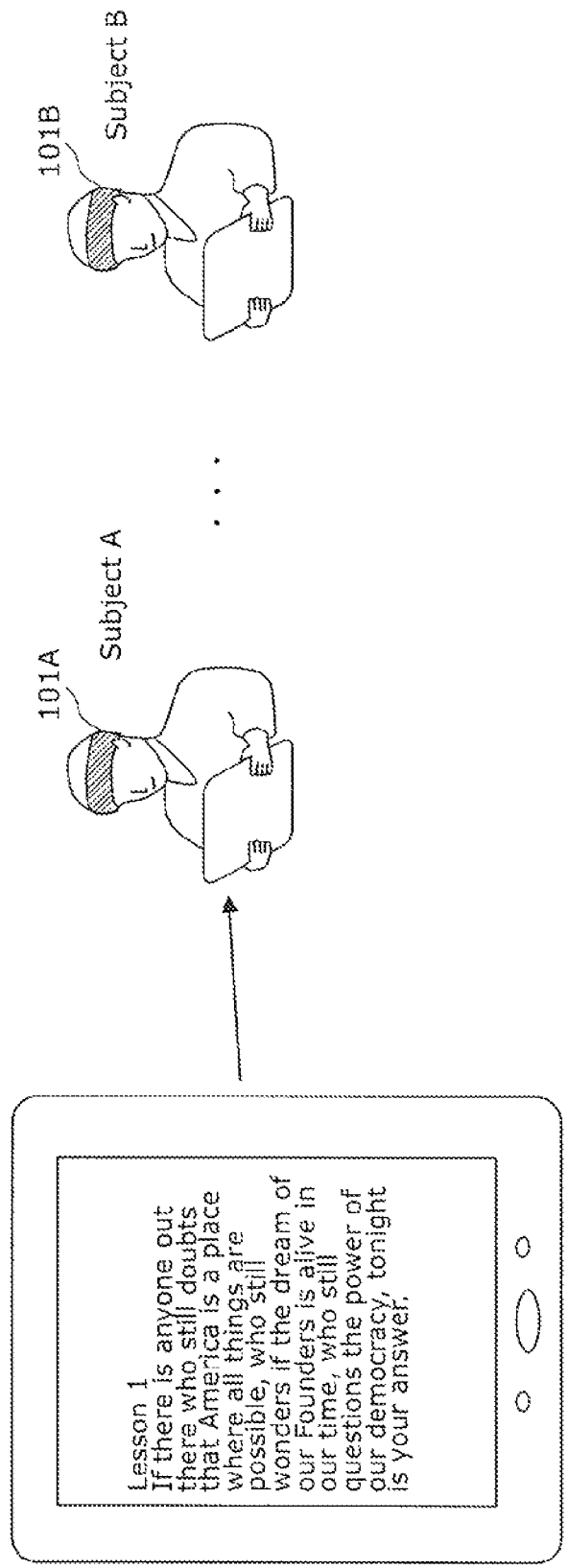
FIG. 20 illustrates an example of the concentration presence/absence determining device according to Embodiment 2.

FIG. 20 illustrates an example of the concentration presence/absence determining device 110B according to Embodiment 2. First, each of subjects A, B, and others wears a corresponding one of the brain blood flow volume obtaining units 101. For example, a task to be given is an English material for reading. For example, the task is given to a user under an experimental environment, or in a class or during a test under an actual environment. Furthermore, each of the subjects performs the task using an educational terminal, a shared bulletin board, a book, a test paper, or the like. The concentration presence/absence determining device 1103 compiles, in a wired or wireless manner, data on change in brain blood flow volumes detected, and measures degrees of concentration of the subjects for the predetermined task. Then, the concentration presence/absence determining device 110B monitors the brain blood flow volumes of the subjects, or analyzes them after the detection.

Figure 21:
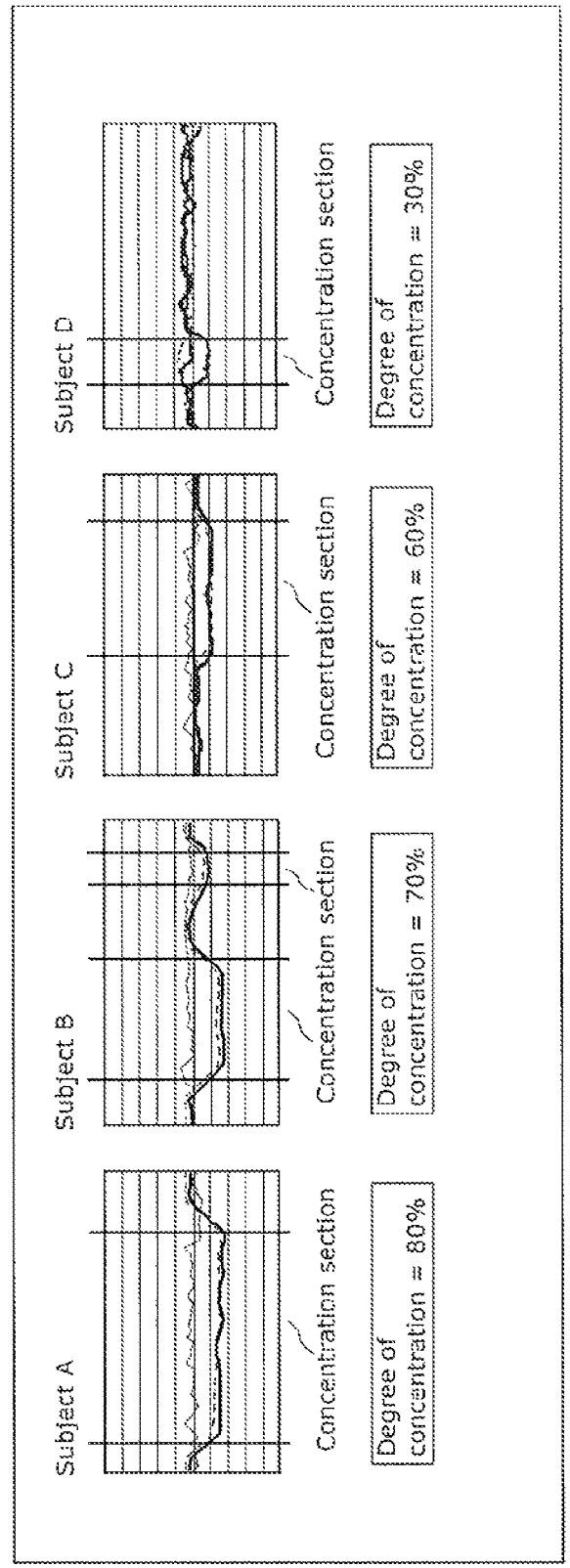
FIG. 21 indicates graphs of change in a brain blood flow volume of each of subjects presented by a presenting unit.

The presenting unit 114 presents change in each of the brain blood flow volumes detected, the degree of concentration of each of the subjects to be described later, and information on the overall degrees of concentration. FIG. 21 indicates graphs of change in the brain blood flow volumes of the subjects presented by the presenting unit 114.

The varying threshold obtaining unit 102 calculates a varying threshold for each of the subjects, based on change in the brain blood flow volume of the subject. The varying threshold is calculated from, for example, a fluctuation range at a predetermined rest time as in Embodiment 1. Although the varying threshold may be calculated for each task, it may be pre-stored for each individual, for example. Here, the varying threshold storage unit 111 stores the varying threshold for each individual. The varying threshold obtaining unit 102 sets a varying threshold with reference to the stored thresholds, and a decrease start time is calculated with reference to the varying threshold.

The decrease start time calculating unit 103 is a processing unit that calculates a decrease start time as in Embodiment 1, and calculates a decrease start time for each of the subjects. The recovery time calculating unit 104 is a processing unit that calculates a recovery time as in Embodiment 1, and calculates a recovery time for each of the subjects. The increase start time calculating unit 105 is a processing unit that calculates an increase start time as in Embodiment 1, and calculates an increase start time for each of the subjects. The concentration section calculating unit 106 is a processing unit that calculates a concentration section as in Embodiment 1, and calculates a concentration section for each of the subjects. The degree-of-concentration calculating unit 107 is a processing unit that calculates a degree of concentration as in Embodiment 1, and calculates a degree of concentration for each of the subjects. FIG. 21 illustrates a degree of concentration calculated for each of the subjects. For example, the degree of concentration of a subject A is 80%, the degree of concentration of a subject B is 70%, the degree of concentration of a subject C is 60%, and the degree of concentration of a subject D is 30%.

Furthermore, the multiple-degree of concentration calculating unit 112 determines information on a concentration tendency of multiple subjects as a multiple-degree of concentration. The multiple-degree of concentration information storage unit 113 stores information for determining the multiple-degree of concentration (multiple-degree of concentration information). The multiple-degree of concentration calculating unit 112 determines the multiple-degree of concentration, with reference to the multiple-degree of concentration information.

FIG. 22 is a table for describing a multiple-degree of concentration information. For example, the multiple-degree of concentration information includes a ratio of persons who concentrate, an average concentration start time, and an average concentration end time, and the multiple-degree of concentration information storage unit 113 stores information on a method for calculating the multiple-degree of concentration. For example, the ratio of persons who concentrate is calculated by dividing the number of subjects whose degree of concentration is higher than or equal to a threshold (for example, 60%), by the total number of subjects. Furthermore, the average concentration start time is calculated by dividing the total of decrease start times that are times at each of which the subject starts to concentrate, by the total number of subjects. Furthermore, the average concentration end time is calculated by dividing the total of increase start times that are times at each of which the subject starts lacking in concentration, by the total number of subjects.

Figure 23:
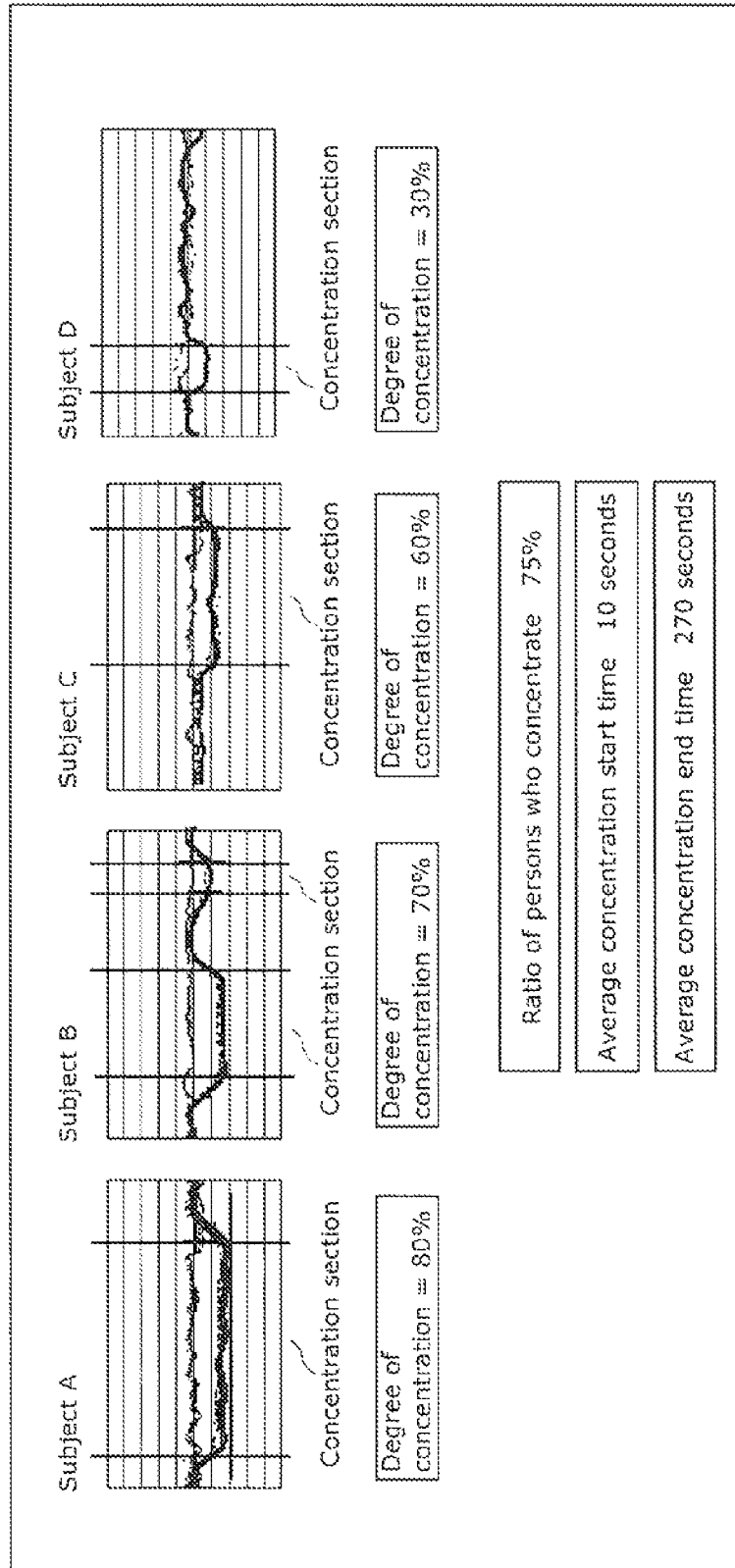
FIG. 23 indicates graphs of an example of a multiple-degree of concentration presented by the presenting unit.

The presenting unit 114 presents the multiple-degree of concentration on a display and others. FIG. 23 presents that the subjects whose degree of concentration is higher than or equal to a threshold (60%) are subjects A, B, and C, and a ratio of the subjects who concentrate to the total number of subjects is calculated as 75% by dividing 3 by 4 of the total number of subjects. Furthermore, FIG. 23 presents that the average concentration start time is 10 seconds after starting the task, based on the decrease start times of the subjects. Similarly, FIG. 23 presents that the average concentration end time is 270 seconds after starting the task, based on the increase start times of the subjects.

As such, a tendency of concentration of all the subjects during performing a task given to the subjects, such as reading an English material, can be clarified as a multiple-degree of concentration. For example, it is possible to understand an overall concentration state of the subjects in a class, such as determining whether or not an English listening test is a material on which the subjects (students) concentrate or all the students concentrate on the material. Although the multiple-degree of concentration is described as a ratio of persons who concentrate, an average concentration start time, and an average concentration end time in the example, the multiple-degree of concentration is not limited to such. For example, calculating a variance of degrees of concentration makes it possible to understand whether or not the degrees of concentration vary. Furthermore, calculating a variance of concentration end times makes it possible to understand the variation in duration of concentration.

Figure 24:
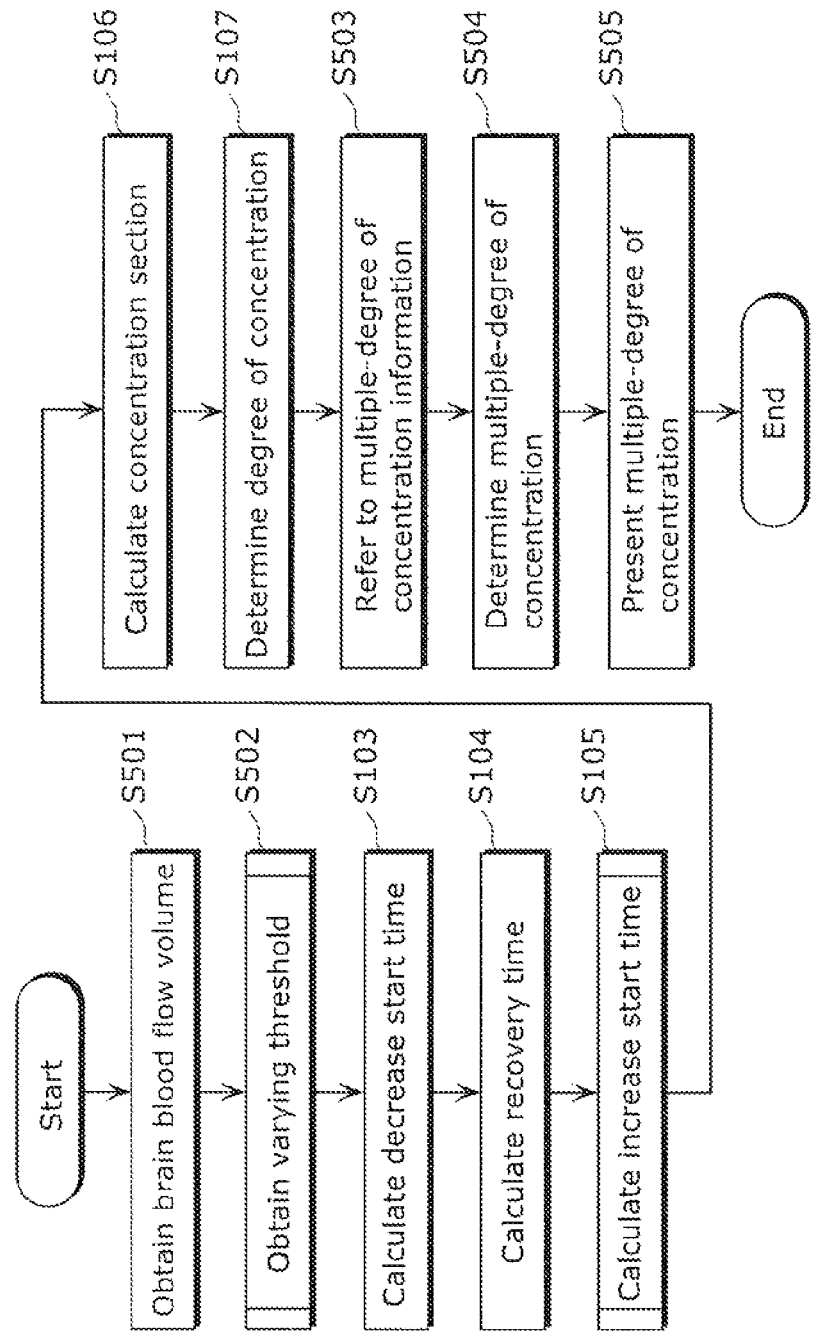
FIG. 24 is a flowchart indicating processes performed by the concentration presence/absence determining device according to Embodiment 2.

The procedure according to Embodiment 2 will be described with reference to FIG. 24. The same processes as those in Embodiment 1 are denoted by the same reference numerals.

The brain blood flow volume obtaining unit 101 obtains a brain blood flow volume of each subject (Step S501). The varying threshold obtaining unit 102 obtains a varying threshold stored in the varying threshold storage unit 111 (Step S502).

The decrease start time calculating unit 103 calculates a decrease start time of each of the subjects (Step S103). Next, the recovery time calculating unit 104 calculates a recovery time of each of the subjects (Step S104). Then, the increase start time calculating unit 105 calculates an increase start time at which the brain blood flow volume finally starts to increase by extending back from the recovery time of each of the subjects (Step S105).

Next, the concentration section calculating unit 106 calculates a concentration section of each of the subjects (Step S106). The concentration section calculating unit 106 calculates, as a concentration section, a period from the decrease start time calculated at Step S103 to the increase start time calculated at Step S105. The degree-of-concentration calculating unit 107 determines a degree of concentration of each of the subjects (Step S107).

Next, with reference to the multiple-degree of concentration information stored in the multiple-degree of concentration information storage unit 113 (Step S503), the multiple-degree of concentration calculating unit 112 determines the multiple-degree of concentration (Step S504). Then, the presenting unit 114 presents the multiple-degree of concentration (Step S505). For example, the presenting unit 114 presents the multiple-degree of concentration as illustrated in FIG. 23.

The multiple-degree of concentration calculating unit 112 may determine the multiple-degree of concentration based on increase or decrease in brain blood flow volumes when the subjects were performing the task. The specific example will be described below.

Figure 25:
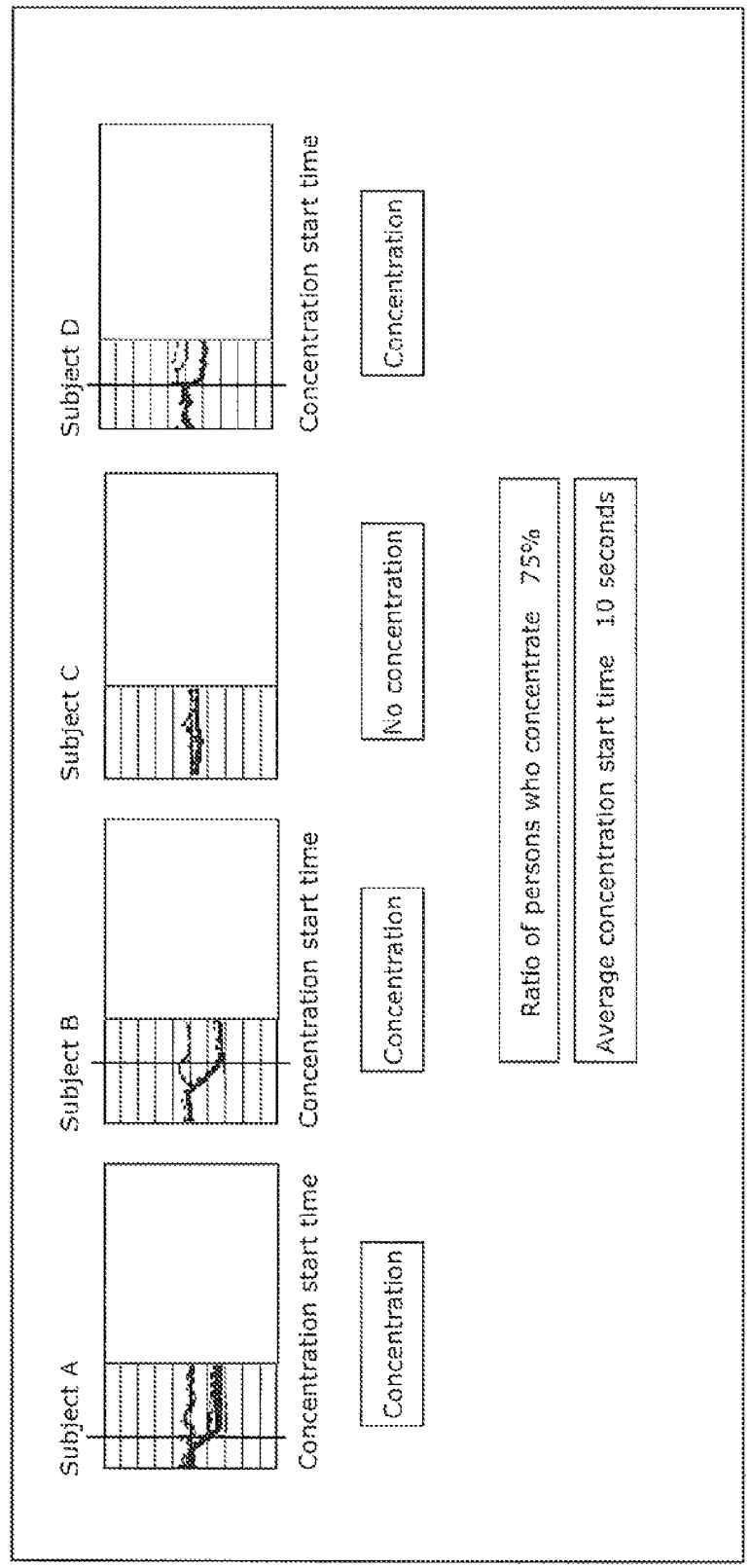
FIG. 25 indicates graphs of an example in which the increase or decrease in a brain blood flow volume of each of the subjects is displayed in real time.

FIG. 25 indicates graphs of an example in which the increase or decrease in the brain blood flow volume of each of the subjects is displayed in real time. Here, each of the subjects is performing the task, and the increase or decrease in the brain blood flow volume is detected.

First, the varying threshold stored in the varying threshold storage unit 111 for each of the subjects is referred to. When the brain blood flow volumes are smaller than the respective varying thresholds, assuming that the subjects are in a concentration state, the degree-of-concentration calculating unit 107 determines whether or not each of the subjects is concentrating. In FIG. 25, the degree-of-concentration calculating unit 107 determines that the subjects A, B, and D are concentrating. Since the subject C is not concentrating, "Concentration" is not displayed.

Furthermore, a ratio of persons who are concentrating is calculated as a multiple-degree of concentration. Information on a ratio of persons who are concentrating, specifically, a method for calculating a ratio of persons who are concentrating is stored as multiple-degree of concentration information. The ratio of persons who are concentrating is calculated by dividing the number of persons who concentrate by the total number of subjects. Since three out of four subjects are concentrating, the ratio is calculated and displayed as 75%. As such, understanding of a concentration state of subjects in real time makes it possible to determine the appropriateness of the task and the concentration state of the subjects.

(Modification 2)

In Embodiments 1 and 2, a start time and an end time of each task are automatically input or set by the measurement observer, and a degree of concentration is calculated based on a concentration section within a task time (target section) with the preset of the start time and the end time. However, the calculation is not limited to such. Another concentration presence/absence determining device will be described hereinafter.

Figure 26:
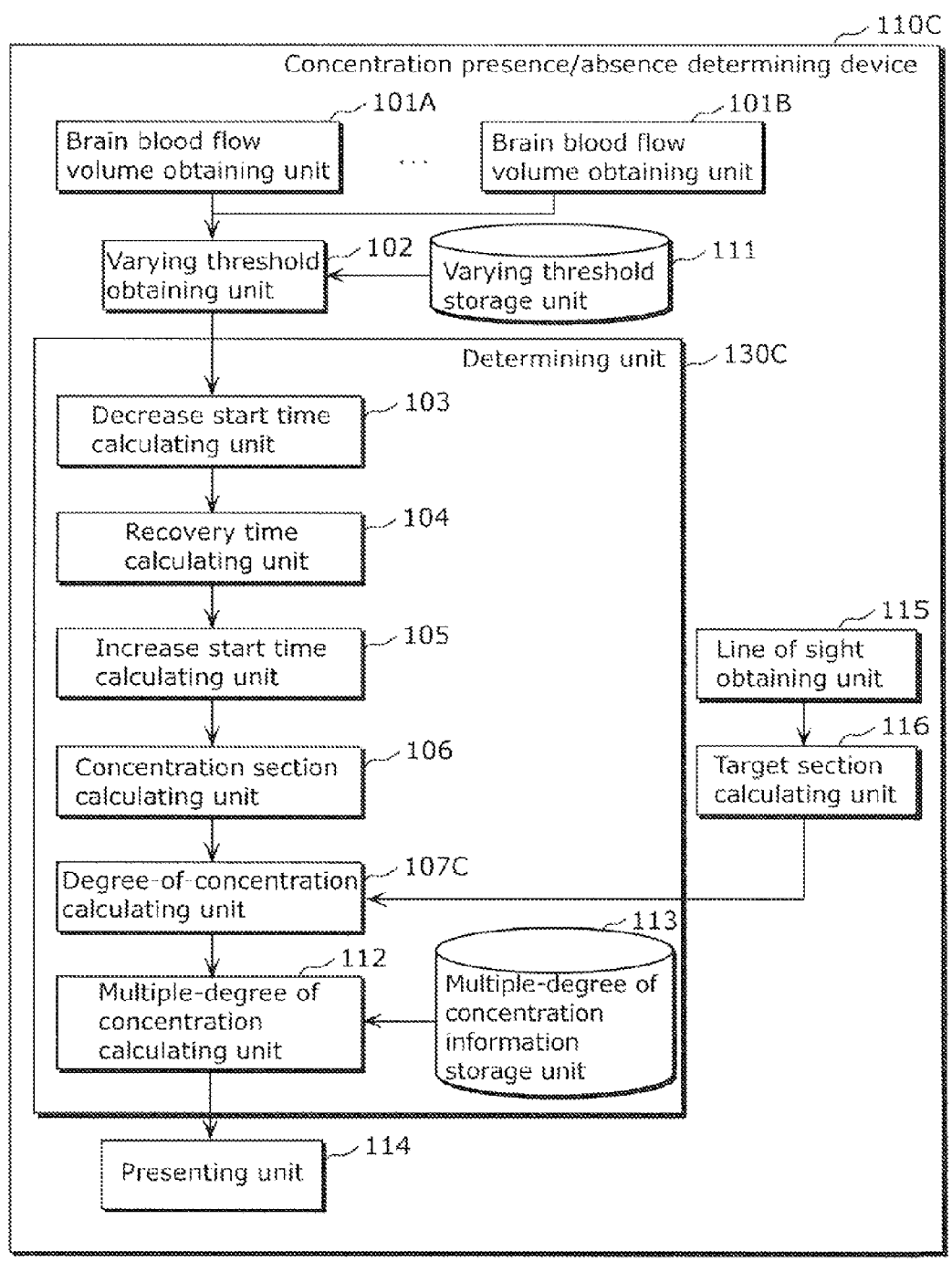
FIG. 26 is a block diagram illustrating a configuration of a concentration presence/absence determining device according to Modification 2.

FIG. 26 is a block diagram illustrating a configuration of a concentration presence/absence determining device 110C according to Modification 2.

Figure 27:
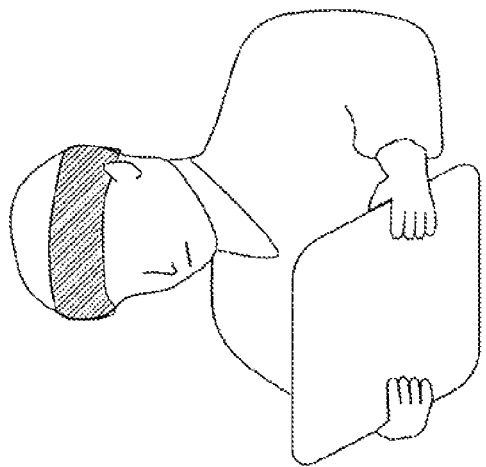
FIG. 27 illustrates an example of the concentration presence/absence determining device according to Modification 2.

The concentration presence/absence determining device 110C includes a line of sight obtaining unit 115 and a target section calculating unit 116, in addition to the configuration of the concentration presence/absence determining device 110B in FIG. 19. The line of sight obtaining unit 115 detects movement of a line of sight of each subject. FIG. 27 illustrates an example of the concentration presence/absence determining device 1100. For example, the line of sight obtaining unit 115 is included in a terminal to be used by each of the subjects, and detects movement of a line of sight of the subject. The line of sight obtaining unit 115 may be included not in the terminal but in a desk or a personal computer of the subject, or a black board or a bulletin board in front when the subject uses the concentration presence/absence determining device 110C during a class or a lecture.

The target section calculating unit 116 calculates a target section for which a degree of concentration is calculated, from information on the line of sight detected by the line of sight obtaining unit 115. For example, assume that the task here is reading an English material and each terminal of the subject displays an examination question. The target section calculating unit 116 determines a task execution section when the subject gazes at the screen of the terminal, and a non-task execution section when the subject does not gaze at the screen of the terminal, and calculates the task execution section as a target section.

The degree-of-concentration calculating unit 107C calculates a degree of concentration based on the target section calculated by the target section calculating unit 116. The calculation method is the same as that by the degree-of-concentration calculating unit 107.

Figure 28:
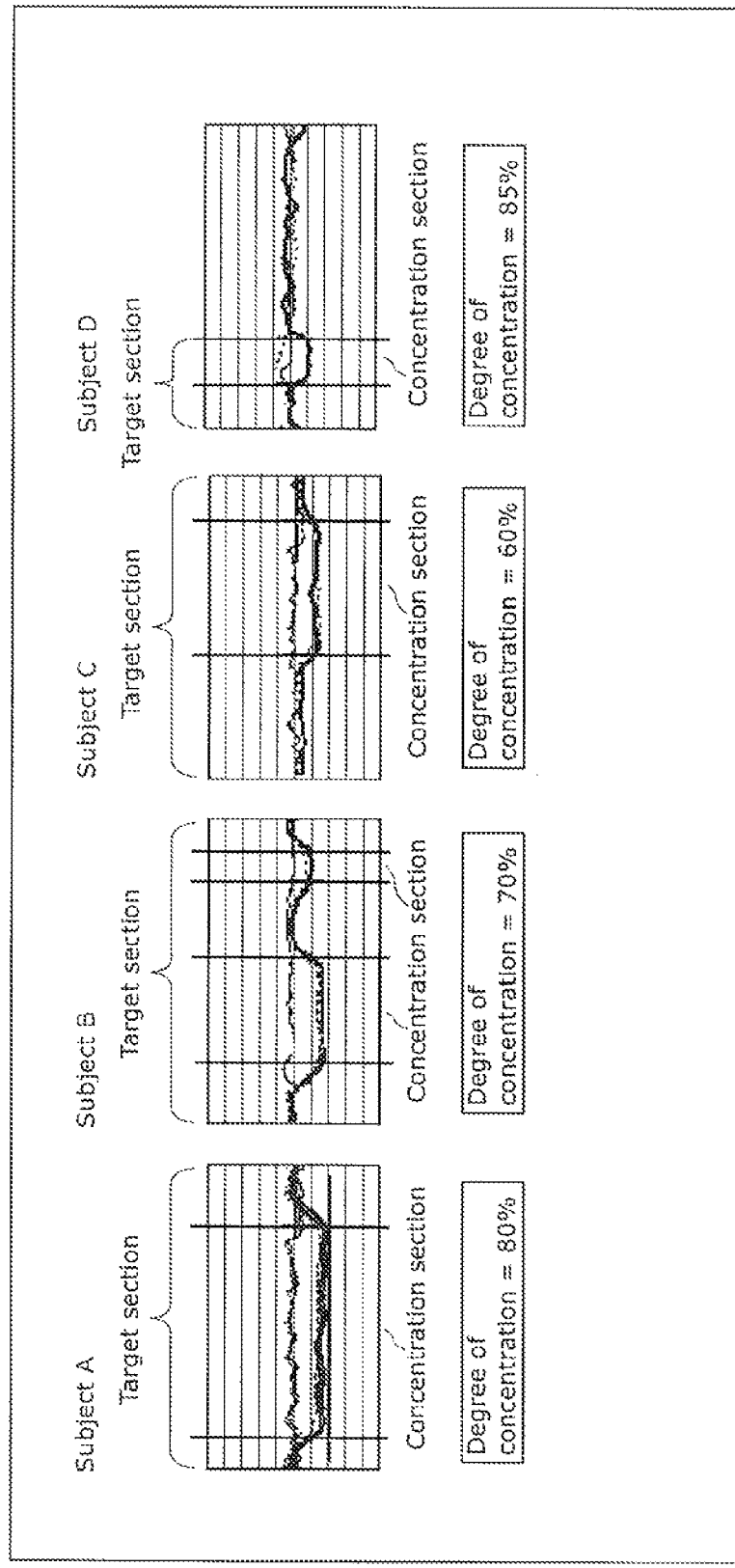
FIG. 28 indicates graphs of target sections and degrees of concentration that are calculated.

FIG. 28 indicates graphs of target sections and degrees of concentration that are calculated. For example, since a subject A constantly listened to English displayed on a terminal and was concentrating during detection of the brain blood flow volume, the whole measurement period is calculated as the target section, and the degree of concentration is calculated as 80% from a ratio of the concentration section to the whole measurement period. On the other hand, a subject D was listening to English for a short period while the concentration section was shorter, and only the first half of the whole measurement period is calculated as the target section. The degree of concentration is calculated as 85% from the concentration section within the target section.

For example, even when the same task, for example, the same English reading material is given, some subjects finish reading it earlier than the others. The line of sight obtaining unit 115 can calculate a target section with higher accuracy by considering approaches to the task for each of the subjects, and further a degree of concentration corresponding to the target section.

With the presence of a plurality of tasks, a type of each of the tasks may be first detected, and a degree of concentration corresponding to the task may be calculated.

The description of Embodiments 1 and 2 is based on one task. However, in tests and examinations under the actual environment, the task is not limited to one. There are cases where there are tasks and scenes in which the execution order is different for each subject. For example, when degrees of concentration of students are measured in a test in which examination questions are given, each of the students may determine the order to solve the questions.

In the above case, which question the subject is solving can be clarified from a correspondence between a terminal to which the questions are sent and a line of sight of the subject facing the screen on which the questions are displayed. Then, the degree of concentration of the subject can be determined for each of the questions.

Figure 29:
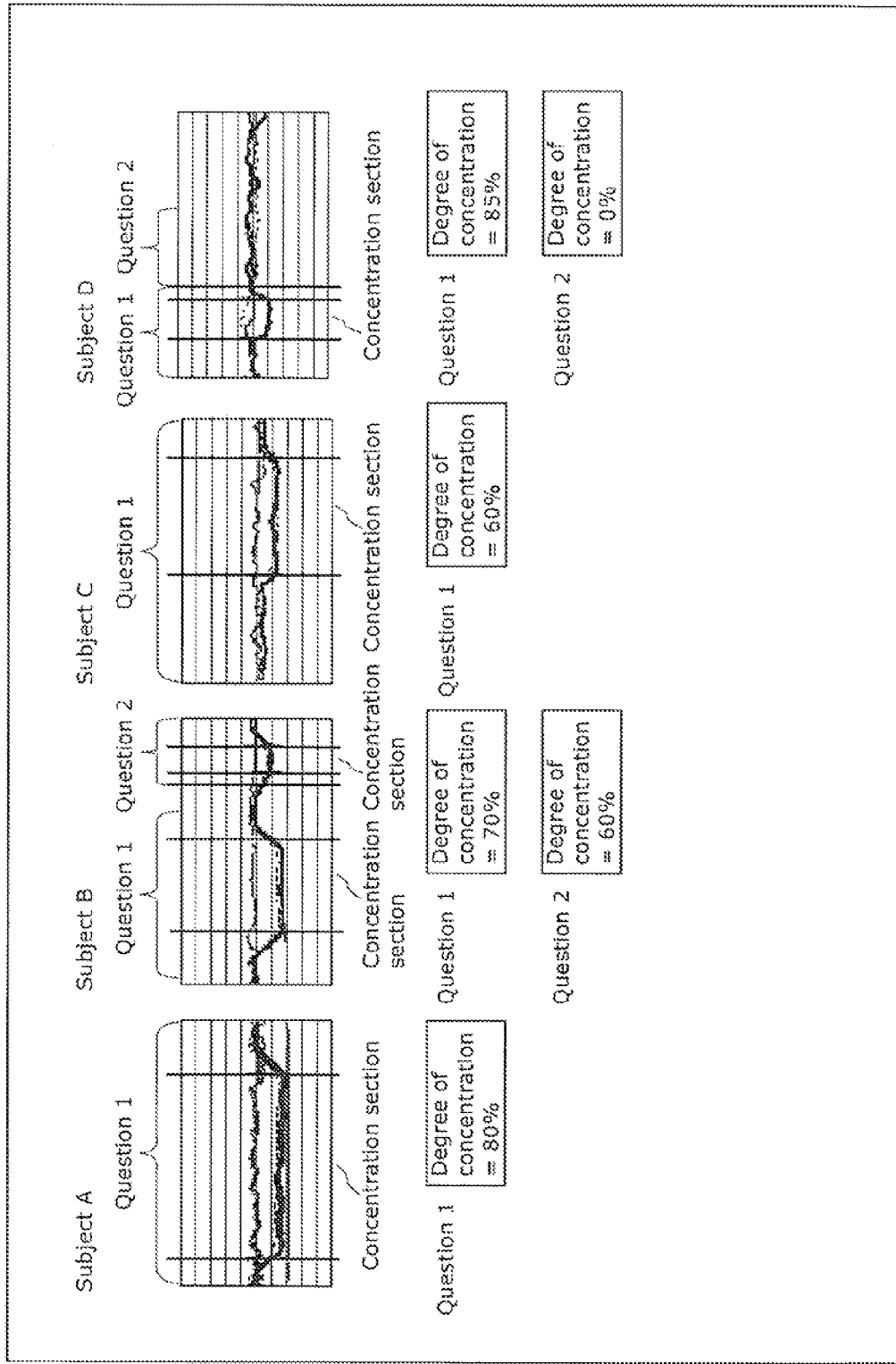
FIG. 29 indicates graphs of an example of a result presented by the presenting unit.

FIG. 29 indicates graphs of an example of a result presented by the presenting unit 114. For example, a subject A considers and concentrates on a question 1 over an entire measurement period, and it is determined that the degree of concentration is 80% for the question 1. A subject B considers and concentrates on the question 1 for the first half of the measurement period, and considers and concentrates on a question 2 later. The respective degrees of concentration are 70% and 60%. A subject C considers and concentrates on the question 1 over the entire measurement period, and it is determined that the degree of concentration is 60% for the question 1. A subject D considers and concentrates on the question 1 in the beginning of the measurement period, and considers the question 2 later but does not concentrate. The respective degrees of concentration are 85% and 0%.

As such, determining a task that is being executed and a degree of concentration for the task makes it possible to understand the entire degrees of concentration for each task and the progress state.

Embodiment 3

Embodiments 1 and 2 describe the method for determining g a degree of concentration using listening to English as a task for the application. The application is not limited to this. For example, a concentration presence/absence determining device determines a degree of concentration of the user for content items, such as a movie, a commercial, and music, such that the device is used as a content evaluation apparatus. The specific example will be described below.

The content evaluation apparatus according to Embodiment 3 will be described.

Embodiment 3 assumes a content item as a commercial of a product or a service, presentation for describing a function of the product, a commercial of a movie or a television program, and a television program for a mail order. These content items are generally created to be viewed by the user for the purpose of attracting specific targets and being recognized by the user. Furthermore, although the user is sometimes impressed by these content items, most content items are created to impress the user with a product, a function, a price, and the details of the product that are appealed in the content items for the recognition.

Thus, the content items are evaluated based on viewpoints of whether or not (1) the user concentrates on the content items and (2) the content items advertise a product, a function of the product, and others.

Figure 30:
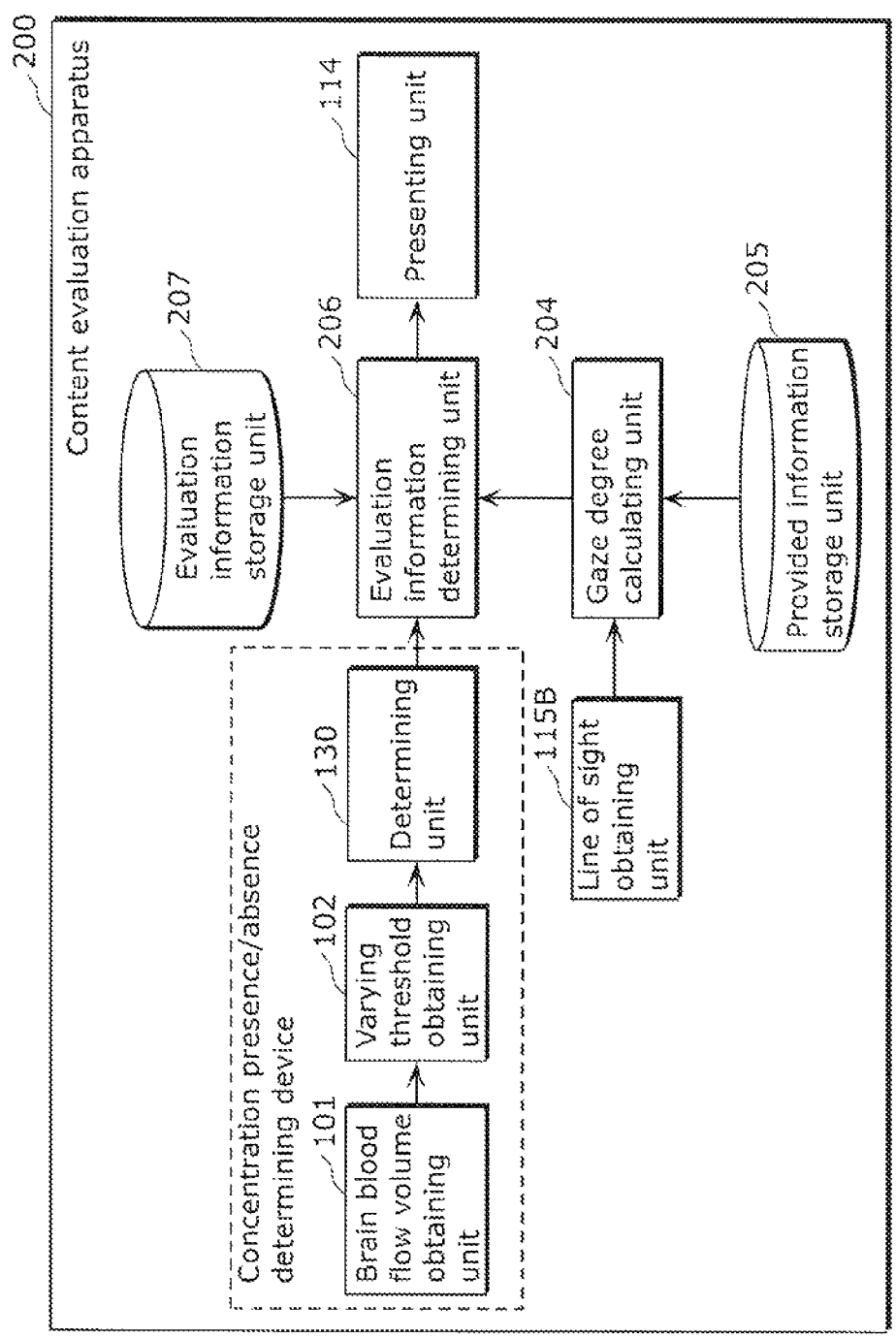
FIG. 30 is a block diagram illustrating a configuration of a content evaluation apparatus according to Embodiment 3.

FIG. 30 is a block diagram illustrating a configuration of a content evaluation apparatus 200 according to Embodiment 3.

In FIG. 30, the content evaluation apparatus 200 is a content evaluation apparatus that determines an evaluation of the user to an image content by analyzing a biosignal of the user when the user views the image content, and includes a brain blood flow volume obtaining unit 101, a varying threshold obtaining unit 102, an determining unit 130, a line of sight obtaining unit 115B, a gaze degree calculating unit 204, a provided information storage unit 205, an evaluation information determining unit 206, an evaluation information storage unit 207, and a presenting unit 114.

Since the configurations of the brain blood flow volume obtaining unit 101, the varying threshold obtaining unit 102, the determining unit 130, and the presenting unit 114 are the same as those according to Embodiment 1, the detailed description thereof is not repeated.

The line of sight obtaining unit 115B is a sensor that measures a line-of-sight position at which the user gazes from a pupil position obtained by, for example, a camera.

Figure 31:
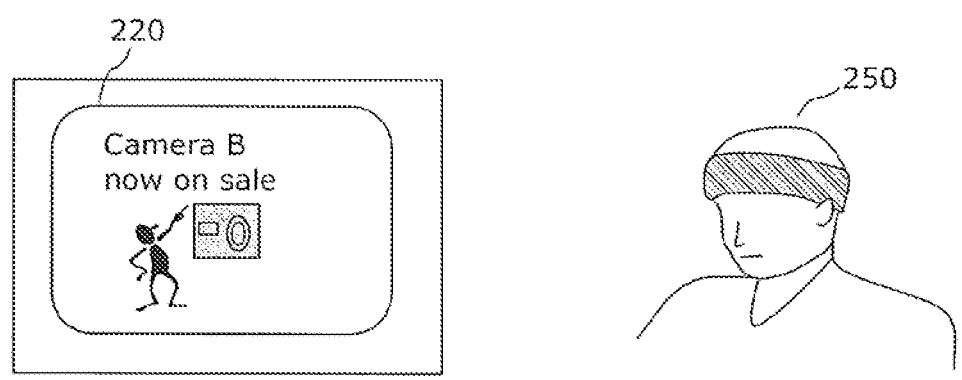
FIG. 31 illustrates a method for obtaining a brain blood flow volume when the user views a content item.

FIG. 31 illustrates an example when a user is viewing a content item. The user who is a subject 250 is viewing a content item 220 including a commercial of a camera B.

Again with reference to FIG. 30, the provided information storage unit 205 stores provided information that is information including (i) a display area of a provided image that is an image included in the image content and (ii) a display period during which the provided image is displayed in the display area. The details will be described later.

The gaze degree calculating unit 204 calculates a degree at which the user gazes at a provided image (hereinafter referred to as "gaze degree"), with reference to the provided information stored in the provided information storage unit 205 based on a position relationship between a line-of-sight position at a display period and a display area. For example, the gaze degree calculating unit 204 determines whether or not a distance between (i) a line-of-sight position at each of display periods included in the provided information and (ii) a display area corresponding to the display period is smaller than a predetermined threshold, for each of the display periods, determines that the user gazes during at least one of the display periods when the distance is smaller than the threshold, and calculates a gaze degree as a ratio of the sum of the at least one of the display periods at which it is determined that the user gazes, to the total display periods included in the provided information. The details of the method for calculating a gaze degree will be described later.

The evaluation information storage unit 207 stores an evaluation information template including evaluation information of the image content associated with a set of a gaze degree, presence or absence of concentration, and a degree of concentration. The data structure of the evaluation information template will be described later.

The evaluation information determining unit 206 determines, with reference to the evaluation information template, the evaluation information corresponding to the gaze degree calculated by the gaze degree calculating unit 204, and the presence or absence of concentration and the degree of concentration that are determined by the determining unit 130, as an evaluation of the user to the image content. The details will be described later.

Figure 32:
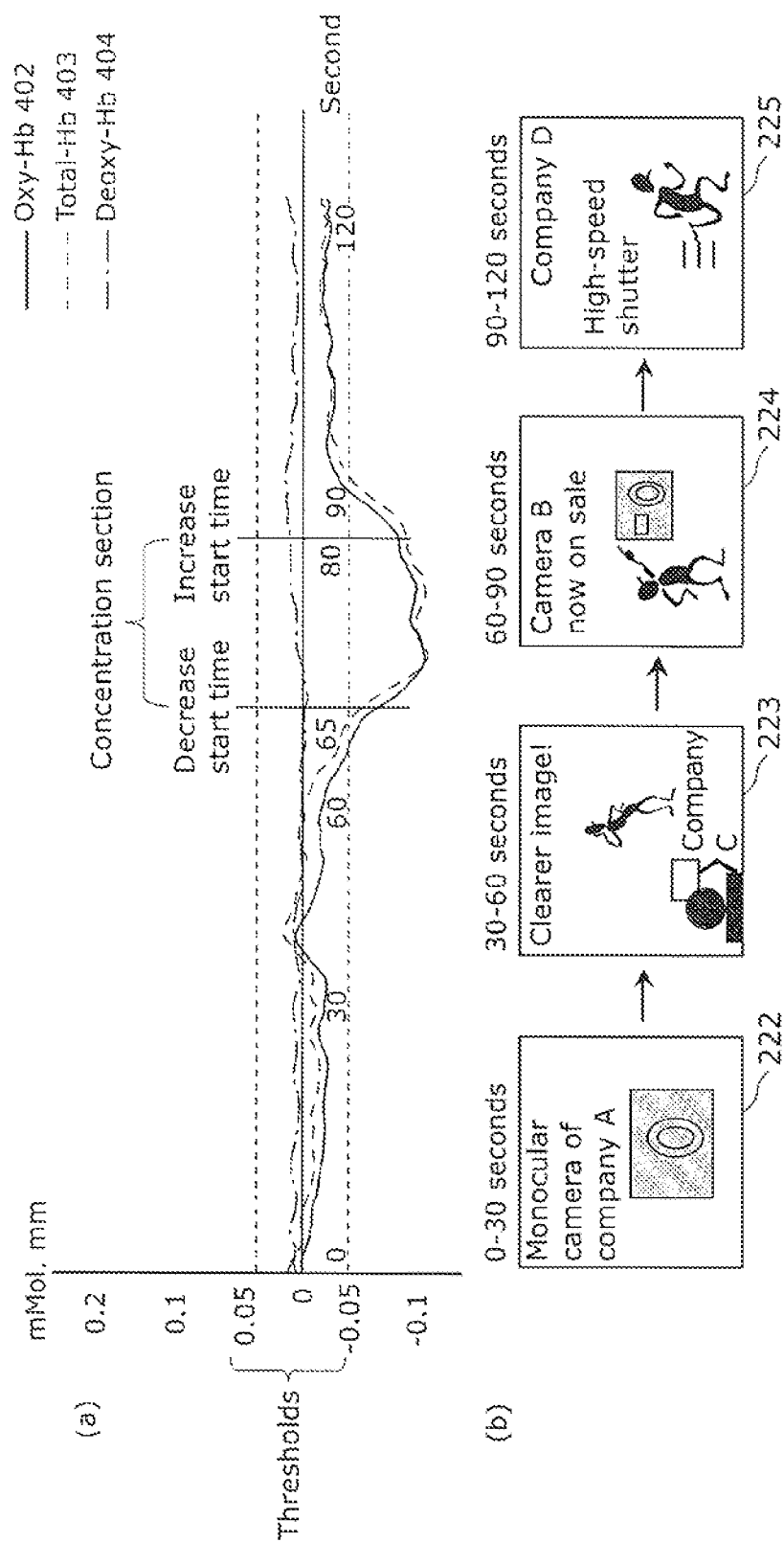
FIG. 32 illustrates an example of a correspondence relationship between video content items and an amount of change in a brain blood flow, based on an experiment.

FIG. 32 illustrates an example of a correspondence relationship between video content items and amounts of change in a brain blood flow, based on an experiment. (b) in FIG. 32 schematically illustrates content items to be viewed. Each of the content items is a movie that describes a product. For example, a content item 222 that describes a monocular camera of a company A is displayed from 0 second to 30 seconds after start of the measurement. Next, a content item 223 that describes a digital camera of a company C is displayed from 30 to 60 seconds. Next, a content item 224 that describes a digital camera of a company B is displayed from 60 to 90 seconds. Then, a content item 225 that describes a digital camera of a company D is displayed from 90 second to 120 seconds.

(a) of FIG. 32 is a graph indicating the brain blood flow volume of the user during the time when the user views the content items illustrated in (b) of FIG. 32. Specifically, (a) is a graph obtained by conducting an experiment using a NIRS sensor and detecting change in the blood flow of the frontal lobe of the user during the time when the user views the content items.

The sampling interval for detecting the brain blood flow volume is 0.6 second, the horizontal axis represents a time (second), and the vertical axis represents an amount of change in hemoglobin (mMol×mm) from the start of measurement that is a base time. (a) of FIG. 32 indicates three graph lines that overlap one another, showing increase or decrease in three types of hemoglobin: a graph 402 indicating an amount of change in the concentration of oxygenated hemoglobin (oxy-Hb), a graph 404 indicating an amount of change in the concentration of deoxygenated hemoglobin (deoxy-Hb); and a graph 403 indicating an amount of change in the concentration of total hemoglobin (total-Hb). Generally, when the brain blood flow increases or decreases, the oxygenated hemoglobin increases or decreases with several seconds of delay. Thus, measurement of an amount of change in the concentration of oxygenated hemoglobin makes it possible to obtain an amount of change in a brain blood flow. In order to simplify the description, the value of the concentration of oxygenated hemoglobin or total hemoglobin at a base time (for example, when the brain blood flow starts to be measured) is assumed to be 0, and the amount of change in the brain blood flow from the base time is called a brain blood flow. In other words, a positive brain blood flow means increase in the brain blood flow from the base time, and a negative brain blood flow means decrease in the brain blood flow from the base time.

As illustrated in (a) of FIG. 32, each of the graph lines indicates the almost constant values with slight increase or decrease during 0 second to 30 seconds and 30 to 60 seconds. In the vicinity of 65 seconds, the concentrations of oxygenated hemoglobin and total hemoglobin gradually decrease and then again increase.

Here, a relationship between change in a brain blood flow and psychological change of the user to content items will be described with reference to FIGS. 33A and 33B.

First, 12 users who are subjects viewing a plurality of content items (movie that describes a product or commercials continuously played), and the respective brain blood flows were measured during the viewing. Furthermore, the subjects verbally answered the psychological states, feedback, and others for the viewed content items. The relationship between change in the brain blood flows obtained as a result of the experiment and the psychological states will be reported hereinafter with reference to FIGS. 33A and 33B.

Figure 33A:
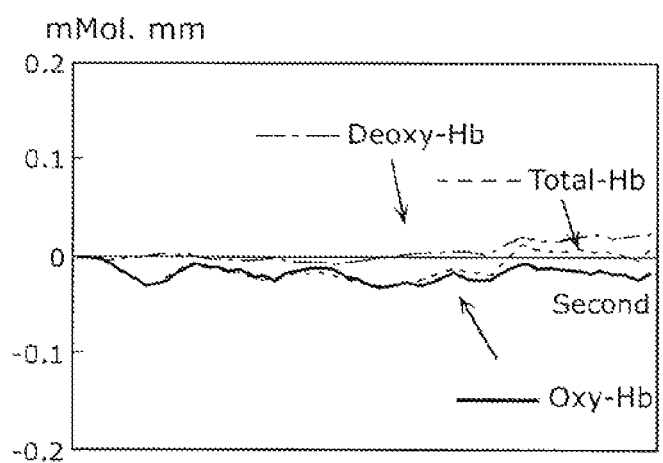
FIG. 33A is a graph indicating an example of change in the brain blood flow volume when the user who was viewing a content item was not interested in the content item.
Figure 33B:
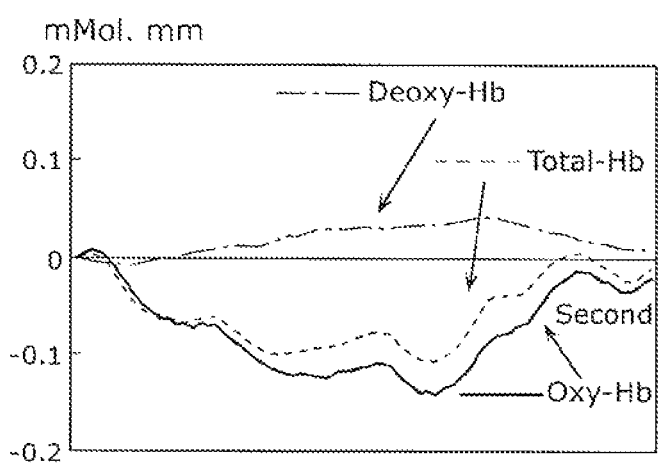
FIG. 33B is a graph indicating an example of change in the brain blood flow volume when the user who was viewing a content item was concentrating on the content item.

Each of FIGS. 33A and 33B is a graph obtained by actually detecting change in the blood flows in the frontal lobes of the users who viewed the content items, using the NIRS sensors. The sampling interval for detecting the brain blood flow volume is 0.6 second, the horizontal axis represents a time (second), and the vertical axis represents an amount of change in hemoglobin (mMol×mm) from the start of measurement. In each of the graphs, three graph lines indicate increase or decrease in three types of hemoglobin including: oxygenated hemoglobin (oxy-Hb); deoxygenated hemoglobin (deoxy-Hb); and total hemoglobin (total-Hb).

As the result of experiment, many of the users did not have any change in the brain blood flows for the content items or scenes for which the users did not have any impression and in which the users were not so interested. Here, the scenes are parts of the content items.

For example, FIG. 33A is a graph indicating change in the brain blood flow when one of the users was viewing a certain content item and the transition of typical data when the user was not interested in the content, FIG. 33A clarifies that the amount of increase or decrease in the concentration of each of deoxygenated hemoglobin, oxygenated hemoglobin, and total hemoglobin is small and remains almost constant. Furthermore, the user verbally answered that the content item did not particularly impress the user and the user was not interested in the content item. The user was probably in a state of viewing the content item without any feeling. Furthermore, the user was also in a state of viewing the function and the product appealed in the content item without any feeling.

Furthermore, the result of experiment shows that many of the users had change in the brain blood flows to a content item in which the users were interested or which the user concentrated to view. In particular, many of the users had decrease in the concentration of the oxygenated hemoglobin and total hemoglobin. FIG. 33B is a graph indicating an example of change in the brain blood flow when one of the users was viewing a certain content item and was concentrating to view the content. Although the concentration of deoxygenated hemoglobin remains almost constant, the concentration of oxygenated hemoglobin and total hemoglobin decrease with the passage of time, and then increase and recover. In the verbal answer, the user told that the content item impressed the user very much and the user concentrated on viewing the content item. Specifically, the user was in a state of dispassionately viewing the content item with concentration. Furthermore, the user answered that the user also saw the function and the product appealed in the content item and was impressed by these.

Based on the obtained knowledge, the determining unit 130 included in the content evaluation apparatus 200 according to Embodiment 3 determines whether or not the user concentrates and calculates a concentration section, using the method described.

The determining unit 130 may perform data smoothing or baseline correction using the amount of deoxygenated hemoglobin, on a measurement result of the brain blood flow volume obtained from the brain blood flow volume obtaining unit 101 as the brain blood flow volume for use in identifying a type of reaction. Since a brain blood flow volume includes noise caused by a physiological phenomenon, the noise can be removed by performing the data smoothing. Furthermore, the baseline correction with respect to the deoxygenated hemoglobin enables removal of an amount of increase in the brain blood flow caused by the noise and the physiological phenomenon, and understanding of the increase or decrease in the brain blood flow volume in detail.

FIG. 32 will be referred to again for the description. The varying threshold is assumed to be 0.05. The determining unit 130 calculates 65 seconds at which the brain blood flow volume falls below the varying threshold, as a decrease start time. Furthermore, the increase start time at which the brain blood flow volume increases is calculated as 80 seconds, and the concentration section is calculated as a period between 65 seconds and 80 seconds. The determining unit 130 calculates a degree of concentration as according to Embodiments 1 and 2, For example, since the concentration section is 15 seconds between 65 seconds and 80 seconds within 30 seconds between 60 seconds and 90 seconds, the degree of concentration is calculated as 50% (=15÷30×100).

When the brain blood flow volume is within thresholds (for example, with a tolerance of 0.05), the determining unit 130 determines no concentration section and the degree of concentration to be 0 for the content item.

Since the brain blood flow volume measured as the concentration of oxygenated hemoglobin is within the thresholds both during display of the video that describes the monocular camera of the company A from 0 second to 30 seconds and during display of the video that describes the digital camera of the company C from 30 second to 60 seconds, the determining unit 130 determines the type of reaction as having no degree of concentration.

The content item such as a commercial of a product needs to give the user a strong impression of the product itself and impress the user with the name and others to influence on the next buying behavior.

Thus, the content evaluation apparatus 200 according to Embodiment 3 uses the line-of-sight information including a line-of-sight position of the user when the user views the content item, in addition to the brain blood flow volume in order to evaluate whether or not the user is aware of the product, the product name, and the function included in the content item.

Information for identifying an image that represents a product, a company name, description a function, and a price that are visually included in an image content item will be hereinafter referred to as "provided information". In other words, the provided information includes information on which the content creator wants the user to focus. Accordingly, the content creator can determine appropriateness of an amount of provided information, display timing, the layout of each information on a screen, and others, in addition to the type of a psychological state of the user.

Again with reference to FIG. 30, the line of sight obtaining unit 115B detects a line of sight of the user who views the content item. Specifically, the line of sight obtaining unit 115B detects, at predetermined time intervals, coordinates of a line-of-sight position on a screen, such as a television screen, a PC screen, and a mobile terminal screen, on which the content item is displayed.

Figure 34A:
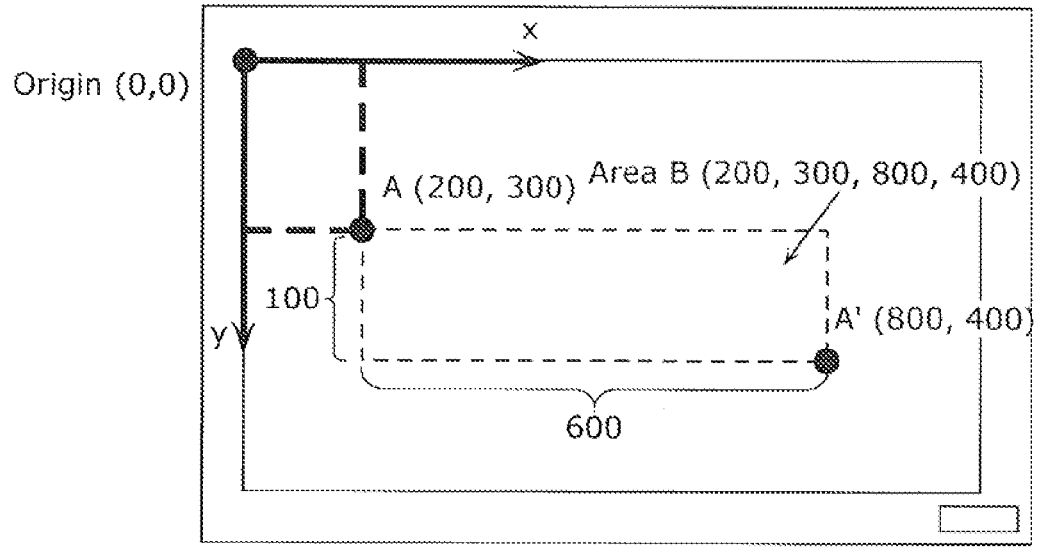
FIG. 34A illustrates a coordinate system of screen on which the user views a content item.
Figure 34B:
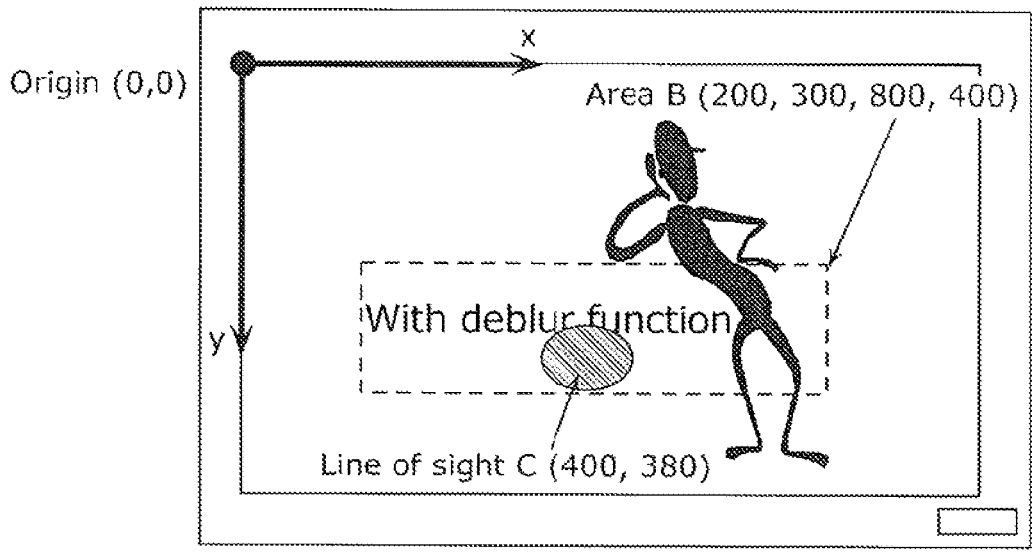
FIG. 34B illustrates an example of a line-of-sight position when the user views a content item.

FIGS. 34A and 34B illustrate a coordinate system of a screen on which the user views a content item according to Embodiment 3. The horizontal axis of the screen represents an X coordinate, the vertical axis represents a Y coordinate, and the upper left corner point is the origin (0, 0). The coordinate system uses one pixel as one unit, and the right direction of the X axis is positive, and the downward direction of the Y axis is also positive. FIG. 34A illustrates positions and an area on the screen. In FIG. 34A, a line-of-sight position when the user gazes at a point A is, for example, (200, 300). Furthermore, a line-of-sight position when the user gazes at a point A' moved from the point A by 600 pixels in the right direction and 100 pixels in the downward direction is (800, 400). Furthermore, a predetermined rectangular area, such as a rectangular display area B enclosed by the points A and A', is represented by (X coordinate of the upper left point, Y coordinate of the upper left point, X coordinate of the lower right point, Y coordinate of the lower right point). For example, the display area B is represented by (200, 300, 800, 400).

Furthermore, the line of sight obtaining unit 115B detects a line-of-sight position at predetermined time intervals, such as 10 milliseconds (ms). Accordingly, the gaze degree calculating unit 204 can measure movement of a line of sight and a retention period during which the line of sight is retained. Here, the retention period is, for example, a period during which a movement distance of a line-of-sight position of the user is smaller than or equal to a predetermined threshold. Specifically, the retention period can be calculated from the transition of a line-of-sight position at predetermined time intervals that are detected. For example, assume a case where a line of sight was at a point C (400, 380) from 3.5 seconds to 5.5 seconds after start of the measurement in FIG. 34B, In other words, the line of sight remained for 2 seconds at the coordinates C (400, 380). As such, the gaze degree calculating unit 204 can identify a retention period by calculating the time difference. There are various conventional methods for detecting a line-of-sight position by capturing an image of an eyeball of a subject and detecting a line of sight of the subject using a position of a pupil in the eyeball (for example, see PTL 4). The line of sight obtaining unit 115B according to the present disclosure can detect a line-of-sight using such a method.

Figure 35A:
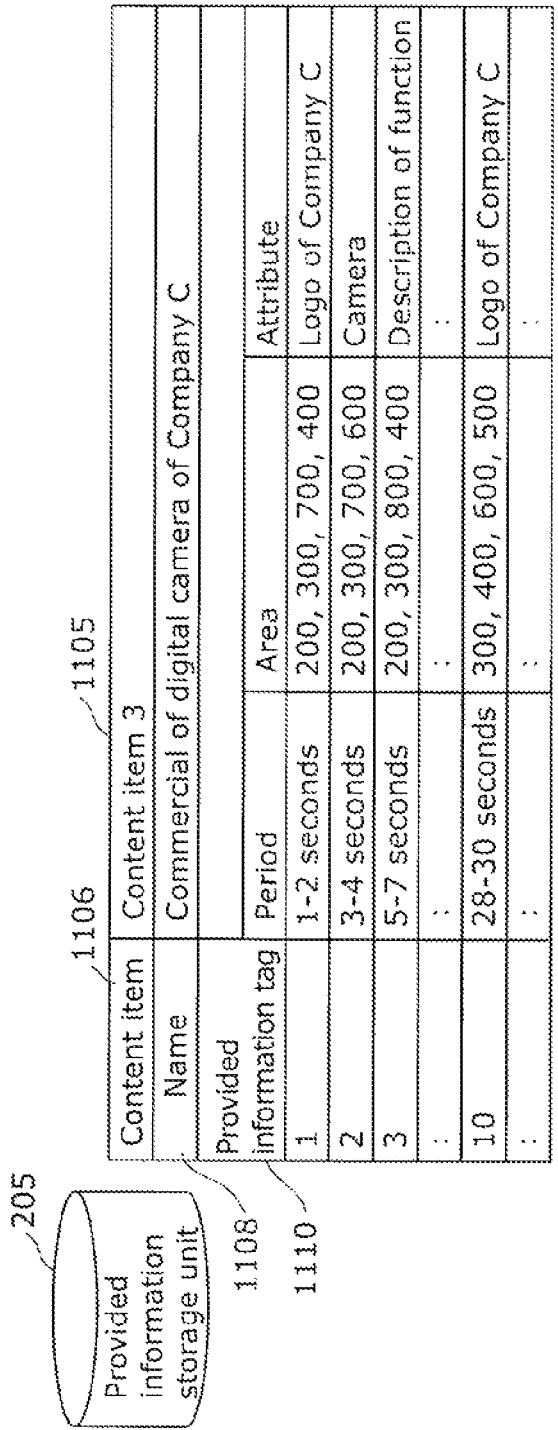
FIG. 35A is an example of provided information stored in a provided information storage unit.

Next, the provided information stored in the provided information storage unit 205 will be described in detail with reference to FIG. 35A. FIG. 35A illustrates a data structure of provided information 1105 according to Embodiment 3.

As illustrated in FIG. 35A, the provided information storage unit 205 stores the provided information 1105 corresponding to at least one content item. Each provided information 1105 includes, for example, a name 1108 of a content item 1106, and at least one provided information tag 1110.

The provided information tag 1110 is associated with an identifier, a display period during which a provided image is displayed in the content item, a display area of the provided image, and an attribute of the provided image. One provided information tag may be associated with a plurality of provided images and respective attributes.

Here, the provided image is an image that is selected from among the images included in the content item according to the intention of the content creator who wants the user to pay attention to the image. Furthermore, the attribute of the provided image may be, for example, a role of the provided image in the content item (description of a product and its function), and a type of information indicated by the provide image (a logo representing text information and a photograph of the external appearance as video information).

In other words, when the user sees commercials of four companies A to D and provides an evaluation for each of the commercials, the commercials are defined as content items, and each of the content items is associated with one provided information. Each of the content items includes a photograph of the external appearance of a camera, a logo of a product name, and a provided image of a use situation, etc, and the provided information is identified by a provided information tag.

For example, with reference to the provided information 1105 corresponding to a content item 3, the name of the content item is "Commercial of digital camera of Company C". The provided information tag having an identifier 1 indicates that the display period of the provided image is between 1 second to 2 seconds, the display area is (200, 300, 700, 400), and the attribute is a logo of Company C.

The tag represents that a provided image representing the logo of Company C is displayed in the display area (200, 300, 700, 400) between 1 second to 2 seconds.

The provided information tag having an identifier 2 indicates that the display period of the provided image is between 3 second to 4 seconds, the display area is (200, 300, 700, 600), and the attribute is a camera.

The tag represents that a provided image representing the camera of Company C is displayed in the display area (200, 300, 700, 600) between 3 to 4 seconds.

As such, the provided information storage unit 205 stores, as provided information, a display area of a provided image on which the content creator wants the user to focus. Furthermore, it is expected that the user may remember or be impressed with a product name and its function by focusing on the display area, which may consequently motivate the user to purchase the product.

The user who viewed the content item of a product is often simply aware of a person appeared in the content item, such as an actor or an actress or mainly aware of the story of the content item, and is not aware of the product or the company who sells the product. As a result, the user does not remember anything about the product. When the content item itself needs to impact the user, the content item may be as such. However, the actual content is created so that the user remembers and is impressed with a function and a product appealed in the content item.

Here, the gaze degree calculating unit 204 determines a gaze degree.

For example, the gaze degree calculating unit 204 calculates a vertical distance from the line-of-sight position of the user to a display area corresponding to the display period, with reference to the provided information 1105. When the calculated vertical distance is larger than or equal to a predetermined threshold, the gaze degree calculating unit 204 determines that the user does not focus on the provided information identified by the display area.

Then, the gaze degree calculating unit 204 calculates a gaze degree based on a ratio of the provided information tag for identifying a provided information focused by the user, to all the provided information tags included in the content item. For example, when in the content item 3 illustrated in FIG. 35A, 20 provided information tags are defined and the user gazes at the provided images identified by 10 of the provided information tags, the gaze degree calculating unit 204 calculates the gaze degree as 50%.

The provided information storage unit 205 may store provided information described in a tag format, such as provided information 1105a in FIG. 35B. For example, the provided information is described in Extensible Markup Language (XML).

FIG. 34B is a part of a scene of the product video of the company C. In the display area B (200, 300, 800, 400) on the screen, a provided image including text information that describes a function read With deblur function is displayed. Here, the user gazes at the line-of-sight position (400, 380). Since the line of sight is within the display area of the provided image, the gaze degree calculating unit 204 determines that the user gazes at the product description.

The gaze degree calculating unit 204 may calculate a retention period of a line-of-sight position, and determine that the use gazes only when the line-of-sight position is retained for a predetermined threshold period or longer. In particular, since images included in a movie content item are frequently switched, even when the line of sight is within a display area indicated by a provided information tag, the user sometimes does not understand the content item. Here, the gaze degree calculating unit 204 may set a threshold (1 second or longer) and determine whether or not the user gazes based on a retention period and a line-of-sight position.

For example, the gaze degree calculating unit 204 may determine that the user gazes at a provided image corresponding to a display area, when a vertical distance between a line-of-sight position at a certain time t and a display area corresponding to a display period including the time t is smaller than or equal to a predetermined threshold, and a retention period of the line-of-sight position is longer than or equal to a predetermined threshold.

Furthermore, the gaze degree calculating unit 204 may calculate a higher gaze degree as the retention period in which a line-of-sight position is retained within a display area is longer. For example, the gaze degree calculating unit 204 may determine whether or not the user gazes at a provided image by assigning a larger weight to a gaze degree as the retention period is longer. The gaze degree calculating unit 204 can calculate a higher gaze degree as the retention period is longer by summing the number of gazes to each of which a weight is assigned.

Figure 36A:
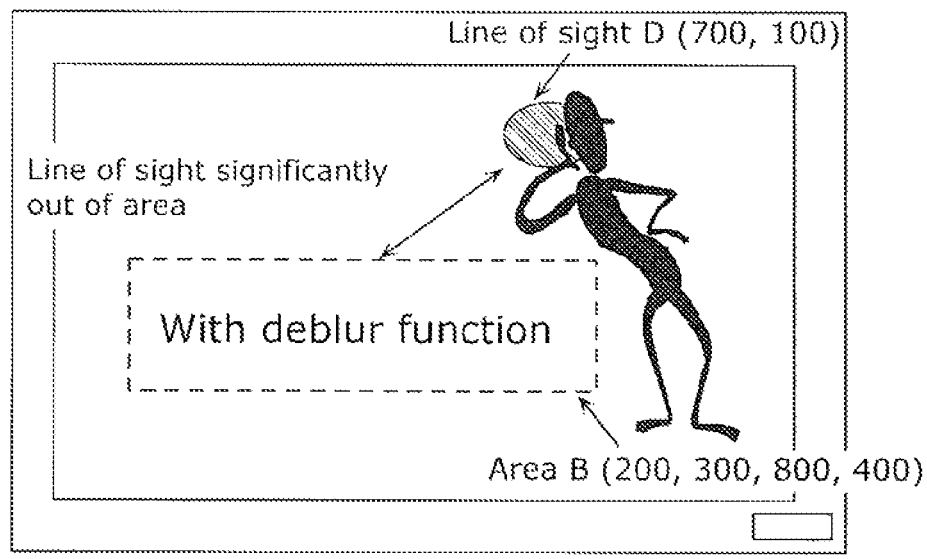
FIG. 36A illustrates an example of a line-of-sight position of another user observed in the experiment of the inventors.
Figure 36B:
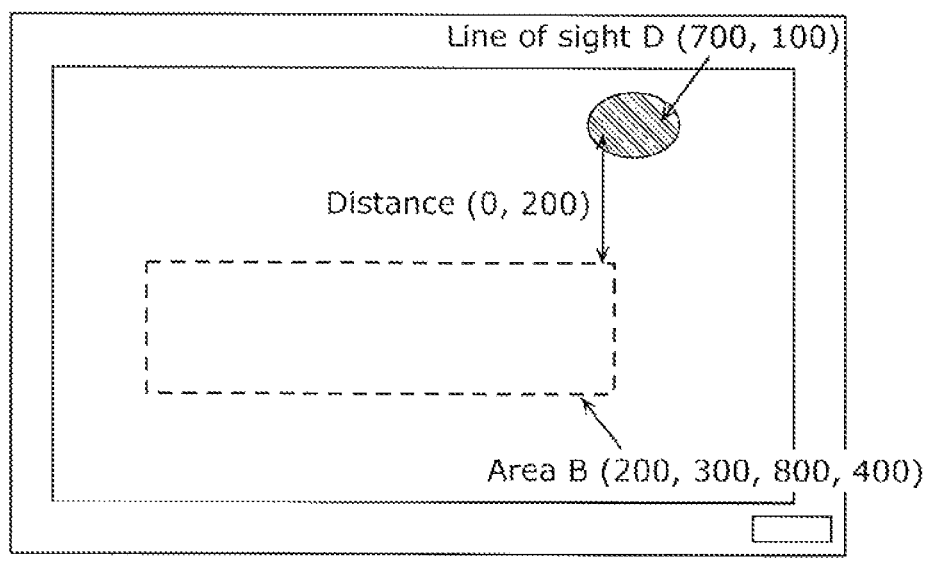
FIG. 36B illustrates an example of a line-of-sight position of another user observed in the experiment of the inventors.

FIGS. 36A and 36B illustrate an example of a line-of-sight position of another user that was observed in the experiment by the inventors.

FIG. 36A is a part of a scene of the product video of the company C similar to that in FIG. 34B. The line-of-sight position of the user illustrated in FIG. 36A is different from that in FIG. 34B, In FIG. 36A, the user gazed at a line-of-sight position D (700, 100). Furthermore, the scene continued for 3 seconds, and the line of sight of the user was retained at the line-of-sight position D (700, 100) also for the 3 seconds.

Although the content creator wants the user to focus on the provided image read "With deblur function" that is the text information on the product description, the line of sight continued to be retained in the face of the actor (actress)

located at the line-of-sight position D. Thus, the line of sight is significantly out of the area B. The vertical distance from the coordinates of the line-of-sight position (700, 100) to the region is equivalent to a distance from the coordinates (700, 100) to the coordinates (700, 300), that is, 200 (=(0, 200)). For example, assuming the threshold of the distance as 100, the gaze degree calculating unit 204 determines that the user does not gaze at the display area B because the distance is larger than or equal to the threshold.

As described above, the gaze degree calculating unit 204 calculates a gaze degree, for example, at a ratio of the number of provided images at which the user gazes and which are identified by some of the provided information tags included in each of the content items, to the total of provided images. As illustrated in FIG. 35A, "Commercial of digital camera of Company C" in the content item 3 has the total 10 provided information tags. Assume that the user does not gaze at the provided image corresponding to one of the 10 provided information tag having the identifier 1, and the line of sight of the user is within predetermined regions in the other 9 scenes. Here, the gaze degree is calculated as 9/10=90%.

Figure 37:
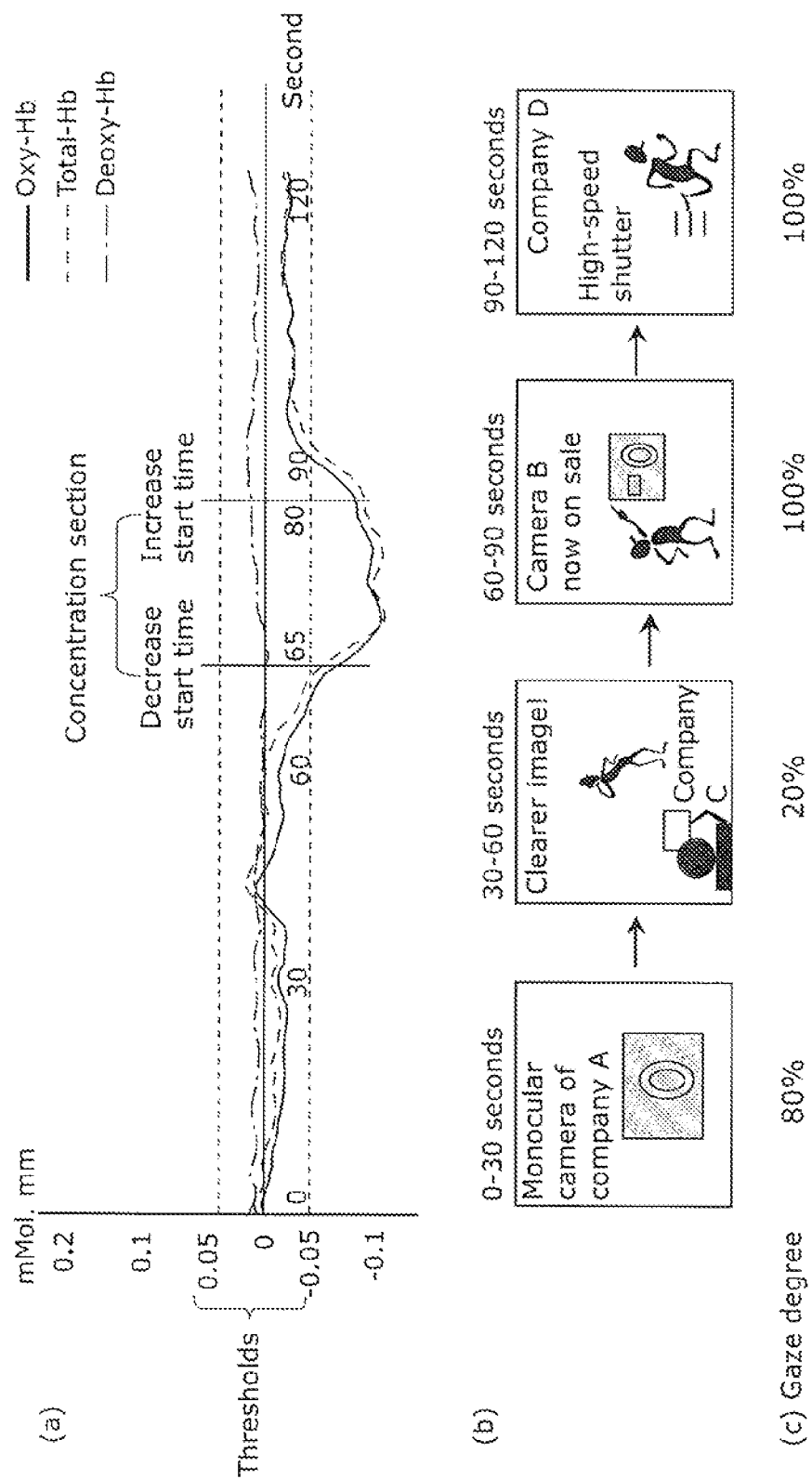
FIG. 37 illustrates a correspondence relationship between video content items, a brain blood flow volume, and gaze degrees based on the experiment conducted by the inventors.

FIG. 37 illustrates a correspondence relationship between video content items, a brain blood flow volume, and gaze degrees based on the experiment conducted by the inventors. (a) of FIG. 37 is a graph indicating temporal change in the brain blood flow volume as (a) of FIG. 32. Furthermore, (c) of FIG. 37 indicates the gaze degree calculated for each of the content items (video of product description) viewed by the user and indicated in (b) of FIG. 37.

Since a line-of-sight position at which the user views each of two of ten provided images in the movie that describes a product of the company A from 0 to 30 seconds is distant from a display area by a threshold or more, the gaze degree calculated by the gaze degree calculating unit 204 is 80%. Furthermore, a line-of-sight position is within a display area of each of the provided images in the movies that describe products of the companies B and D, the gaze degree is 100%. In the movie that describes a product of the company C from 30 to 60 seconds, the user only gazes at the actor (actress) and does not see the product name and its function, and the gaze degree is 20%.

As illustrated in FIG. 37, the evaluation information determining unit 206 included in the content evaluation apparatus 200 determines an evaluation of a content item based on a relationship between the brain blood flow volume and the gaze degree.

Specifically, the evaluation information determining unit 206 determines an evaluation of a content item, based on the gaze degree calculated from a line of sight and a type of reaction identified from the brain blood flow volume. More specifically, the evaluation information determining unit 206 determines the evaluation with reference to a template on the evaluations stored in the evaluation information storage unit 207 (hereinafter referred to as "evaluation information template").

Figure 38:
FIG. 38 is an example of an evaluation information template stored in the evaluation information storage unit.

FIG. 38 is an example of an evaluation information template 2107 stored in the evaluation information storage unit 207 according to Embodiment 3. In the evaluation information template 2107, the evaluation information is associated with a pair of a degree of concentration based on a brain blood flow volume and a ranked gaze degree.

Here, the gaze degrees have two ranks: a relatively lower rank between 0% inclusive and 30% exclusive; and a relatively higher rank between 30% and 100% inclusive.

Furthermore, reactions have two types: a no-reaction type with a relatively lower degree of concentration between 0% inclusive and 30% exclusive; and a concentration type with a relatively higher degree of concentration of 30% or higher.

For example, when a reaction is classified as "no-reaction type" and a gaze degree is between 0% inclusive and 30% exclusive, it can be determined that the excitation and impact of the user to the content item is lower, and a degree at which the user gazes at a function and a product that the content creator wants to advertizes is also lower. Thus, the evaluation information storage unit 207 stores the evaluation information template including evaluations and changes, such as "Impact tends to be low. Need to increase gaze degree by changing timing for providing information and layout of information", as the evaluation information when the type of reaction is the no-reaction type and the gaze degree is between 0% inclusive and 30% exclusive.

Other than this, the evaluation information storage unit 207 stores an evaluation information template for each pair of a type of reaction and a gaze degree, as indicated in FIG. 38.

The evaluation information determining unit 206 can determine the evaluation information corresponding to the type of reaction and the gaze degree as an evaluation for the content item of the user, with reference to the evaluation information template.

Generally, an electroencephalogram signal is hard to be interpreted from its waveform and the information. Furthermore, as described in Embodiment 3, there are many cases where amounts of biosignals during the time when a certain content item is viewed are enormous and it is hard to recognize on which portion of the biosignals needs to be focused and how to interpret the biosignals. Thus, the content creator and others can easily evaluate a content item by providing the evaluation information based on a gaze degree of the content item and a degree of concentration using the brain blood flow volume.

The presenting unit 108 outside of the content evaluation apparatus 200 may display an evaluation for the content item determined by the evaluation information determining unit 206 as a result of an evaluation for the content item.

Figure 39:
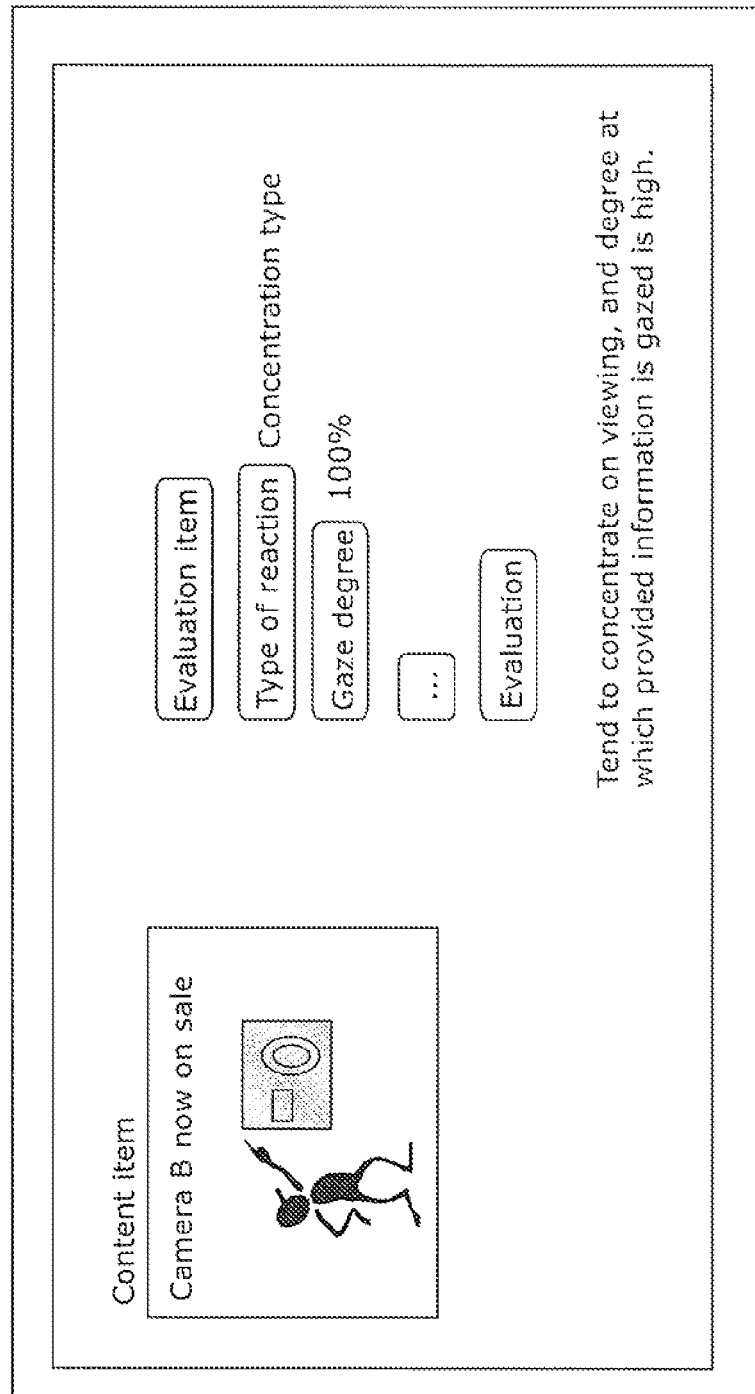
FIG. 39 illustrates an example of a content evaluation result displayed on the presenting unit.

FIG. 39 illustrates an example of a content evaluation result displayed on the presenting unit 108.

The type of reaction, a gaze degree, an evaluation, improvement, and others are displayed for the content item of the commercial of the company B. In other words, the degree of concentration for the movie that describes the product of the company B viewed by the user between 60 and 90 seconds after start of the viewing is as high as 50%, and the type of reaction is classified as "concentration type". Furthermore, the gaze degree is indicated as 100%. Furthermore, the integrated evaluation that reads "Tend to concentrate on viewing, and degree at which provided information is gazed is high." is displayed.

The procedure of the content evaluation apparatus 200 according to Embodiment 3 will be described with reference to FIGS. 40 to 44.

Figure 40:
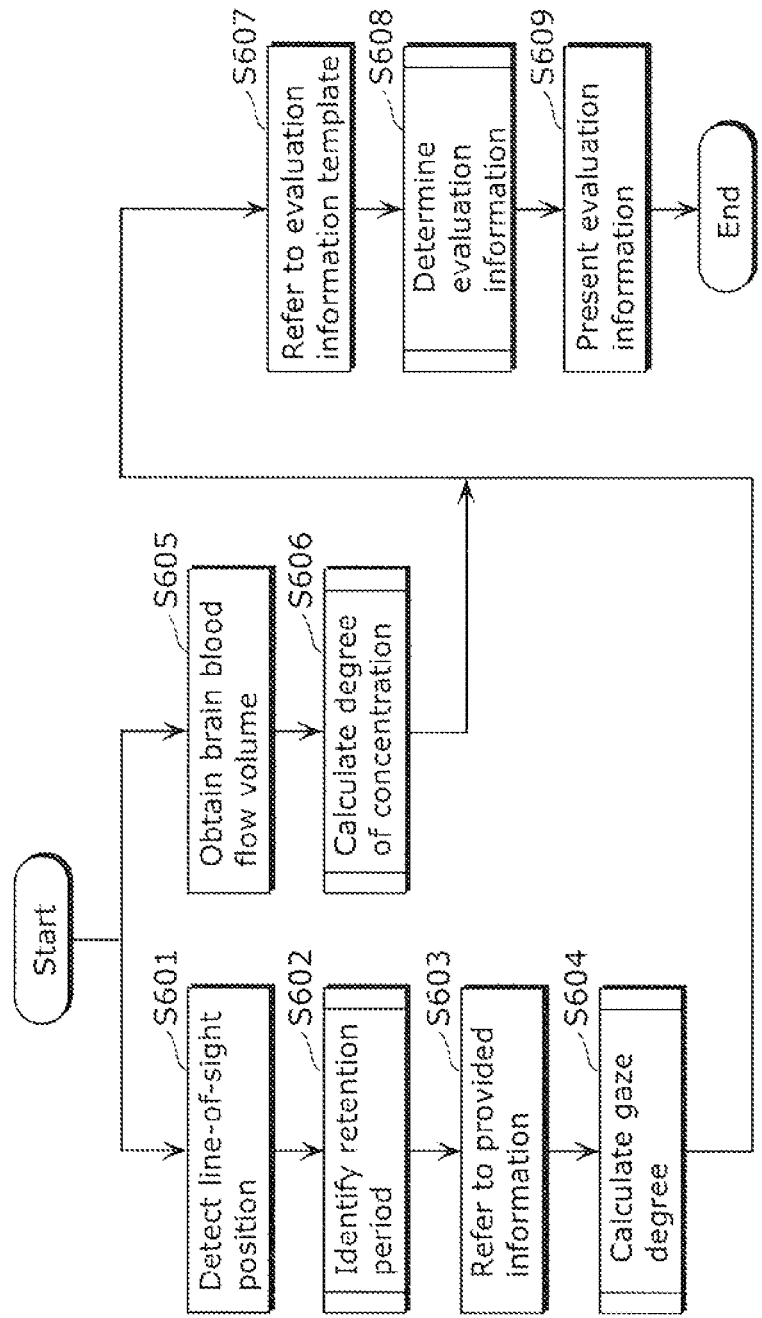
FIG. 40 is a flowchart indicating processes performed by a content evaluation apparatus according to Embodiment 3.

FIG. 40 is a flowchart indicating processes performed by the content evaluation apparatus 200 according to Embodiment 3.

The brain blood flow volume obtaining unit 101 obtains a brain blood flow volume of the user (Step S605). The gaze degree calculating unit 204 calculates a degree of concentration based on an amount of increase or decrease in the obtained brain blood flow volume with respect to the brain blood flow volume at a base time (Step S606).

Figure 41:
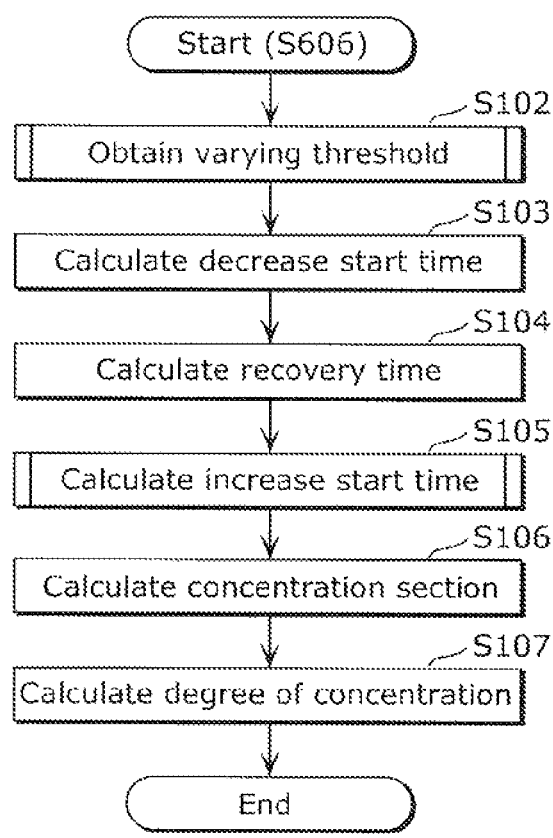
FIG. 41 is a detailed flowchart of the process of calculating a degree of concentration (Step S606 in FIG. 40).

FIG. 41 is a detailed flowchart of the process of calculating a degree of concentration (Step S606 in FIG. 40). The determining unit 130 calculates a decrease start time and an increase start time, and then a concentration section as according to Embodiments 1 and 2. The degree of concentration is calculated based on the concentration section.

Again with reference to FIG. 40, the line of sight obtaining unit 115B detects a line-of-sight position at predetermined intervals in parallel with Step S605 (Step S601). Next, the gaze degree calculating unit 204 identifies a line-of-sight position and a retention period, based on time series data of line-of-sight positions obtained by the line of sight obtaining unit 115B (Step S602).

Figure 42:
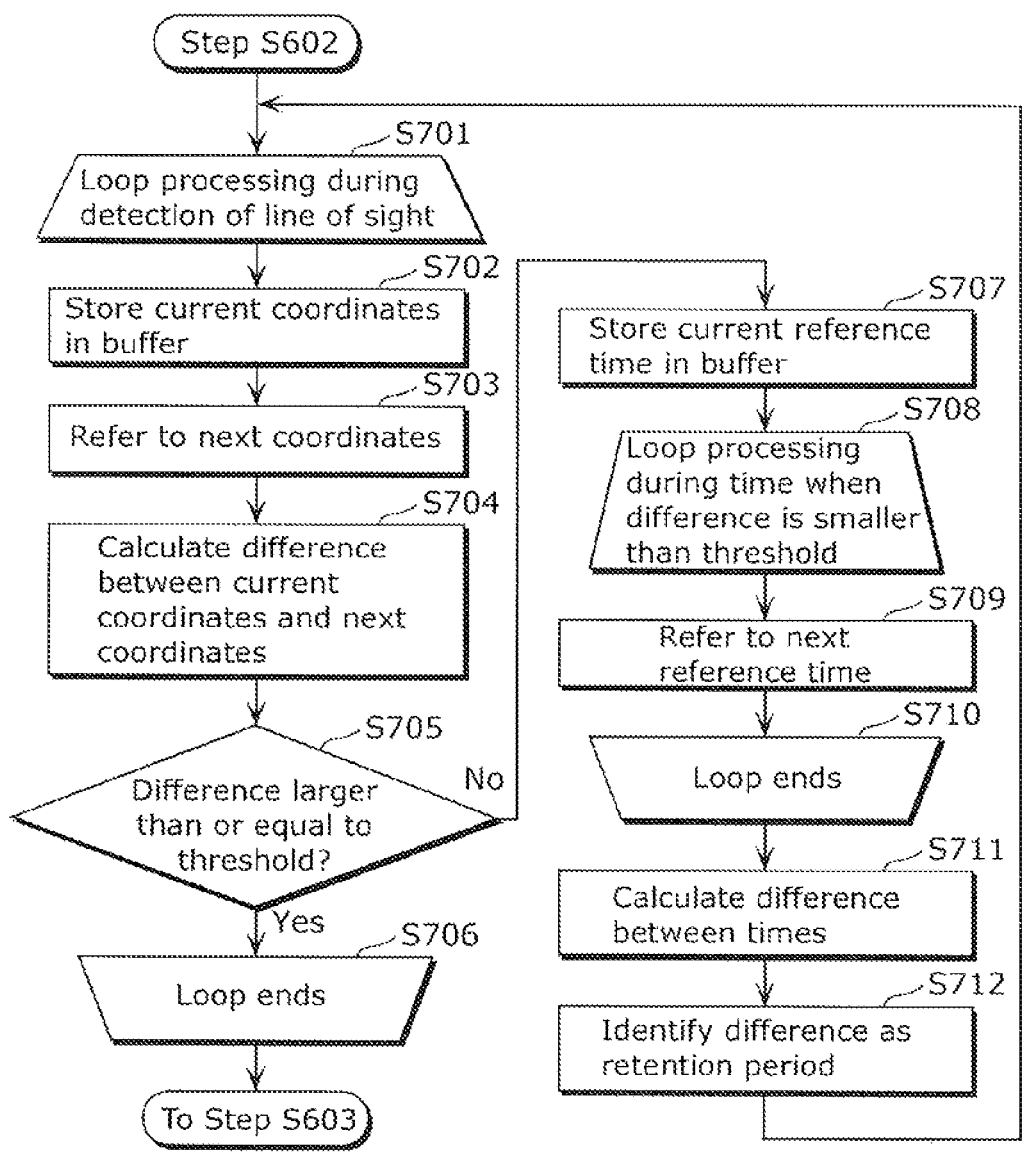
FIG. 42 is a detailed flowchart of the process of identifying a retention period of a line of sight (Step S602 in FIG. 40).

FIG. 42 is a detailed flowchart of the process of identifying a retention period of a line of sight (Step S602 in FIG. 40).

The gaze degree calculating unit 204 calculates a retention period of a line-of-sight position by repeating processes of Steps S701 to S706 to be described below during the detection of a line of sight (that is, until the content evaluation apparatus 200 obtains all line-of-sight positions necessary for evaluating a content item).

First, the gaze degree calculating unit 204 stores coordinates indicating the current line-of-sight position in a buffer (Step S702). Then, the gaze degree calculating unit 204 refers to the coordinates indicating the current line-of-sight position with the next sampling timing (Step S703), and calculates a difference between the current coordinates stored in the buffer and the next coordinates (Step S704). For example, the gaze degree calculating unit 204 sets a predetermined threshold to each of the X and Y coordinates, such as with a tolerance of 10, and determines whether or not the difference is larger than or equal to the threshold (Step S705). When the difference is larger than or equal to the threshold (Yes at Step S705), the gaze degree calculating unit 204 restarts the loop processing because it can be determined that the line of sight moves (Step S706).

When the difference is smaller than the threshold (No at Step S705), the gaze degree calculating unit 204 stores the current reference time in the buffer to measure the retention period (Step S707). During the time when the difference is smaller than the threshold, while the current reference time is referred to with each sampling timing (Step S709), the loop processing is performed (Steps S708 to S710). When the difference exceeds, the loop processing ends (Step S710). The gaze degree calculating unit 204 calculates a difference between the time at which the loop processing ends and a period during which the coordinates are stored in the buffer (Step S711). Then, the gaze degree calculating unit 204 identifies the obtained difference as a retention period (Step S712). Accordingly, the line-of-sight position and the retention period at the line-of-sight position are obtained one by one.

Again with reference to FIG. 40, the gaze degree calculating unit 204 refers to the provided information stored in the provided information storage unit 205 (Step S603). Then, the gaze degree calculating unit 204 calculates a gaze degree by determining whether or not the user gazes at all the provided images included in each content item, based on the line-of-sight positions and the retention periods (Step S604).

Figure 43:
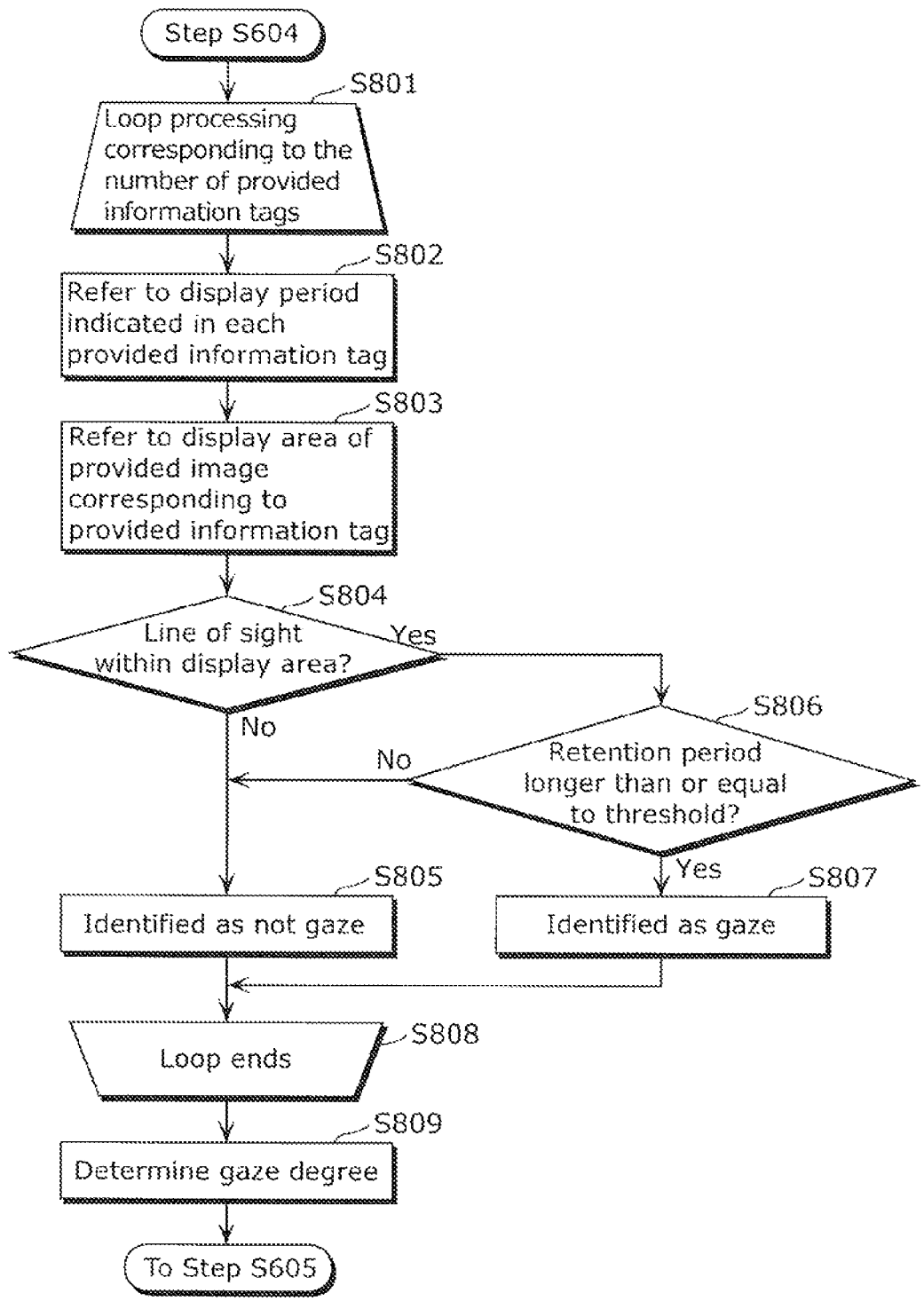
FIG. 43 is a detailed flowchart of the process of calculating a gaze degree (Step S604 in FIG. 40).

FIG. 43 is a detailed flowchart of the process of calculating a gaze degree (Step S604 in FIG. 40). The gaze degree calculating unit 204 according to Embodiment 3 calculates a gaze degree for each content item including a plurality of provided images.

The gaze degree calculating unit 204 performs the loop processing corresponding to the number of provided information tags (Steps S801 to S808). In other words, the gaze degree calculating unit 204 refers to the display period indicated in each of the provided information tags (Step S802), and to the display area of the provided image corresponding to the provided information tag (Step S803). Taking an example of the provided information tag having the identifier 1 in FIG. 35A, the display period is between 1 and 2 seconds, and the display area is (200, 300, 700, 400) in which the provided image indicating the logo of the company name is displayed.

Then, the gaze degree calculating unit 204 determines whether or not the line-of-sight position during the display period corresponding to the provided information tag is within the display area (Step S804). When the line-of-sight position is not within the display area (No at Step S804), the provided image is identified as a provided image that is not gazed by the user because the user does not see the display area (Step S805). On the other hand, when the line-of-sight position is within the display area (Yes at Step S804), it is determined whether or not the retention period of the line-of-sight position is longer than or equal to a threshold (Step S806).

When the retention period is shorter than the threshold (No at Step S806), it is probable that the user does not understand the details of the content item. Thus, it is determined that the user does not gaze at the provided image (Step S805). On the other hand, when the retention period is longer than or equal to the threshold (Yes at Step S806), it is determined that the user gazes at the provided image (Step S807). The gaze degree calculating unit 204 ends the loop processing after repeating Steps 801 and 808 for each of the provided information tags included in the provided information (Step S808). As a result, it is determined whether or not the user gazes at each of the provided images identified by the provided information tags. Accordingly, the gaze degree calculating unit 204 calculates a ratio of the number of provided information tags that identify the provided images at which the user gaze, to the total of the provided information tags included in the content item, as a gaze degree (Step S809).

Next, again with reference to FIG. 40, the evaluation information determining unit 206 refers to the evaluation information template stored in the evaluation information storage unit 207 (Step S607). Then, the evaluation information determining unit 206 determines evaluation information based on the type of reaction and the gaze degree (Step S608).

Figure 44:
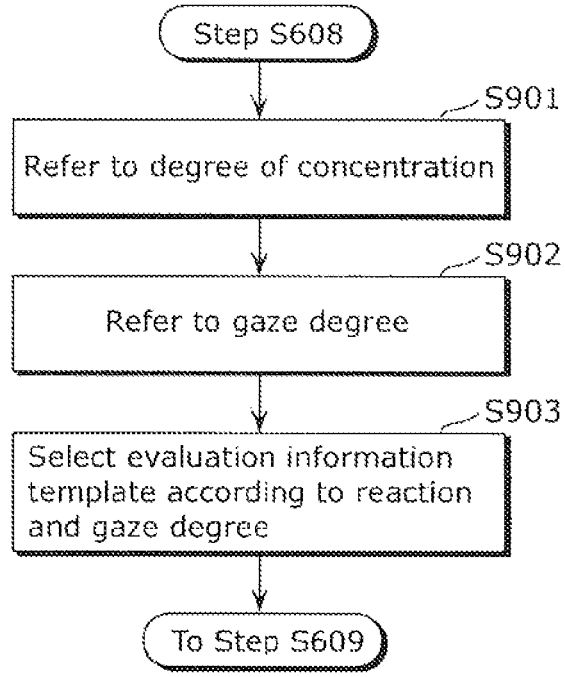
FIG. 44 is a detailed flowchart of the process of determining evaluation information (Step S608 in FIG. 40).

FIG. 44 is a detailed flowchart of the process of determining evaluation information (Step S608 in FIG. 40). The evaluation information determining unit 206 refers to a degree of concentration of the user on the content item identified by the determining unit 130 (Step S901), and to the gaze degree of the user to the content item calculated by the gaze degree calculating unit 204 (Step S902). Then, the evaluation information corresponding to the degree of concentration and the gaze degree is selected from the evaluation information template stored in the evaluation information storage unit 207 to determine an evaluation of the user to the content item (Step S903).

Figure 45:
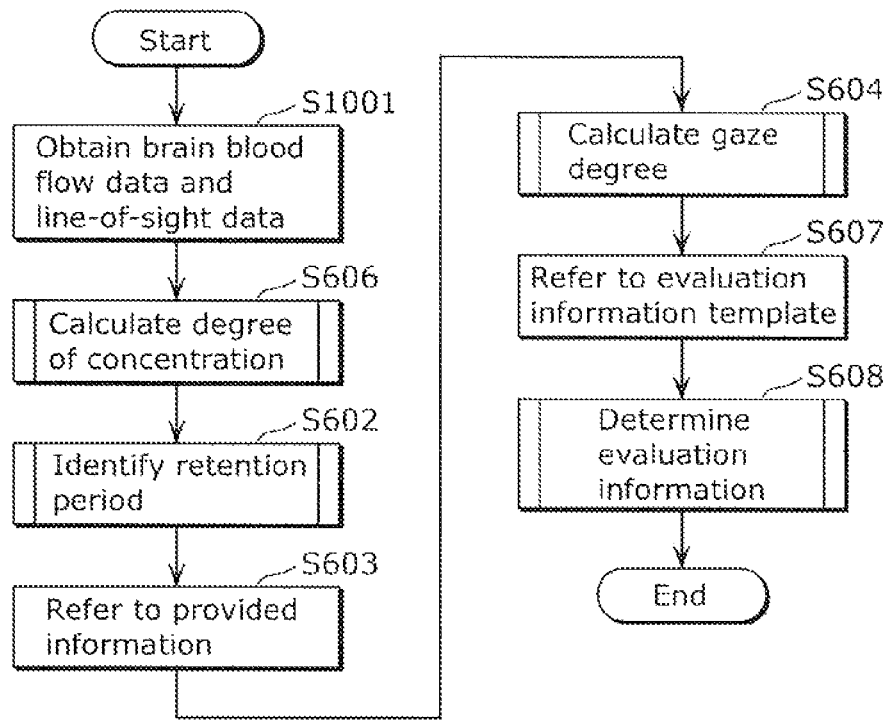
FIG. 45 is a flowchart indicating processes performed by the content evaluation apparatus according to Embodiment 3 when the content evaluation apparatus obtains a biosignal from an external device.

The brain blood flow volume obtaining unit 101 and the line of sight obtaining unit 115B according to Embodiment 3 may obtain the brain blood flow volume and the line-of-sight position, by reading the brain blood flow volume and the line-of-sight position that are obtained by an external device of the content evaluation apparatus 200 from recording media and others. Furthermore, the brain blood flow volume obtaining unit 101 and the line of sight obtaining unit 115B may obtain the brain blood flow volume and the line-of-sight position that are obtained by the external device of the content evaluation apparatus 200 through a wired or wireless communication interface. FIG. 45 indicates the processes performed by the content evaluation apparatus 200 in this case. The processes identical to those in FIG. 40 will be denoted by the same reference numerals, and the detailed description thereof will be omitted.

FIG. 45 is a flowchart indicating the processes performed by the content evaluation apparatus 200 when the content evaluation apparatus 200 obtains a biosignal from the external device. As indicated in FIG. 45, the brain blood flow volume obtaining unit 101 and the line of sight obtaining unit 115B obtain brain blood flow data and line-of-sight data that are obtained from the external device of the content evaluation apparatus 200, respectively (S1001). In this case, Step S606 and Steps S602 to S604 do not have to be performed in parallel, and can be performed sequentially.

Although at least one of a distance between a display area and a line-of-sight position and a retention period of a line of sight is compared with a threshold as a method for calculating a gaze degree by the gaze degree calculating unit 204 according to Embodiment 3, the calculation method is not limited to such, and various methods may be considered. One example will be described below.

Figure 46A:
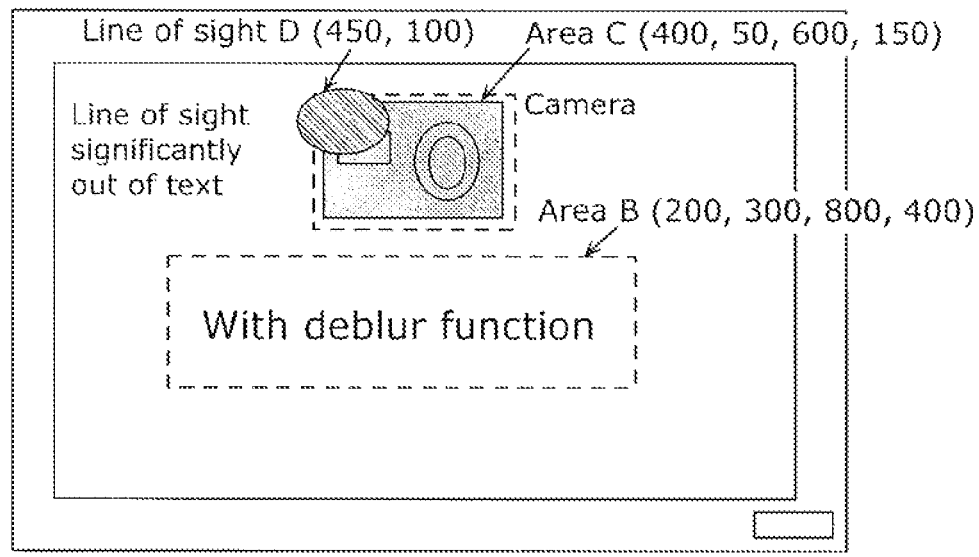
FIG. 46A illustrates another example of a line-of-sight position of the user observed in the experiment.
Figure 46B:
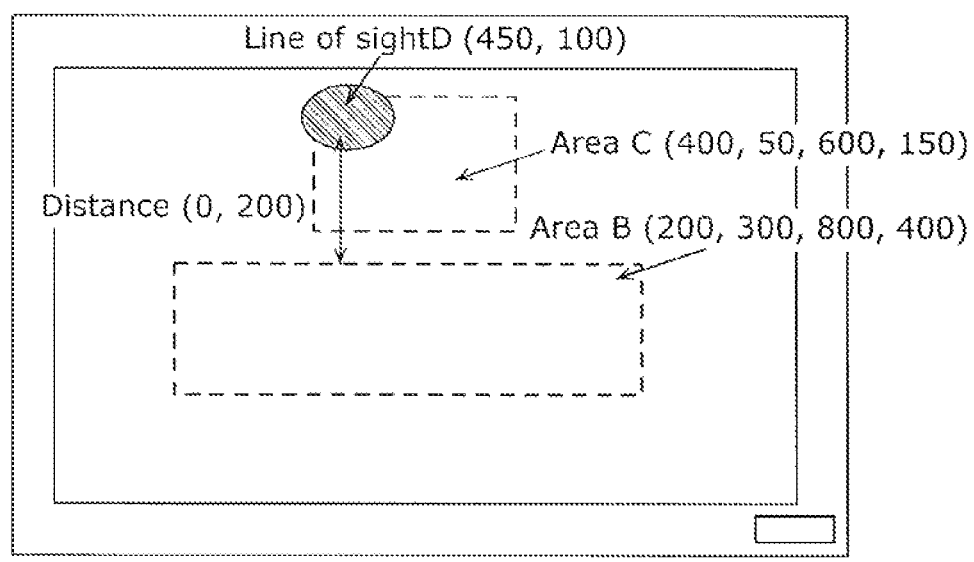
FIG. 46B illustrates another example of a line-of-sight position of the user observed in the experiment.

The gaze degree calculating unit 204 according to Embodiment 3 determines whether or not the use gazes by determining whether or not a line of sight is within a target display area. For example, in FIG. 36B, the gaze degree calculating unit 204 calculates a vertical distance between the display area B (200, 300, 800, 400) that is a display area and the line of sight D as 200. However, depending on a scene, display areas are displayed at the same time. FIGS. 46A and 46B will be referred to for the description.

Each screen of FIGS. 46A and 46B includes a display area B (200, 300, 800, 400) and a display area C (400, 50, 600, 150). The line-of-sight position of the user is at a point D (450, 100). Here, the line-of-sight position is distant from the display area B. However, the line-of-sight position is within the area C on which the appearance of the camera is displayed. The content creator wants to appeal not only text that describes the function but also the appearance of the camera as the content item. Here, the gaze degree calculating unit 204 may determine that the user gazes at the provided image, when one of the display areas B and C includes the line-of-sight position. This is because the user cannot simultaneously see two positions.

Furthermore, although the gaze degree calculating unit 204 according to Embodiment 3 determines that the user gazes when the retention period is longer than or equal to a threshold (for example, 1 second), the method is not limited to such. For example, the gaze degree calculating unit 204 may determine that the user gazes at the provided image when the ratio of the retention period to the total viewing period of the provided content item is larger than or equal to a predetermined threshold.

Furthermore, the gaze degree calculating unit 204 may calculate a higher gaze degree to the provided image at which the line of sight is retained as the ratio of the retention period to the total viewing period of the provided content item is larger. As the retention period to the total period of the provided content item is longer, it is probable that the user gazes.

Furthermore, the gaze degree calculating unit 204 may calculate a gaze degree by assigning a weight to each provided information tag. For example, when a content item includes 10 provided information tags $P_1$ to $P_{10}$, and weights $w_1$ to $w_{10}$ are associated with the provided information tags, respectively, the gaze degree calculating unit 204 may calculate the gaze degree by $\Sigma w_i / \Sigma w_j$. Here, $w_i$ is a weight of a provided information tag including a provided image determined by the gaze degree calculating unit 204 that the user gazes, and $w_j$ is a weight assigned to all of the provided information tags.

Furthermore, the gaze degree calculating unit 204 may calculate a gaze degree using the number of provided images at which the user gazes. For example, the gaze degree calculating unit 204 may calculate, as a gaze degree, a ratio of the number of provided images at which the user gazes to the total number of provided images identified by the provided information tags.

Figure 47A:
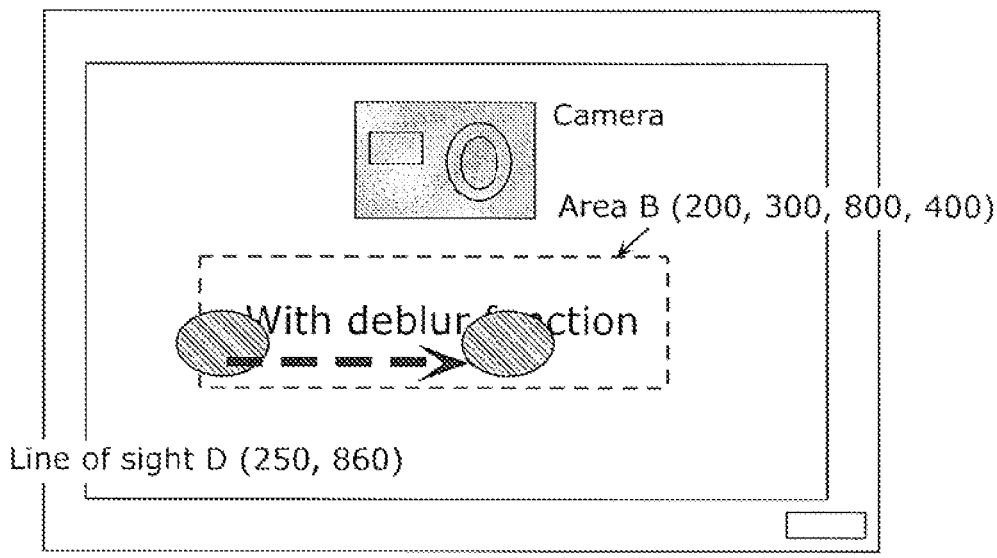
FIG. 47A illustrates a method for calculating a gaze degree of text information by the user.
Figure 47B:
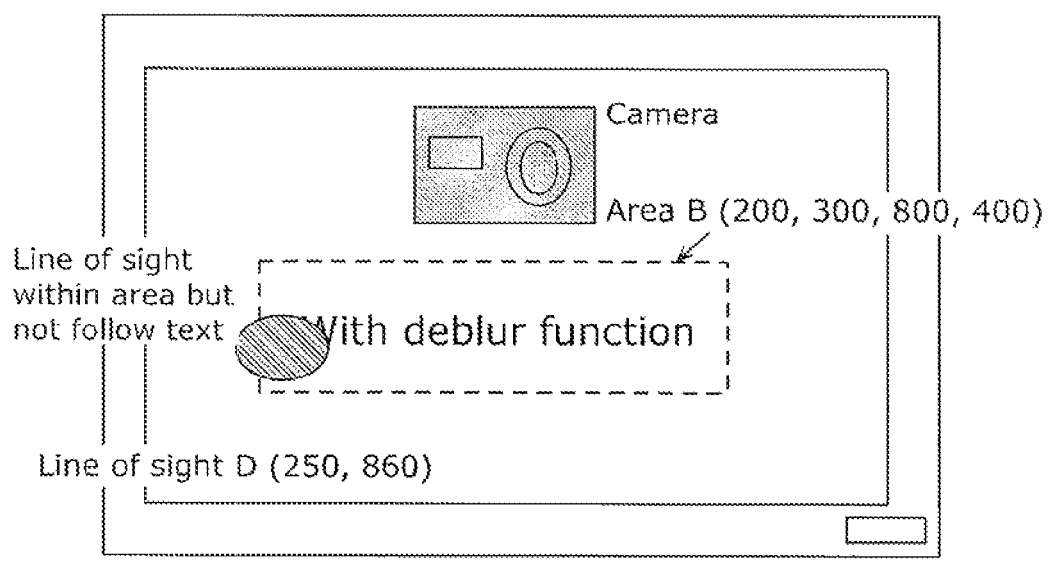
FIG. 47B illustrates a method for calculating a gaze degree of text information by the user.

Furthermore, when a provided image represents text information (that is, when an attribute of the provided image is text information, such as a logo), the gaze degree calculating unit 204 may consider whether or the text information is followed by the eyes. In other words, the following has to be considered: not only whether or not a distance from a line-of-sight position to a display area of a provided image representing the text information is simply smaller than or equal to a predetermined distance but also whether or not the line-of-sight position moves in a direction in which the text information is written. FIGS. 47A and 47B will be referred to for the description.

FIGS. 47A and 47B illustrate a method for calculating a gaze degree of text information by the user.

In FIGS. 47A and 47B, the line of sight of the user is retained at a position a (250, 860). The display area on which the content creator wants the user to focus is a display area B (200, 300, 800, 400). Thus, the line-of-sight position is within the display area. Accordingly, the gaze degree calculating unit 204 determines that the user gazes at the display area B, simply based on a distance between a display area and a line-of-sight position in both of FIGS. 47A and 47B.

However, the text information written in the horizontal direction from the left to the right "With deblur function" is displayed in the display area B. Thus, when the user actually focuses on the display area B, generally, the text is followed by the eyes from the left to the right. Thus, it is possible to determine whether or not the user gazes at a provided image representing text information with accuracy, by determining whether or not the line-of-sight position moves in a direction identical to that when the user reads the text information. For example, when the line-of-sight position moves from the left corner to the right corner in the display area B, the gaze degree calculating unit 204 may determine that the user gazes at the area B. Furthermore, when the line-of-sight position is retained at the left corner of the display area B, the gaze degree calculating unit 204 may determine that the user does not gaze at the area B. Furthermore, even when the line of sight is within a display area but is retained at the same position, the gaze degree calculating unit 204 may calculate a lower gaze degree.

In other words, when a provided image represents text information, the gaze degree calculating unit 204 may calculate a higher gaze degree as a movement direction of a line-of-sight position matches a direction in which the text information is written at a higher degree. Information indicating that the provided image represents text information and information representing a direction in which the information is written may be included in the provided information tags as attributes of the provided image.

Furthermore, when a provided image represents text information, the gaze degree calculating unit 204 may determine that the user gazes at the provided image only when a movement distance of the line-of-sight position is larger than or equal to a predetermined value. For example, the gaze degree calculating unit 204 may determine that the user gazes only when the line-of-sight position moves by more than 70% of a horizontal width (length in an X coordinate direction) of an image area representing text information.

In other words, the gaze degree calculating unit 204 determines that the user gazes only when a difference between a line-of-sight position of the user and a model obtained by digitizing, in advance, general movement of a line of sight when the user views a content item is smaller than or equal to a predetermined threshold.

The content evaluation apparatus 200 according to Embodiment 3 can evaluate a content item using, as evaluation axes, a type of a psychological reaction of the user to the content item and a gaze degree at which the user gazes at a specific image included in the content item that are obtained from biosignals of the user who views the content item. As a result, the content creator can easily rank a desired content item in view of the purposes of the creation of the content item, on the evaluation axes of the type of a psychological reaction and the gaze degree. Thus, the content creator can assess a difference between the evaluation determined by the content evaluation apparatus 200 and the desired content item. Thus, the content creator can easily use the evaluation determined by the content evaluation apparatus 200 for improving the content item.

Specifically, each of the devices may be configured as a computer system including a micro processing unit, a ROM, and a RAM, a hard disk drive, a display unit, a key board, and a mouse. The RAM or the hard disk drive stores a computer program. The micro processing unit operates according to the computer program, so that each of the devices fulfills its function. Here, the computer program includes a plurality of instruction codes indicating instructions to a computer to fulfill a predetermined function. The program is a program for determining whether or not the user concentrates, and causes a computer to execute: obtaining a brain blood flow volume of the user; obtaining a varying threshold that is a value smaller than the brain blood flow volume of the user at a base time; and determining that the user concentrates, when the brain blood flow volume obtained in the obtaining of a brain blood flow volume falls below the varying threshold obtained in the obtaining of a varying threshold.

Moreover, part or all of the constituent elements included in each of the above devices may be included in one system Large Scale Integration (LSI). The system LSI is a super-multifunctional LSI manufactured by integrating components on one chip and is, specifically, a computer system including a micro processing unit, a ROM, and a RAM. The RAM stores a computer program. The micro processing unit operates according to the computer program, so that the system LSI fulfills its function.

Furthermore, part or all of the constituent elements included in each of the above devices may be included in an IC card removable from each of the devices or in a stand alone module. The IC card or the module is the computer system including the micro processing unit, the ROM, and the RAM. The IC card or the module may include the super-multifunctional LSI. The micro processing unit operates according to the computer program, so that the IC card or the module fulfills its function. The IC card or the module may have tamper-resistance.

Moreover, the devices described above may be implemented as any of the above methods. Furthermore, the methods may be implemented as a computer program to be executed by a computer, and as a digital signal included in the computer program.

Furthermore, in the present disclosure, the computer program or the digital signal may be recorded on a non-transitory computer-readable recording medium such as a flexible disk, a hard disk, a CD-ROM, an MO, a DVD, a DVD-ROM, a DVD-RAM, a Blu-ray Disc® (BD), and a semiconductor memory. In addition, the digital signal may be recorded on these recording media.

Furthermore, in the present disclosure, the computer program or the digital signal may be transmitted via an electronic communication line, a wireless or wired communication line, a network represented by the Internet, data broadcasting, and the like.

Moreover, the present disclosure may relate to a computer system including a micro processing unit and a memory. The memory may store the computer program, and the micro processing unit may operate according to the computer program.

Furthermore, the computer program or the digital signal may be implemented in another independent computer system by recording the computer program or the digital signal on the recording medium and transporting the recording medium or by transmitting the computer program or the digital signal via a network or the like.

Furthermore, Embodiments and Modifications above may be combined with each other.

The essential constituent elements of the concentration presence/absence determining device according to the present disclosure are a brain blood flow volume obtaining unit, a varying threshold obtaining unit, and an determining unit, and a presenting unit does not necessarily have to be included in the concentration presence/absence determining device.

Although the concentration presence/absence determining device and the content evaluation apparatus according to one or more aspects of the present disclosure are described based on Embodiments 1 to 3, the present disclosure is not limited to these. Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for realizing the concentration presence/absence determining device and the content evaluation apparatus according to each of the embodiments is a program described below.

The herein disclosed subject matter is to be considered descriptive and illustrative only, and the appended Claims are of a scope intended to cover and encompass not only the particular embodiments disclosed, but also equivalent structures, methods, and/or uses.

INDUSTRIAL APPLICABILITY

The present disclosure is applicable to a concentration presence/absence determining device that determines whether or not the user concentrates based on increase or decrease in the brain blood flow volume and a degree-of-concentration determining device that determines a degree of concentration.

The invention claimed is:

1. A concentration presence/absence determining device that determines whether or not a user is concentrating, the concentration presence/absence determining device comprising:
   a near-infrared spectroscopy sensor which senses a plurality of values of a hemoglobin state in brain blood of the user;
   a processor; and
   a non-transitory computer-readable recording medium having stored thereon executable instructions, which when executed by the processor, cause the concentration presence/absence determining device to:
   obtain the plurality of values of the hemoglobin state in the brain blood of the user from the near-infrared spectroscopy sensor;
   calculate a varying threshold;
   obtain a value of the varying threshold at a base time;
   determine that the user is concentrating, when a first value of the plurality of values of the hemoglobin state in the brain blood of the user falls below the value of the varying threshold;
   evaluate, based on the determination that the user is concentrating, a degree of concentration of the user; and
   present a result of the evaluated degree of concentration of the user, wherein
   the varying threshold is calculated using repeated loop processing, by increasing a reference time between a start time and an end time,
   the obtained value of the varying threshold is a negative maximum value of the calculated varying threshold, based on a result of the repeated loop processing, and
   the result of the evaluated degree of concentration of the user is based on a comparison of a characteristic of the plurality of values of the hemoglobin state in the brain blood of the user with a characteristic of a task executed by the user.

2. The concentration presence/absence determining device according to claim 1,
   wherein the executable instructions, when executed by the processor, cause the concentration presence/absence determining device to further:
   calculate, as a decrease start time, a time at which the first value of the hemoglobin state in the brain blood of the user falls below the value of the varying threshold;
   calculate, as a recovery time, a time at which a second value of the plurality of values of the hemoglobin state in the brain blood of the user exceeds the value of the varying threshold after the calculated decrease start time;
   calculate, as an increase start time, a time at which a group of values of the plurality of values of the hemoglobin state in the brain blood of the user start to increase between the calculated decrease start time and the calculated recovery time; and
   calculate, as a concentration section, a period in which the user is concentrating, the period ranging from the calculated decrease start time to the calculated increase start time.

3. The concentration presence/absence determining device according to claim 2,
   wherein the executable instructions, when executed by the processor, cause the concentration presence/absence determining device to further:
   calculate, as the degree of concentration of the user, a ratio of the concentration section to a target section that is a period during which the task is executed by the user.

4. The concentration presence/absence determining device according to claim 3,
   wherein the executable instructions, when executed by the processor, cause the concentration presence/absence determining device to further:
   calculate a weighted degree of concentration of the user by multiplying the calculated degree of concentration by a weight that increases with a larger amount of decrease in values of the plurality of values of the hemoglobin state in the brain blood of the user in the concentration section.

5. The concentration presence/absence determining device according to claim 3,
   wherein the executable instructions, when executed by the processor, cause the concentration presence/absence determining device to further:
   calculate a weighted degree of concentration of the user by multiplying the calculated degree of concentration by a weight that increases with a higher ratio of an amount of decrease in values of the plurality of values of the hemoglobin state in the brain blood of the user in the concentration section to an amount of decrease in values of the plurality of values of the hemoglobin state in the brain blood of the user when the user is at rest.

6. The concentration presence/absence determining device according to claim 5,
   wherein the amount of decrease in the values in the plurality of values of the hemoglobin state in the brain blood of the user in the concentration section is a difference between the values of the plurality of values of the hemoglobin state in the brain blood of the user when the user is at rest and a smallest value of the values of the plurality of values of the hemoglobin state in the brain blood of the user in the concentration section.

7. The concentration presence/absence determining device according to claim 4,
   wherein the amount of decrease in the values of the plurality of values of the hemoglobin state in the brain blood of the user in the concentration section is an absolute value of an integrated value of values of the plurality of values of the hemoglobin state in the brain blood of the user ranging from the decrease start time to a time at which the hemoglobin state in the brain blood of the user has a smallest value in the concentration section.

8. The concentration presence/absence determining device according to claim 3,
   wherein the executable instructions, when executed by the processor, cause the concentration presence/absence determining device to further:
   classify a pattern of change in values of the plurality of values of the hemoglobin state in the brain blood of the user in the target section into one of patterns, and calculate a weighted degree of concentration of the user by multiplying the calculated degree of concentration by a weight assigned to the classified pattern.

9. The concentration presence/absence determining device according to claim 8,
   wherein the executable instructions, when executed by the processor, cause the concentration presence/absence determining device to further:
   classify the pattern of change in the values of the plurality of values of the hemoglobin state in the brain blood of the user in the target section into one of the patterns, based on one of (i) the ratio of the concentration section to the target section, (ii) the number of concentration sections within the target section, and (iii) a ratio of a smallest value of values of the plurality of values of the hemoglobin in the brain blood of the user in a first concentration section to a smallest value of values of the plurality of values in the hemoglobin state in the brain blood flow volume in a second concentration section, the first concentration section and the second concentration section being included in the target section, and the concentration sections including the concentration section.

10. The concentration presence/absence determining device according to claim 3,
wherein the executable instructions, when executed by the processor, cause the concentration presence/absence determining device to further:
calculate a weighted degree of concentration of the user by multiplying the calculated degree of concentration by a weight that increases with the less number of concentration sections within the target section, the concentration sections including the concentration section.

11. The concentration presence/absence determining device according to claim 3,
wherein the executable instructions, when executed by the processor, cause the concentration presence/absence determining device to further:
obtain values of hemoglobin states in the brain blood of the user measured at a plurality of measurement parts of the brain of the user, the values of the hemoglobin states in the brain blood of the user including the plurality of values of the hemoglobin state in the brain blood of the user, and
calculate, for each of the measurement parts of the plurality of measurement parts, a ratio of an amount of decrease in values of the hemoglobin state in the brain blood of the user in the concentration section to an amount of decrease in values of the hemoglobin state in the brain blood of the user when the user is at rest, and calculate the degree of concentration of the user, using values of one of the hemoglobin states in the brain blood of the user measured at a measurement part of the plurality of measurement parts having a highest ratio that is calculated.

12. The concentration presence/absence determining device according to claim 11,
wherein the plurality of measurement parts are grouped into groups, and
the executable instructions, when executed by the processor, cause the concentration presence/absence determining device to further:
calculate, for each of the groups, an average of ratios of (i) amounts of decrease in values of the hemoglobin states in the brain blood of the user measured at measurement parts included each group, in the concentration section (ii) to amounts of decrease in values of the hemoglobin states in the brain blood of the user measured at the measurement parts included each group when the user is at rest, and calculate the degree of concentration of the user, using an average of the values of the hemoglobin states in the brain blood of the user measured at the measurement parts included in one of the groups having a highest average of the ratios that is calculated.

13. The concentration presence/absence determining device according to claim 3, wherein the executable instructions, when executed by the processor, cause the concentration presence/absence determining device to further:
present the calculated degree of concentration of the user or the calculated weighted degree of concentration of the user.

14. The concentration presence/absence determining device according to claim 2,
wherein the executable instructions, when executed by the processor, cause the concentration presence/absence determining device to further:
obtain a plurality of values of a hemoglobin state in brain blood of each of users including the user,
calculate a degree of concentration of each of the users, and
calculate, as a multiple-degree of concentration, one of (i) a ratio of the number of users each having the degree of concentration that exceeds a predetermined threshold to the total number of users, (ii) an average of decrease start times of the users, and (iii) an average of increase start times of the users.

15. The concentration presence/absence determining device according to claim 2, wherein the executable instructions, when executed by the processor, cause the concentration presence/absence determining device to further:
obtain a line-of-sight position of the user; and
calculate, as a target section, a period during which the obtained line-of-sight position of the user is within a predetermined area.

16. A content evaluation apparatus, comprising:
a second processor;
a second non-transitory computer-readable recording medium having stored thereon second executable instructions; and
the concentration presence/absence determining device according to claim 1 that determines a concentration state;
wherein the second executable instructions, when executed by the second processor, cause the content evaluation apparatus to:
obtain a line-of-sight position of the user;
calculate a gaze degree that is a degree at which the user gazes at a provided image that is an image included in an image content item viewed by the user, with reference to provided information based on a position relationship, during a display period, between the line-of-sight position and a display area of the provided image, the provided information being information including the display area and the display period, the display period being a period during which the provided image is displayed in the display area; and
determine, as an evaluation of the user to the image content item, evaluation information corresponding to the calculated gaze degree and to the concentration state determined by the concentration presence/absence determining device, with reference to an evaluation information template including evaluation information of the image content item associated with a pair of a gaze degree and a concentration state.

17. The content evaluation apparatus according to claim 16,
wherein the evaluation information template includes the evaluation information indicating an evaluation that increases with a higher gaze degree of the user and a higher degree of concentration of the user.

18. The content evaluation apparatus according to claim 16,
wherein the second executable instructions, when executed by the second processor, cause the content evaluation apparatus to further:
calculate a higher gaze degree as a period during which the line-of-sight position is retained in the display area is longer.

19. The content evaluation apparatus according to claim 16,
wherein when the provided image represents text information, the second executable instructions, when executed by the second processor, cause the content evaluation apparatus to further calculate a higher gaze degree as a movement direction of the line-of-sight position matches a direction in which the text information is written at a higher degree.

20. The content evaluation apparatus according to claim 16,
wherein the second executable instructions, when executed by the second processor, cause the content evaluation apparatus to further:
determine whether or not a distance between (i) a line-of-sight position during each of display periods included in the provided information and (ii) a display area corresponding to the display period is smaller than a predetermined threshold, for each of the display periods, determine that the user gazes during at least one of the display periods when the distance is smaller than the predetermined threshold, and calculate a gaze degree as a ratio of a sum of the at least one of the display periods during which it is determined that the user gazes, to the display periods included in the provided information.

21. The content evaluation apparatus according to claim 16,
wherein the image content item is a content item of a commercial video.

22. A concentration presence/absence determining method for determining whether or not a user is concentrating, the concentration presence/absence determining method comprising:
sensing, using a near-infrared spectroscopy sensor, a plurality of values of a hemoglobin state in brain blood of the user;
obtaining, using a hardware processor, the plurality of values of the hemoglobin state in the brain blood of the user from the near-infrared spectroscopy sensor;
calculating, using the hardware processor, a varying threshold;
obtaining, using the hardware processor, a value of the varying threshold at a base time;
determining, using the hardware processor, that the user is concentrating, when a first value of the plurality of values of the hemoglobin state in the brain blood of the user obtained in the obtaining of the plurality of values of the hemoglobin state in the brain blood of the user falls below the value of the varying threshold obtained in the obtaining of a varying threshold;
evaluating, based on the determination in the determining that the user is concentrating, a degree of concentration of the user; and
presenting a result of the evaluation of the degree of concentration of the user in the evaluating, wherein
the varying threshold is calculated in the calculating using repeated loop processing, by increasing a reference time between a start time and an end time,
the value of the varying threshold obtained in the obtaining the value of the varying threshold at the base time is a negative maximum value of the varying threshold calculated in the calculating, based on a result of the repeated loop processing, and
the result of the evaluation of the degree of concentration of the user presented in the presenting is based on a comparison of a characteristic of the plurality of values of the hemoglobin state in the brain blood of the user with a characteristic of a task executed by the user.

23. A non-transitory computer-readable recording medium for use in a computer, the non-transitory computer-readable recording medium having a computer program recorded thereon, the computer program being for determining whether or not a user is concentrating, and causing the computer to execute:
obtaining, using a processor of the computer, a plurality of values of a hemoglobin state in brain blood of the user sensed by a near-infrared spectroscopy sensor;
calculating, using the processor of the computer, a varying threshold;
obtaining, using the processor of the computer, a value of the varying threshold at a base time;
determining, using the processor of the computer, that the user is concentrating, when a first value of the plurality of values of the hemoglobin state in the brain blood of the user obtained in the obtaining of the plurality of values of the hemoglobin state in the brain blood of the user falls below the value of the varying threshold obtained in the obtaining of a varying threshold;
evaluating, based on the determination in the determining that the user is concentrating, a degree of concentration of the user; and
presenting a result of the evaluation of the degree of concentration of the user in the evaluating, wherein
the varying threshold is calculated in the calculating using repeated loop processing, by increasing a reference time between a start time and an end time,
the value of the varying threshold obtained in the obtaining the value of the varying threshold at the base time is a negative maximum value of the varying threshold calculated in the calculating, based on a result of the repeated loop processing, and
the result of the evaluation of the degree of concentration of the user presented in the presenting is based on a comparison of a characteristic of the plurality of values of the hemoglobin state in the brain blood of the user with a characteristic of a task executed by the user.

* * * * *